US011617711B2

(12) United States Patent
Sarikaya et al.

(10) Patent No.: US 11,617,711 B2
(45) Date of Patent: Apr. 4, 2023

(54) COMPOSITIONS AND METHODS FOR DENTAL CARE

(71) Applicant: UNIVERSITY OF WASHINGTON, Seattle, WA (US)

(72) Inventors: Mehmet Sarikaya, Seattle, WA (US); Deniz Tanil Yucesoy, Seattle, WA (US); Hanson Kwok Fong, Seattle, WA (US); Sami Dogan, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 17/269,357

(22) PCT Filed: Aug. 30, 2019

(86) PCT No.: PCT/US2019/049040
§ 371 (c)(1),
(2) Date: Feb. 18, 2021

(87) PCT Pub. No.: WO2020/047395
PCT Pub. Date: Mar. 5, 2020

(65) Prior Publication Data
US 2021/0401717 A1 Dec. 30, 2021

Related U.S. Application Data

(60) Provisional application No. 62/758,230, filed on Nov. 9, 2018, provisional application No. 62/725,160, filed on Aug. 30, 2018.

(51) Int. Cl.
*A61K 8/64* (2006.01)
*A61K 8/19* (2006.01)
*A61K 8/24* (2006.01)
*A61Q 11/00* (2006.01)

(52) U.S. Cl.
CPC ............. *A61K 8/64* (2013.01); *A61K 8/19* (2013.01); *A61K 8/24* (2013.01); *A61Q 11/00* (2013.01); *A61K 2800/92* (2013.01)

(58) Field of Classification Search
CPC ... A61K 8/64; A61K 8/19; A61K 8/24; A61K 2800/92; A61Q 11/00
See application file for complete search history.

(56) References Cited

U.S. PATENT DOCUMENTS

| 4,659,751 | A | 4/1987 | Bowen |
| 5,833,954 | A | 11/1998 | Chow et al. |
| 8,889,161 | B2 | 11/2014 | Latta et al. |
| 9,011,823 | B2 | 4/2015 | Vogel et al. |
| 9,809,633 | B2 | 11/2017 | Sarikawa et al. |
| 9,993,407 | B2 | 6/2018 | Liu et al. |
| 2012/0315226 | A1 | 12/2012 | Legeros et al. |
| 2015/0182640 | A1 | 7/2015 | Sim et al. |
| 2016/0152672 | A1* | 6/2016 | Sari .................. A61P 1/02 514/21.3 |
| 2016/0250379 | A1 | 9/2016 | Jabbari |
| 2018/0078577 | A1 | 3/2018 | Li et al. |
| 2018/0169303 | A1 | 6/2018 | Apicella et al. |
| 2018/0200172 | A1 | 7/2018 | Sarikawa et al. |
| 2018/0236130 | A1 | 8/2018 | Moradian-Oldak et al. |
| 2018/0272031 | A1 | 9/2018 | Beniash et al. |
| 2018/0289606 | A1 | 10/2018 | Tao |

FOREIGN PATENT DOCUMENTS

| CN | 102241738 A | 11/2011 | |
| CN | 106632610 A | 5/2017 | |
| CN | 1084034444 A | 8/2018 | |
| CN | 109288685 A | 2/2019 | |
| JP | 2012167040 A | 9/2012 | |
| JP | 201514///9 A | 8/2015 | |
| KR | 20140094054 A | 7/2014 | |
| MX | 2018006608 A | 9/2018 | |
| RU | 2688230 C1 | 5/2019 | |
| TW | 201836584 A | 10/2018 | |
| WO | 2006062776 A3 | 6/2006 | |
| WO | 2010132126 A1 | 11/2010 | |
| WO | WO-2012166626 A1 * | 12/2012 | ............. A61K 38/39 |
| WO | 2016/0115283 | 7/2016 | |
| WO | 2016202980 A1 | 12/2016 | |
| WO | 2017123986 A1 | 7/2017 | |

OTHER PUBLICATIONS

The International Search Report (ISR) with Written Opinion for PCT/US2019/049040 dated Jan. 6, 2020, pp. 1-15.
Luo, Jingjing et al. "Biomimic Enamel Remineralization by Hybridization Calcium- and Phosphate-Loaded Liposomes with Amelogenin-Inspired Peptide" Key Engineering Materials (2012) vols. 512-515, pp. 1727-1730.
Alkhatib et al. (2004) Prevalence of self-assessed tooth discolouration in the United Kingdom. Journal of dentistry, 32(7):561-566.
Arens et al. (2018) A practical method of bleaching tetracycline-stained teeth. Oral Surgery, Oral Medicine, Oral Pathology 34(5)812-817.
Bakry et al. (2018) Increasing the efficiency of CPP-ACP to remineralize enamel white spot lesions, Journal of Dentistry, Sep. 76:52-57.
Cai et al. (2003) Remineralization of enamel subsurface lesions in situ by sugar-free lozenges containing casein phosphopeptideamorphous calcium phosphate, Australian Dental Journal 48:(4):240-243.

(Continued)

*Primary Examiner* — Catherine S Hibbert
(74) *Attorney, Agent, or Firm* — McDonnell Boehnen Hulbert & Berghoff

(57) ABSTRACT

Disclosed herein are compositions and methods for their use in treating dental disorders, whitening teeth, restoring and retaining the tooth structure and restoring the mineral content of the tooth-mineral loss due to demineralization, wherein the compositions include a first formulation that includes a polypeptide effective to treat a dental disorder and/or whiten teeth, and one or more further formulations including at least one calcium ion source and/or at least one phosphate ion source, wherein the first formulation is configured to release the polypeptide more rapidly than $Ca^{2+}$ is released from the at least one calcium ion source and $PO_4^{3-}$ is released from the at least one phosphate ion source.

16 Claims, 21 Drawing Sheets
Specification includes a Sequence Listing.

(56) References Cited

OTHER PUBLICATIONS

Cao et al. (2013) Biomimetic mineralisation of phosphorylated dentine by CPP-ACP, Journal of Dentistry 41:818-825.
Cao et al. (2014) A novel oligopeptide simulating dentine matrix protein 1 for biomimetic mineralization of dentine, Clin Oral Invest 18:873-881.
Cao et al. (2015) Methods for Biomimetic Remineralization of Human Dentine: A Systematic Review, Int. J. Mol. Sci. 16:4615-4627.
Chen et al. (2005) Clinical evaluation of 546 tetracycline-stained teeth treated with porcelain laminate veneers. Journal of dentistry 33(1)3-8.
Cochrane et al. (2010) New Approaches to Enhanced Remineralization of Tooth Enamel, J Dent Res 89 (11):1187-1197.
Dahl et al. (2003) Tooth bleaching—a critical review of the biological aspects. Critical Reviews in Oral Biology & Medicine 14(4)292-304.
Dogan et al. (2018) Biomimetic Tooth Repair: Amelogenin-derived peptide enables in vitro remineralization of human enamel. ACS Biomater Sci Eng. 4(5):1788-1796.
Dorozhkin et al. (2002) Biological and Medical Significance of Calcium Phosphates, Angew. Chem. Int. Ed. 41: 3130-3146.
Fletcher et al. (2011) Electrospun mats of PVP/ACP nanofibres for remineralization of enamel tooth surfaces, CrystEngComm, 13:3692.
Gjorgievska et al. (2011) Prevention of enamel demineralization after tooth bleaching by bioactive glass incorporated into toothpaste. Australian dental journal 56(2)193-200.
Guentsch et al. (2012) Biomimetic mineralization: Long-term observations in patients with dentin sensitivity, Dental Materials 28 457-464.
Gungormus et al. (2008) Regulation of in vitro Calcium Phosphate Mineralization by Combinatorially Selected Hydroxyapatite-Binding Peptides, Biomacromolecules 9:966-973.
Gungormus et al. (2012) Cementomimetics-constructing a cementum-like biomineralized microlayer via amelogenin-derived peptides. International Journal of Oral Science 4(2)69-77.
Gungormus M. (2012) Selection, Design and Applications of Solid Binding Peptides for Controlled Biomineralization, University of Washington, Materials Science & Engineering Dissertation.
Hanks et al., (1993) Cytotoxicity and dentin permeability of carbamide peroxide and hydrogen peroxide vital bleaching materials, in vitro. Journal of Dental Research 72(5)931-938.
He et al. (2005) Spatially and Temporally Controlled Biomineralization Is Facilitated by Interaction between Self-Assembled Dentin Matrix Protein 1 and Calcium Phosphate Nuclei in Solution, Biochemistry 44:16140-16148.
Hein et al.(2003) In-office vital tooth bleaching-what do lights add? Compendium of continuing education in dentistry 24(4A)340-352.
Hemagaran et al. (2014) Remineralization of the Tooth Structure—The Future of Dentistry, International Journal of PharmTech Research 6(2):487-493.
Jia et al. (2014) Effect of generation 4.0 polyamidoamine dendrimer on the mineralization of demineralized dentinal tubules in vitro, Archives of Oral Biology 59:10851093.
Lee SY, Kwon HK, Kim BL 2008. Effect of dentinal tubule occlusion by dentifrice containing nano-carbonate apatite. J. Oral Rehabilitation. 35(1) 847-853.
Li et al.(2014) The remineralisation of enamel: a review of the literature, Journal of Dentistry, 42 (Supplement 1), June S12-S20.
Liang et al. (2015) 8DSS-promoted remineralization of demineralized dentin in vitro, J. Mater. Chem. B. 3: 6763.
LINK. (1973) Discolouration of the teeth in alkaptonuria and Parkinsonism. Chron Omaha Dist Dent Soc 36:130.
Luk et al. (2004) Effect of light energy on peroxide tooth bleaching. The Journal of the American Dental Association 135(2)194-201.
Matis (2009) A clinical evaluation of two in-office bleaching regimens with and without tray bleaching. Operative dentistry 34(2)142-149.
Nathoo (1997) The chemistry and mechanisms of extrinsic and intrinsic discoloration. The Journal of the American Dental Association 128:6S-10S.
Nixon (1996) Masking severely tetracycline-stained teeth with ceramic laminate veneers. Practical periodontics and aesthetic dentistry: PPAD 8(3)227-35.
Odioso et al. (2000) Impact of demographic, behavioral, and dental care utilization parameters on tooth color and personal satisfaction. Compendium of continuing education in dentistry. Supplement (29)S35-41; quiz S43.
Porto et al. (2009) Diagnosis and treatment of dentinal hypersensitivity. J. Oral Science. 51(3)323-332.
Qi (2012) Remineralization of arlilicial dentinal caries lesions by biomimetically modified mineral trioxide aggregate, Acta Biomaterialia 8:836-842.
Qualtrough et al. (1994) A look at dental esthetics. Quintessence international 25(1).
Rodrigues et al. (2017) Mirror, mirror on the wall, who's the fairest of them all? A critical content analysis on medica tourism. Tourism Management Perspectives 24:16-25.
Ruan et al. (2016) Efficacy of amelogenin-chitosan hydrogel in biomimetic repair of human enamel in pH-cycling systems. J. Biomed Eng Inform. 2(1)119-128.
Sanchez et al. (2004) Tetracycline and other tetracycline-derivative staining of the teeth and oral cavity. International journal of dermatology 43(10)709-715.
Schmidlin et al. (2013) Current management of dentin hypersensitivity. Clinical Oral Investigation. 17(1)55-59.
Sulieman et al. (2005) An overview of tooth discoloration: extrinsic, intrinsic and internalized stains. Dental update, 32(8):463-4, 466-8, 471.
Sulieman et al. (2004) The effect of hydrogen peroxide concentration on the outcome of tooth whitening: an in vitro study. Journal of dentistry 32(4):295-299.
Sundell et al. (1985) Hereditary amelogenesis imperfecta. I. Epidemiology and clinical classification in a Swedish child population. Swedish Dental Journal 9(4)157-169.
Tredwin et al. (2006) Hydrogen peroxide tooth-whitening (bleaching) products: review of adverse effects and safety issues. British dental journal 200(7)371-376.
Walker et al. (2006) Increased remineralization of tooth enamel by milk containing added casein phosphopeptide-amorphous calcium phosphate, Journal of Dairy Research 73:74-78.
Wang et al. (2014) Enhancement of nano-hydroxyapatite bonding to dentin through a collagen/calcium dual-affinitive peptide for dentinal tubule occlusion, Journal of Biomaterials Applications vol. 29(2)268-277.
Wang et al. (2015) Self-assembled peptide nanofibers on graphene oxide as a novel nanohybrid for biomimetic mineralization of hydroxyapatite, Carbon 89:20-30.
Watanabe et al.(1999)Bilirubin pigmentation of human teeth caused by hyperbilirubinemia. Journal of oral pathology & medicine 28(3)128-130.
West et al. (2002) Dentine hypersensitivity: the effects of brushing toothpaste on etched and unetched dentine in vitro. J. Oral rehabilitation. 29(2)167-174.
Yang et al. (2017) Bioinspired Peptide-Decorated Tannic Acid for in Situ Remineralization of Tooth Enamel: In Vitro and in Vivo Evaluation, ACS Biomater. Sci. Eng. 3(12)3553-3562.
Zhou et al. (2012) Polydopamine-Induced Tooth Remineralization, ACS Appl. Mater. Interfaces 4(12)6901-6910.

\* cited by examiner a. No remineralization b. 1 round remineralization c. 2 rounds remineralization d. 3 rounds remineralization a. Before dentin cross section b. After dentin cross section c. Before dentin surface d. After dentin surface e. No remineralization dentin cross section f. No remineralization dentin surface

SEQUENCE LISTING

<160> NUMBER OF SEQ ID NOS: 34

<210> SEQ ID NO 1
<211> LENGTH: 12
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa can be L or I

<400> SEQUENCE: 1

His Thr Leu Gln Pro His His His Xaa Pro Val Val
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide

<400> SEQUENCE: 2

His Thr Leu Gln Pro His His His Leu Pro Val Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

His Thr Leu Gln Pro His His His Ile Pro Val Val
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be H or Q
<220> FEATURE:
<221> NAME/KEY: MISC_FEATURE
<222> LOCATION: (10)..(10)
<223> OTHER INFORMATION: Xaa can be T or I

<400> SEQUENCE: 4

Val Pro Gly Xaa His Ser Met Thr Pro Xaa Gln His
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Val Pro Gly His His Ser Met Thr Pro Thr Gln His
1               5                   10

<210> SEQ ID NO 6
<211> LENGTH: 22
<212> TYPE: PRT
<213> ORGANISM: Artificial Sequence
<220> FEATURE:
<223> OTHER INFORMATION: Synthetic peptide
```

```
<400> SEQUENCE: 6

Pro Gly Tyr Ile Asn Phe Ser Tyr Glu Asn Ser His Ser Gln Ala Ile
1               5                   10                  15

Asn Val Asp Arg Thr Ala
            20

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc
<222> LOCATION: (3)..(3)
<223> OTHER INFORMATION: Xaa can be A or S

<400> SEQUENCE: 7

Trp Pro Xaa Thr Asp Lys Thr Lys Arg Glu Glu Val Asp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic peptide

<400> SEQUENCE: 8

Trp Pro Ala Thr Asp Lys Thr Lys Arg Glu Glu Val Asp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide

<400> SEQUENCE: 9

Trp Pro Ser Thr Asp Lys Thr Lys Arg Glu Glu Val Asp
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be S or T
<220> FEATURE:
<221> NAME/KEY: MISC_FEATURE
<222> LOCATION: (13)..(13)
<223> OTHER INFORMATION: Xaa can be L or I

<400> SEQUENCE: 10

His Pro Pro Xaa His Thr Leu Gln Pro His His His Xaa Pro Val Val
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide
```

```
<400> SEQUENCE: 11

His Pro Pro Ser His Thr Leu Gln Pro His His His Leu Pro Val Val
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

His Pro Pro Thr His Thr Leu Gln Pro His His His Ile Pro Val Val
1               5                   10                  15

<210> SEQ ID NO 13
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa can be L or F
<220> FEATURE:
<221> NAME/KEY: MISC_FEATURE
<222> LOCATION: (10)..(10)
<223> OTHER INFORMATION: Xaa can be K or N
<220> FEATURE:
<221> NAME/KEY: MISC_FEATURE
<222> LOCATION: (18)..(18)
<223> OTHER INFORMATION: Xaa can be T or V

<400> SEQUENCE: 13

Pro Gly Tyr Ile Asn Xaa Ser Tyr Glu Xaa Ser His Ser Gln Ala Ile
1               5                   10                  15

Asn Xaa Asp Arg Thr Ala
            20

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide

<400> SEQUENCE: 14

Val Pro Gly Gln His Ser Met Thr Pro Ile Gln His
1               5                   10

<210> SEQ ID NO 15
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa can be L or F
<220> FEATURE:
<221> NAME/KEY: MISC_FEATURE
<222> LOCATION: (10)..(10)
<223> OTHER INFORMATION: Xaa can be K or N
<220> FEATURE:
<221> NAME/KEY: MISC_FEATURE
<222> LOCATION: (18)..(18)
<223> OTHER INFORMATION: Xaa can be T or V
```

```
<220> FEATURE:
<221> NAME/KEY: MISC_FEATURE
<222> LOCATION: (28)..(28)
<223> OTHER INFORMATION: Xaa can be L or F
<220> FEATURE:
<221> NAME/KEY: MISC_FEATURE
<222> LOCATION: (32)..(32)
<223> OTHER INFORMATION: Xaa can be K or N
<220> FEATURE:
<221> NAME/KEY: MISC_FEATURE
<222> LOCATION: (40)..(40)
<223> OTHER INFORMATION: Xaa can be T or V

<400> SEQUENCE: 15

Pro Gly Tyr Ile Asn Xaa Ser Tyr Glu Xaa Ser His Ser Gln Ala Ile
1               5                   10                  15

Asn Xaa Asp Arg Thr Ala Pro Gly Tyr Ile Asn Xaa Ser Tyr Glu Xaa
            20                  25                  30

Ser His Ser Gln Ala Ile Asn Xaa Asp Arg Thr Ala
            35                  40

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Ser Tyr Glu Asn Ser His Ser Gln Ala Ile Asn Val Asp Arg Thr
1               5                   10                  15

<210> SEQ ID NO 17
<211> LENGTH: 24
<212> TYPE: PRT
<213> ORGANISM: Artificial Sequence
<220> FEATURE:
<223> OTHER INFORMATION: Synthetic peptide

<400> SEQUENCE: 17

Leu Pro Pro Leu Phe Ser Met Pro Leu Ser Pro Ile Leu Pro Glu Leu
1               5                   10                  15

Pro Leu Glu Ala Trp Pro Ala Thr
            20

<210> SEQ ID NO 18
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa can be S or T
<220> FEATURE:
<221> NAME/KEY: MISC_FEATURE
<222> LOCATION: (13)..(13)
<223> OTHER INFORMATION: Xaa can be L or I
<220> FEATURE:
<221> NAME/KEY: MISC_FEATURE
<222> LOCATION: (23)..(23)
<223> OTHER INFORMATION: Xaa can be A or I
<220> FEATURE:
<221> NAME/KEY: MISC_FEATURE
<222> LOCATION: (34)..(34)
<223> OTHER INFORMATION: Xaa can be H or Q
```

```
<220> FEATURE:
<221> NAME/KEY: MISC_FEATURE
<222> LOCATION: (40)..(40)
<223> OTHER INFORMATION: Xaa can be T or I

<400> SEQUENCE: 18

His Pro Pro Xaa His Thr Leu Gln Pro His His Xaa Pro Val Val
1               5                   10                  15

Pro Ala Gln Gln Pro Val Xaa Pro Gln Gln Pro Met Met Pro Val Pro
            20                  25                  30

Gly Xaa His Ser Met Thr Pro Xaa Gln His
        35                  40

<210> SEQ ID NO 19
<211> LENGTH: 42
<212> TYPE: PRT
<213> ORGANISM: Artificial Sequence
<220> FEATURE:
<223> OTHER INFORMATION: Synthetic peptide

<400> SEQUENCE: 19

His Pro Pro Ser His Thr Leu Gln Pro His His His Leu Pro Val Val
1               5                   10                  15

Pro Ala Gln Gln Pro Val Ala Pro Gln Gln Pro Met Met Pro Val Pro
            20                  25                  30

Gly His His Ser Met Thr Pro Thr Gln His
        35                  40

<210> SEQ ID NO 20
<211> LENGTH: 42
<212> TYPE: PRT
<213> ORGANISM: Artificial Sequence
<220> FEATURE:
<223> OTHER INFORMATION: Synthetic peptide

<400> SEQUENCE: 20

His Pro Pro Thr His Thr Leu Gln Pro His His His Ile Pro Val Val
1               5                   10                  15

Pro Ala Gln Gln Pro Val Ile Pro Gln Gln Pro Met Met Pro Val Pro
            20                  25                  30

Gly Gln His Ser Met Thr Pro Ile Gln His
        35                  40

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa can be A or I

<400> SEQUENCE: 21

Pro Ala Gln Gln Pro Val Xaa Pro Gln Gln Pro Met Met Pro
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide
```

```
<400> SEQUENCE: 22

Pro Ala Gln Gln Pro Val Ala Pro Gln Gln Pro Met Met Pro
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide

<400> SEQUENCE: 23

Pro Ala Gln Gln Pro Val Ile Pro Gln Gln Pro Met Met Pro
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Ser Tyr Glu Lys Ser His Ser Gln Ala Ile Asn Thr Asp Arg Thr
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Met Leu Pro His His Gly Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Asn Pro Gly Phe Ala Gln Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Lys Trp Lys Arg Trp Trp Trp Trp Arg
1               5

<210> SEQ ID NO 28
<211> LENGTH: 14
<212> TYPE: PRT
<213> ORGANISM: Artificial Sequence
<220> FEATURE:
<223> OTHER INFORMATION: Synthetic peptide
```

```
<400> SEQUENCE: 28

Leu Lys Leu Leu Lys Lys Leu Leu Lys Leu Leu Lys Lys Leu
1               5                   10

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide

<400> SEQUENCE: 29

Cys Pro Phe Val Cys
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 30

Arg Arg Xaa Xaa Arg Phe
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

Ala Leu Leu His His Gly Leu Asn Cys Ala Lys Gly Val Leu Ala
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Leu Trp Lys Thr Leu Leu Lys Lys Val Leu Lys Ala Ala Ala
1               5                   10

<210> SEQ ID NO 33
<211> LENGTH: 20
<212> TYPE: PRT
<213> ORGANISM: Artificial Sequence
<220> FEATURE:
<223> OTHER INFORMATION: Synthetic peptide

<400> SEQUENCE: 33

Gly Leu Arg Lys Arg Lys Arg Lys Phe Arg Asn Lys Lys Glu Lys
1               5                   10                  15

Leu Lys Lys Ile
            20
```

```
<210> SEQ ID NO 34
<211> LENGTH: 15
<212> TYPE: PRT
<213> ORGANISM: Artificial Sequence
<220> FEATURE:
<223> OTHER INFORMATION: Synthetic peptide

<400> SEQUENCE: 34

Arg Lys Arg Ile His Ile Gly Pro Gly Arg Ala Phe Tyr Thr Thr
1               5                   10                  15
```

COMPOSITIONS AND METHODS FOR DENTAL CARE

CROSS REFERENCE

This application is a U.S. national phase of International Application No. PCT/US2019/049040, filed on Aug. 30, 2019, which claims priority to U.S. Provisional Application No. 62/758,230, filed Nov. 9, 2018, and U.S. Provisional Application No. 62/725,160, filed Aug. 30, 2018, all of which are incorporated by reference herein in their entirety.

SEQUENCE LISTING STATEMENT

A computer readable form of the Sequence Listing is filed with this application by electronic submission and is incorporated into this application by reference in its entirety. The Sequence Listing is contained in the file created on Feb. 18, 2021 having the file name "19-1363-PCT-US_SequenceListing_ST25.txt" and is 11 kb in size.

BACKGROUND

Demineralization (loss of mineral content on the surface of tooth) is a major cause of most dental diseases. Loss of mineral can be caused by acidic diet, dry mouth, tooth whitening, tooth wear and caries by the acidogenic bacteria. If left untreated, demineralization may lead to various problems from tooth sensitivity to pain in extreme cases to systemic infections (e.g. heart disease). Demineralization is one of the most common cause for loss of tooth. Dental hypersensitivity (DH) is a common oral health condition affecting the majority of the adult population in the world. In the US alone, a total of approximately $10B is spent in treating hypersensitivity, in tooth paste, clinical pastes and gels, and mouthwashes. Despite enormous number of OTC and clinical products, the treatment options are limited, and hypersensitivity still is the major cause of dental discomfort and patient's well-being. Current tooth whitening methods is the use of highly reactive peroxide-based chemicals which remove discoloration by dissolving stained mineral layer from the surface of teeth. This chemical-etching process is at the expense of the enamel—the fully mineralized outer layer of the tooth crown. Therefore, underlying dentin becomes exposed due to chemical demineralization, creating problems such as hypersensitivity and increased susceptibility to cavities that far outweigh any cosmetic benefits. The American Dental Association reports that enamel erosion caused by peroxide demineralization can lead to adverse effects: hypersensitivity (occurring in 64% of patients), gum recession, pulp inflammation and cavities due to regular use of whitening products.

SUMMARY

In one aspect the disclosure provides compositions or kit, comprising
(a) a first formulation comprising an effective amount to treat a dental disorder and/or whiten teeth of a polypeptide comprising or consisting of the amino acid sequence selected from the group consisting of:
(SYENSHSQAINVDRT)$_{1-10}$ (shADP5; SEQ ID NO:16);
(SYEKSHSQAINTDRT)$_{1-10}$ (sADP5; SEQ ID NO:24)
(WP(A/S)TDKTKREEVD)$_{1-10}$ (ADP3; SEQ ID NO:7);
(PGYIN(L/F)SYE(K/N)SHSQAIN(T/V)DRTA)$_{1-10}$ (ADP5; SEQ ID NO:13);
(LPPLFSMPLSPILPELPLEAWPAT)$_{1-10}$ (ADP6; SEQ ID NO:17);
(HPP(S/T)HTLQPHHH(L/I)PVVPAQ QPV(A/I)PQQPMMPVPG(H/Q)HSMTP (T/I)QH)$_{1-10}$ (ADP7; SEQ ID NO:18); and
12-42 contiguous amino acids of (HPP(S/T)HTLQPHHH(L/I)PVVPAQ QPV(A/I)PQQPMMPVPG(H/Q)HSMTP(T/I)QH)$_{1-10}$ (ADP7; SEQ ID NO:18), or functional equivalents or combinations thereof; and
(b) one or more further formulations comprising at least one calcium ion source and/or at least one phosphate ion source;
wherein the first formulation is configured to release the polypeptide more rapidly than $Ca^{2+}$ is released from the at least one calcium ion source and $PO^{3-}$ is released from the at least one phosphate ion source.

In one embodiment, the first formulation has a reduced viscosity compared to the one or more further formulations. In another embodiment, the first formulation is tuned to modify aqueous solubility compared to the one or more further formulations. In a further embodiment, the calcium ion source is selected from the group consisting of calcium acetate, calcium carbonate, calcium citrate, calcium chloride, calcium gluconate, calcium glycerophosphate, calcium lactate, and calcium phosphate. In another embodiment, the phosphate ion source is selected from the group consisting of aluminum phosphates, calcium phosphates, potassium phosphates, and sodium phosphates. In one embodiment, a molar ratio of the at least one calcium ion source:the at least one phosphate ion source is about 5:3. In another embodiment, the molar ratio of polypeptide:combination of the at least one calcium ion source and the at least one phosphate ion source is about 1:2 to about 1:100.

In one embodiment, the one or more further formulations comprises a second formulation, wherein the first formulation and the second formulation are present in a lozenge or a gum. In another embodiment, the lozenge or gum comprises:
(i) a core region comprising the second formulation; and
(ii) a shell region comprising the first formulation.

In another embodiment, the one or more further formulations comprises a second formulation, wherein the second formulation is an aqueous formulation, and wherein the first formulation is an aqueous formulation. In another embodiment is disclosed a composition or kit comprising at least a first formulation comprising:
(a) an effective amount to treat a dental disorder and/or whiten teeth of a polypeptide comprising or consisting of the amino acid sequence selected from the group consisting of:
(SYENSHSQAINVDRT)$_{1-10}$ (shADP5; SEQ ID NO:16);
(SYEKSHSQAINTDRT)$_{1-10}$ (sADP5; SEQ ID NO:24)
(WP(A/S)TDKTKREEVD)$_{1-10}$ (ADP3; SEQ ID NO:7);
(PGYIN(L/F)SYE(K/N)SHSQAIN(T/V)DRTA)$_{1-10}$ (ADP5; SEQ ID NO:13);
(LPPLFSMPLSPILPELPLEAWPAT)$_{1-10}$ (ADP6; SEQ ID NO:17);
(HPP(S/T)HTLQPHHH(L/I)PVVPAQ QPV(A/I)PQQPMMPVPG(H/Q)HSMTP (T/I)QH)$_{1-10}$ (ADP7; SEQ ID NO:18); and
12-42 contiguous amino acids of (HPP(S/T)HTLQPHHH(L/I)PVVPAQ QPV(A/I)PQQPMMPVPG(H/Q)HSMTP(T/I)QH)$_{1-10}$ (ADP7; SEQ ID NO:18), or functional equivalents or combinations thereof; and
(b) at least one calcium ion source and or at least one phosphate ion source, wherein the at least one calcium ion source and the at least one phosphate ion source are encapsulated;

wherein at least first formulation is configured to release polypeptide at a faster rate than $Ca^{2+}$ and $PO_4^{3-}$. In one embodiment, the at least first formulation comprises a first formulation and a second formulation, wherein (i) the first formulation comprises the polypeptide and one of the at least one calcium ion source or at least one phosphate ion source; and (ii) the first formulation comprises the polypeptide and one of the at least one calcium ion source or at least one phosphate ion source;

wherein if the first formulation comprises the at least one calcium ion source then the second formulation comprises the at least one phosphate ion source, and if the first formulation comprises the at least one phosphate ion source then the second formulation comprises the at least one calcium ion source. In another embodiment, the at least one calcium ion source and the at least one phosphate ion source are encapsulated in phospholipid vesicles.

In one embodiment, the one or more further formulations comprises a second formulation, wherein the first formulation is present as a first adhesive gel layer and the second formulation is present in a second adhesive gel layer, wherein the second adhesive gel layer is adhered to the first adhesive gel layer directly or indirectly. In another embodiment, the one or more further formulations comprises a second formulation and a third formulation, wherein the second formulation comprises the one or more calcium ion sources and the third formulation comprises the one or more phosphate ion sources, wherein the first formulation is present as a first adhesive gel layer, the second formulation is present in a second adhesive gel layer, and the third formulation is present as a third adhesive gel layer, wherein the second adhesive gel layer and the third adhesive gel layer are adhered to the first adhesive gel layer directly or indirectly. In a further embodiment, the first adhesive gel layer, the second adhesive gel layer, and the third adhesive gel layer when present, are independently between 50 μm and 500 μm thick.

In one embodiment, the one or more further formulations comprise a second formulation and a third formulation, wherein the first, second, and third formulations are first, second, and third pastes and are each separated by a separation paste, wherein:

the first past comprises 10%-80%, 20%-75%, 30-70%, 40%-60%, 45%-55%, or about 47.5 to about 52.5% w/v of the polypeptide in buffer;

the second paste comprises 10%-80%, 20%-75%, 30-70%, 40%-60%, 45%-55%, or about 47.5 to about 52.5% w/v of the at least one calcium ion source, including but not limited to $CaCl_2$; and the third paste comprises 10%-80%, 20%-75%, 30-70%, 40%-60%, 45%-55%, or about 47.5 to about 52.5% w/v of the at least one phosphate ion source, including but not limited to $K_2HPO_4$; and wherein viscosity of the first paste is less than viscosity of the second paste and the third paste. In one embodiment, the first paste, the second paste, and the third paste comprises a thickener, including but not limited to polypropylene glycol (PPG), glycerol, and/or sodium carboxymethyl cellulose. In another embodiment, the first paste, the second paste, and the third paste comprise propylene glycol (PPG), glycerol, and sodium carboxymethyl cellulose (SCS), wherein the first paste comprises a higher concentration of PPG than the second paste and the third paste, and wherein the first paste comprises a lower concentration of SCS than the second paste or the third paste.

In various embodiments, the polypeptide comprises or consists of the amino acid sequence selected from the group consisting of:

(SYENSHSQAINVDRT)$_{1-10}$ (shADP5; SEQ ID NO:16), or a functional equivalent thereof;

(PGYINFSYENSHSQAINVDRTA)$_{1-10}$ (SEQ ID NO: 6) (ADP5H), or a functional equivalent thereof; and (SYEKSHSQAINTDRT)$_{1-10}$ (sADP5; SEQ ID NO:24), or a functional equivalent thereof;

(HTLQPHHH(L/I)PVV)$_{1-10}$ (ADP1; SEQ ID NO:1);

(VPG(H/Q)HSMTP(T/I)QH)$_{1-10}$ (ADP2; SEQ ID NO:4);

(HPP(S/T)HTLQPHHH(L/I)PVV)$_{1-10}$ (ADP4; SEQ ID NO:10);

(PAQQPV(A/I)PQQPMMP)$_{1-10}$ (ADP8; SEQ ID NO:21);

(HPP(S/T)HTLQPHHH(L/I)PVVPAQQPV(A/I) PQQPMMPVPG(H/Q)HSMTP (T/I)QH)$_{1-10}$ (ADP7; SEQ ID NO:18);

HTLQPHHHLPVV)$_{1-10}$ (ADP1M; SEQ ID NO:2);

(HTLQPHHHIPVV)$_{1-10}$ (ADP1H; SEQ ID NO:3);

(VPGHHSMTPTQH)$_{1-10}$ (ADP2M; SEQ ID NO:5);

(VPGQHSMTPIQH)$_{1-10}$ (ADP2H; SEQ ID NO:14);

(HPPSHTLQPHHHLPVV)$_{1-10}$ (ADP4M; SEQ ID NO:11);

(HPPTHTLQPHHHIPVV)$_{1-10}$ (ADP4H; SEQ ID NO:12);

(HPPSHTLQPHHHLPVVPAQQPVAPQQPMMPVPG-HHSMTPTQH)$_{1-10}$ (ADP7M; SEQ ID NO:19);

(HPPTH-TLQPHHHIPVVPAQQPVIPQQPMMPVPGQHSMT-PIQH)$_{1-10}$ (ADP7H; SEQ ID NO:20);

(PAQQPVAPQQPMMP)$_{1-10}$ (ADP8M; SEQ ID NO:22); and (PAQQPVIPQQPMMP)$_{1-10}$ (ADP8H; SEQ ID NO:23);

(WPATDKTKREEVD)$_{1-10}$ (ADP3M; SEQ ID NO:8);

(WPSTDKTKREEVD)$_{1-10}$ (ADP3H; SEQ ID NO:9),

MLPHHGA (HABP1; SEQ ID NO:25); and

NPGFAQA (HABP2; SEQ ID NO:26);

or a functional equivalent thereof, or a combination thereof.

In another aspect, the disclosure provides methods for treating a dental disorder, whitening teeth, restoring and retaining the tooth structure, and/or restoring the mineral content of tooth-mineral loss due to demineralization, comprising orally administering to a subject in need thereof:

(a) a first formulation comprising an effective amount to treat a dental disorder and/or whiten teeth of a polypeptide comprising or consisting of the amino acid sequence selected from the group consisting of:

(SYENSHSQAINVDRT)$_{1-10}$ (shADP5; SEQ ID NO:16);

(SYEKSHSQAINTDRT)$_{1-10}$ (sADP5; SEQ ID NO:24)

(WP(A/S)TDKTKREEVD)$_{1-10}$ (ADP3; SEQ ID NO:7);

(PGYIN(L/F)SYE(K/N)SHSQAIN(T/V)DRTA)$_{1-10}$ (ADP5; SEQ ID NO:13);

(LPPLFSMPLSPILPELPLEAWPAT)$_{1-10}$ (ADP6; SEQ ID NO:17);

(HPP(S/T)HTLQPHHH(L/I)PVVPAQ QPV(A/I) PQQPMMPVPG(H/Q)HSMTP (T/I)QH)$_{1-10}$ (ADP7; SEQ ID NO:18); and 12-42 contiguous amino acids of (HPP(S/T)HTLQPHHH (L/I)PVVPAQ QPV(A/I)PQQPMMPVPG(H/Q) HSMTP(T/I)QH)$_{1-10}$ (ADP7; SEQ ID NO:18), or functional equivalents or combinations thereof; and (b) one or more further formulations comprising at least one calcium ion source and/or at least one phosphate ion source;

wherein the first formulation is administered to the subject such that the polypeptide is accessible to one or more teeth of the subject prior to $Ca^{2+}$ released from the at least one calcium ion source and $PO_4^{3-}$ released from the at least one phosphate ion source.

In one embodiment, the first formulation has a reduced viscosity compared to the one or more further formulations. In another embodiment, the first formulation is tuned to modify aqueous solubility compared to the one or more further formulations. In a further embodiment, the calcium ion source is selected from the group consisting of calcium acetate, calcium carbonate, calcium citrate, calcium chloride, calcium gluconate, calcium glycerophosphate, calcium lactate, and calcium phosphate. In another embodiment, the phosphate ion source is selected from the group consisting of aluminum phosphates, calcium phosphates, potassium phosphates, and sodium phosphates. In one embodiment, a molar ratio of the at least one calcium ion source:the at least one phosphate ion source is about 5:3. In another embodiment, the molar ratio of polypeptide:combination of the at least one calcium ion source and the at least one phosphate ion source is about 1:2 to about 1:100.

In one embodiment, the one or more further formulations comprises a second formulation, wherein the first formulation and the second formulation are present in a lozenge or a gum. In another embodiment, the lozenge or gum comprises:

(i) a core region comprising the second formulation; and
(ii) a shell region comprising the first formulation.

In another embodiment, the one or more further formulations comprises a second formulation, wherein the second formulation is an aqueous formulation, and wherein the first formulation is an aqueous formulation. In another embodiment is disclosed a composition or kit comprising at least a first formulation comprising:

(a) an effective amount to treat a dental disorder, whiten teeth, restore and retain the tooth structure, and/or restore the mineral content of tooth-mineral loss due to demineralization, of a polypeptide comprising or consisting of the amino acid sequence selected from the group consisting of:
(SYENSHSQAINVDRT)$_{1-10}$ (shADP5; SEQ ID NO:16);
(SYEKSHSQAINTDRT)$_{1-10}$ (sADP5; SEQ ID NO:24)
(WP(A/S)TDKTKREEVD)$_{1-10}$ (ADP3; SEQ ID NO:7);
(PGYIN(L/F)SYE(K/N)SHSQAIN(T/V)DRTA)$_{1-10}$ (ADP5; SEQ ID NO:13);
(LPPLFSMPLSPILPELPLEAWPAT)$_{1-10}$ (ADP6; SEQ ID NO:17);
(HPP(S/T)HTLQPHHH(L/I)PVVPAQ QPV(A/I) PQQPMMPVPG(H/Q)HSMTP (T/I)QH)$_{1-10}$ (ADP7; SEQ ID NO:18); and
12-42 contiguous amino acids of (HPP(S/T)HTLQPHHH (L/I)PVVPAQ QPV(A/I)PQQPMMPVPG(H/Q) HSMTP(T/I)QH)$_{1-10}$ (ADP7; SEQ ID NO:18), or functional equivalents or combinations thereof; and (b) at least one calcium ion source and or at least one phosphate ion source, wherein the at least one calcium ion source and the at least one phosphate ion source are encapsulated;

wherein at least first formulation is configured to release polypeptide at a faster rate than $Ca^{2+}$ and $PO_4^{3-}$. In one embodiment, the at least first formulation comprises a first formulation and a second formulation, wherein (i) the first formulation comprises the polypeptide and one of the at least one calcium ion source or at least one phosphate ion source; and (ii) the first formulation comprises the polypeptide and one of the at least one calcium ion source or at least one phosphate ion source;

wherein if the first formulation comprises the at least one calcium ion source then the second formulation comprises the at least one phosphate ion source, and if the first formulation comprises the at least one phosphate ion source then the second formulation comprises the at least one calcium ion source. In another embodiment, the at least one calcium ion source and the at least one phosphate ion source are encapsulated in phospholipid vesicles.

In one embodiment, the one or more further formulations comprises a second formulation, wherein the first formulation is present as a first adhesive gel layer and the second formulation is present in a second adhesive gel layer, wherein the second adhesive gel layer is adhered to the first adhesive gel layer directly or indirectly. In another embodiment, the one or more further formulations comprises a second formulation and a third formulation, wherein the second formulation comprises the one or more calcium ion sources and the third formulation comprises the one or more phosphate ion sources, wherein the first formulation is present as a first adhesive gel layer, the second formulation is present in a second adhesive gel layer, and the third formulation is present as a third adhesive gel layer, wherein the second adhesive gel layer and the third adhesive gel layer are adhered to the first adhesive gel layer directly or indirectly. In a further embodiment, the first adhesive gel layer, the second adhesive gel layer, and the third adhesive gel layer when present, are independently between 50 μm and 500 μm thick.

In one embodiment, the one or more further formulations comprise a second formulation and a third formulation, wherein the first, second, and third formulations are first, second, and third pastes and are each separated by a separation paste, wherein:

the first past comprises 10%-80%, 20%-75%, 30-70%, 40%-60%, 45%-55%, or about 47.5 to about 52.5% w/v of the polypeptide in buffer;

the second paste comprises 10%-80%, 20%-75%, 30-70%, 40%-60%, 45%-55%, or about 47.5 to about 52.5% w/v of the at least one calcium ion source, including but not limited to $CaCl_2$; and the third paste comprises 10%-80%, 20%-75%, 30-70%, 40%-60%, 45%-55%, or about 47.5 to about 52.5% w/v of the at least one phosphate ion source, including but not limited to $K_2HPO_4$; and wherein viscosity of the first paste is less than viscosity of the second paste and the third paste. In one embodiment, the first paste, the second paste, and the third paste comprises a thickener, including but not limited to polypropylene glycol (PPG), glycerol, and/or sodium carboxymethyl cellulose. In another embodiment, the first paste, the second paste, and the third paste comprise propylene glycol (PPG), glycerol, and sodium carboxymethyl cellulose (SCS), wherein the first paste comprises a higher concentration of PPG than the second paste and the third paste, and wherein the first paste comprises a lower concentration of SCS than the second paste or the third paste.

In various embodiments, the polypeptide comprises or consists of the amino acid sequence selected from the group consisting of:
(SYENSHSQAINVDRT)$_{1-10}$ (shADP5; SEQ ID NO:16), or a functional equivalent thereof;
(PGYINFSYENSHSQAINVDRTA)$_{1-10}$ (SEQ ID NO: 6) (ADP5H), or a functional equivalent thereof; and (SYEKSHSQAINTDRT)$_{1-10}$ (sADP5; SEQ ID NO:24), or a functional equivalent thereof;
(HTLQPHHH(L/I)PVV)$_{1-10}$ (ADP1; SEQ ID NO:1);
(VPG(H/Q)HSMTP(T/I)QH)$_{1-10}$ (ADP2; SEQ ID NO:4);
(HPP(S/T)HTLQPHHH(L/I)PVV)$_{1-10}$ (ADP4; SEQ ID NO:10);
(PAQQPV(A/I)PQQPMMP)$_{1-10}$ (ADP8; SEQ ID NO:21);
(HPP(S/T)HTLQPHHH(L/I)PVVPAQQPV(A/I)PQQPMMPVPG(H/Q)HSMTP (T/I)QH)$_{1-10}$ (ADP7; SEQ ID NO:18);
HTLQPHHHLPVV)$_{1-10}$ (ADP1M; SEQ ID NO:2);
(HTLQPHHHIPVV)$_{1-10}$ (ADP1H; SEQ ID NO:3);
(VPGHHSMTPTQH)$_{1-10}$ (ADP2M; SEQ ID NO:5);
(VPGQHSMTPIQH)$_{1-10}$ (ADP2H; SEQ ID NO:14);
(HPPSHTLQPHHHLPVV)$_{1-10}$ (ADP4M; SEQ ID NO:11);
(HPPTHTLQPHHHIPVV)$_{1-10}$ (ADP4H; SEQ ID NO:12);
(HPPSHTLQPHHHLPVVPAQQPVAPQQPMMPVPG-HHSMTPTQH)$_{1-10}$ (ADP7M; SEQ ID NO:19);
(HPPTH-TLQPHHHIPVVPAQQPVIPQQPMMPVPGQHSMT-PIQH)$_{1-10}$ (ADP7H; SEQ ID NO:20);
(PAQQPVAPQQPMMP)$_{1-10}$ (ADP8M; SEQ ID NO:22); and
(PAQQPVIPQQPMMP)$_{1-10}$ (ADP8H; SEQ ID NO:23);
(WPATDKTKREEVD)$_{1-10}$ (ADP3M; SEQ ID NO:8);
(WPSTDKTKREEVD)$_{1-10}$ (ADP3H; SEQ ID NO:9),
MLPHHGA (HABP1; SEQ ID NO:25); and
NPGFAQA (HABP2; SEQ ID NO:26);
or a functional equivalent thereof, or a combination thereof.

In another embodiment, the subject is suffering from a dental disorder selected from the group consisting of periodontitis, tooth erosion, hypersensitivity, bacterial plaque, dental fluorosis, tooth decay, carries, tooth resorption, craniomaxillofacial bone disease, gingival recession, and/or demineralization of enamel of one or more tooth.

DETAILED DESCRIPTION

Figure 1:
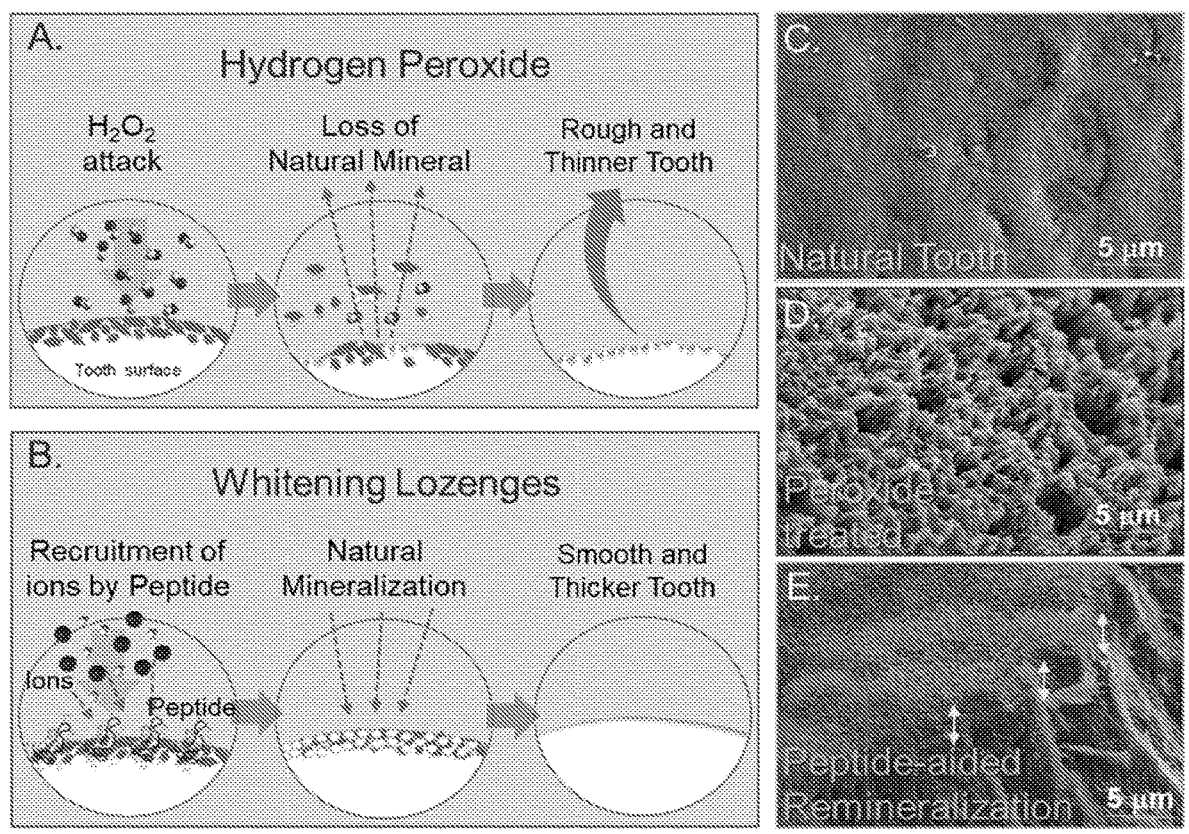
FIG. 1. Schematics of Mechanisms of Action of (A) Hydrogen peroxide-based whitening products vs (B) Whitening lozenges. Representative scanning electron microscopy images of (C) Natural tooth, (D) Hydrogen peroxide and (E) Lozenge treated surfaces. Normally the surface of the tooth is somewhat rough but generally smooth from mastication actions (C). The surface of the tooth is highly rough because of the chemical etching action of the hydrogen peroxide-based gels and strips that remove substantial mineral from the surface of the tooth (D). Because of the additive mechanism of action of the peptide-guided remineralization, the tooth surface in covered with a new mineral when lozenge is used (E).

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991.

Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, "about" means +/−5% of the recited parameter.

All embodiments of any aspect of the invention can be used in combination, unless the context clearly dictates otherwise.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure.

These and other changes can be made to the disclosure in light of the detailed description. Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In a first aspect, the disclosure provides compositions or kits comprising (a) a first formulation comprising an effective amount to treat a dental disorder, whiten teeth, restore and retain tooth structure, and/or restore the mineral content of tooth-mineral loss due to demineralization, of a polypeptide comprising or consisting of the amino acid sequence selected from the group consisting of:

(SYENSHSQAINVDRT)$_{1-10}$ (shADP5; SEQ ID NO:16);
(SYEKSHSQAINTDRT)$_{1-10}$ (sADP5; SEQ ID NO:24)
(WP(A/S)TDKTKREEVD)$_{1-10}$ (ADP3; SEQ ID NO:7);
(PGYIN(L/F)SYE(K/N)SHSQAIN(T/V)DRTA)$_{1-10}$ (ADP5; SEQ ID NO:13);
(LPPLFSMPLSPILPELPLEAWPAT)$_{1-10}$ (ADP6; SEQ ID NO:17);
(HPP(S/T)HTLQPHHH(L/I)PVVPAQ QPV(A/I)PQQPMMPVPG(H/Q)HSMTP (T/I)QH)$_{1-10}$ (ADP7; SEQ ID NO:18); and
12-42 contiguous amino acids of (HPP(S/T)HTLQPHHH(L/I)PVVPAQ QPV(A/I)PQQPMMPVPG(H/Q)HSMTP(T/I)QH)$_{1-10}$ (ADP7; SEQ ID NO:18), or functional equivalents or combinations thereof; and (b) one or more further formulations comprising at least one calcium ion source and/or at least one phosphate ion source;

wherein the first formulation is configured to release the polypeptide more rapidly than $Ca^{2+}$ is released from the at least one calcium ion source and $PO_4^{3-}$ is released from the at least one or more further formulations.

As disclosed herein the inventors have surprisingly discovered that if mineralization peptides and calcium/phosphate ions are administered together to a subject, mineralization initiates within the saliva such that mineralization is initiated away from the tooth surface, severely limiting the mineralization efficacy on dental tissues. The compositions and method of the present disclosure provide a significant improvement over prior methods by focusing all mineralization at the tooth surface. The polypeptide is released first and adheres to one or more teeth of the subject, while the release ions later migrate to the tooth to initiate mineralization.

The first formulation is configured to release the polypeptide more rapidly than $Ca^{2+}$ is released from the at least one calcium ion source and $PO_4^{3-}$ is released from the at least one or more further formulations. Such release profile may be established by any suitable means. In one embodiment, the first formulation has a reduced viscosity compared to the one or more further formulations. In another embodiment, the first formulation is tuned to modify aqueous solubility compared to the one or more further formulations.

The first formulation and the one or more further formulations may be of any suitable type, including but not limited to components of toothpaste, toothpowders, mouthwash, dental floss, liquid dentifrices, dental tablets, topical gels, troches, chewing gums, dental pastes, gingival massage creams, gargle tablets, lozenges, and food products. Non-limiting specific embodiments are described in more detail herein.

Any suitable calcium ion source may be used that can act as a precursor to calcium ions. In various non-limiting embodiments, the calcium ion source is selected from the group consisting of calcium acetate, calcium carbonate, calcium citrate, calcium chloride, calcium gluconate, calcium glycerophosphate, calcium lactate, and calcium phosphate. The calcium ion source may be present in the one or more further formulations at any concentration suitable for an intended use. In various non-limiting embodiments, the one or more further formulations comprise the at least one calcium ion source at a concentration ranging between about 1 mM and about 10 M, 1 mM and about 5 M, 1 mM and about 2 M, between about 1 mM and about 1M, between about 1 mM and about 0.5M, between about 1 mM and about 100 mM, between about 1 mM and about 50 mM, between about 1 mM and about 10 mM, between about 2 mM and about 8 mM, between about 3 mM and about 7 mM, between about 4 mM and about 6 mM, or between about 4.5 mM and about 5.5 mM.

Any suitable phosphate ion source may be used that can act as a precursor to phosphate ions. In various non-limiting embodiments, the phosphate ion source is selected from the group consisting of aluminum phosphates, calcium phosphates, potassium phosphates, and sodium phosphates. The phosphate ion source may be present in the one or more further formulations at any concentration suitable for an intended use. In various non-limiting embodiments, the one or more further formulations comprise the at least one phosphate ion source at a concentration ranging between about 1 mM and about 10 M, 1 mM and about 5 M, 1 mM and about 2 M, between about 1 mM and about 1M, between about 1 mM and about 0.5M, between about 1 mM and about 100 mM, between about 1 mM and about 50 mM, between about 1 mM and about 10 mM, between about 1 mM and about 7 mM, or between about 1 mM and about 6 mM, between about 1.5 mM and about 5 mM, between about 2 mM and about 4 mM, or between about 2.5 mM and about 3.5 mM.

In one embodiment, a molar ratio of the at least one calcium ion source to the at least one phosphate ion source is about 5:3 in the one or more further formulations. In another embodiment, the molar ratio of polypeptide in the first formulation to the combination of the at least one calcium ion source and the at least one phosphate ion source in the one or more further formulations is about 1:2 to about 1:100, about 1:2 to about 1:50, about 1:2 to about 1:25, about 1:2 to about 1:10, about 1:10 to about 1:100, about 1:10 to about 1:50, or about 1:2, about 1:10, or about 1:100.

In one embodiment, the one or more further formulations comprises a second formulation, wherein the first formulation and the second formulation are present in a lozenge. The lozenge may take any suitable form. In one embodiment, the lozenge comprises:
 (i) a core region comprising the second formulation; and
 (ii) a shell region comprising the first formulation.

Upon oral administration to a subject, the shell region dissolves in the saliva and the polypeptides are released and deposited onto teeth. After the shell region is dissolved, the core region supplies calcium and phosphate ions to initiate biomineralization at the tooth surface. The lozenge may be any size or shape suitable for oral administration to a subject, including but not limited to cylindrical, square, rectangular, etc. In one embodiment, the lozenge may comprise a cylindrical tablet between about 6 mm-15 mm in diameter and about 2 mm-4 mm thickness.

In one embodiment, the second formulation comprises:
 (A) between 0.1%-80%, 0.5%-80%, 1%-80%, 5%-80%, 10%-80%, 20%-75%, 30-70%, 40%-65%, 45%-60%, 50%-60%, 52%-58%, 53%-57%, 54%-56%, or about 54-55% w/w calcium ion source, including but not limited to $CaCl_2 \cdot H_2O$; and
 (B) between 0.1%-80%, 0.5%-80%, 1%-80%, 5%-80%, 10%-80%, 10%-60%, 15%-50%, 20%-40%, 25%-35%, 27%-33%, 28%-32%, 29%-31%, or about 29.5%-30.5% w/w potassium ion source, including but not limited to $KH_2PO_4$.

In another embodiment, the second formulation further comprises one or more lubricants, flavoring agents, and/or excipients. In a still further embodiment, the second formulation comprises:
 between 0.1%-80%, 0.5%-80%, 1%-80%, 5%-80%, 10%-80%, 20%-75%, 30-70%, 40%-65%, 45%-60%, 50%-60%, 52%-58%, 53%-57%, 54%-56%, or about 54-55% w/w $CaCl_2 \cdot H_2O$;
 between 0.1%-80%, 0.5%-80%, 1%-80%, 5%-80%, 10%-80%, 10%-60%, 15%-50%, 20%-40%, 25%-35%, 27%-33%, 28%-32%, 29%-31%, or about 29.5%-30.5% w/w $KH_2PO_4$; and
 between 1%-10% w/w lubricant.

In a further embodiment, the first formulation comprises between 0.1%-10%, 0.5%-7.5%, 1%-6%, 1.5%-5%, 2%-4%, or about 2.5% to about 3.5% w/w of the polypeptide. In another embodiment, the first formulation further comprises one or more lubricant, flavoring agent, and/or filler. In one embodiment, the first formulation comprises:
 0.1%-10%, 0.5%-7.5%, 1%-6%, 1.5%-5%, 2%-4%, or about 2.5% to about 3.5% w/w of the polypeptide
 1%-10% w/w lubricant; and
 50% to 90% w/w.

In one embodiment, the lozenge may comprise the ingredients listed in Table 1A.

TABLE 1A

Exemplary ingredients contained in the whitening lozenge

| Ingredients | Lozenge Shell Region | | Lozenge Core Region | |
|---|---|---|---|---|
| | Amount (mg) | Weight % | Amount (mg) | Weight % |
| Peptide | 0.1-10 | 0.1-10 | 0 | 0 |
| $CaCl_2 \cdot H_2O$ | 0-20 | 0.1-10 | 17-134 | 10-80 |
| $KH_2PO_4$ | 0-20 | 0.1-10 | 17-102 | 10-60 |
| Lubricant (including but not limited to Mg-Stearate, calcium stearate (Ca-stearate), stearic acid, and/or non-hydrogenated vegetable oil powder) | 1-10 | 1-10 | 1.7-17 | 1-10 |
| Sweeteners (any suitable flavoring agent including but not limited to D-sorbitol, xylitol, mint and/or other types of plant-based flavoring agents) | 1-30 | 1-30 | 1.7-51 | 1-30 |
| Excipients (including but not limited to lactose, menthol, etc.) | 50-80 | 50-80 | 0-134 | 0-80 |
| Total | 100 | 100 | 170 | 100 |

The lozenges may be prepared using any suitable techniques, including but not limited to the techniques described herein. In one non-limiting embodiment, lozenges can be manufactured by compressing the blended ingredients within metal dies using hydraulic press machines under a compression force. Further non-limiting lozenge embodiments are provided in the examples that follow.

Similar to the lozenge, a layered gum can be prepared that has two components: one containing the peptide and the other the two ions. The two layers may the same structural and physical characteristics. The thickness of the two layers may be the same. The viscosity and the chemical and mechanical stabilities of the two components may also the same, meaning the inactive components are similar. Under the mastication action, two active components mix, each dissolving in saliva. Upon immobilization on the tooth surface, the peptide recruits the ions and causes the remineralization. Each gum has a certain lifetime, during which the ions and the peptide continuously released from the gum, but at a decreasing rate, dissolving in the saliva and remineralizing on the surface of the teeth.

The gum has a core-shell architecture similar to the lozenge, with the shell is the peptide that may comprise a hard shell, similar to that described in embodiments that cover lozenge, and a gum core containing the calcium ion source and the phosphate ion source. The sequential release of peptide then calcium and phosphate ions is accomplished by dissolution of the shell in the mouth without chewing until the gum core is exposed. Follow-up release of the calcium and phosphate ions is accomplished by chewing. The ingredients in each region of the gum may be the same as those in Table 1A. In a specific embodiment, the ingredients may be as listed in Table 1B.

TABLE 1B

| Ingredients | Hard Shell Region | | Gum Core Region | |
|---|---|---|---|---|
| | Amount (mg) | Weight % | Amount (mg) | Weight % |
| Peptide | 1 | 1 | 0 | 0 |
| $CaCl_2 \cdot H_2O$ | 0 | 0 | 24 | 24 |
| $KH_2PO_4$ | 0 | 0 | 14.4 | 14.4 |
| Lubricant (including but not limited to Mg-Stearate, calcium stearate (Ca-stearate), stearic acid, and/or non-hydrogenated vegetable oil powder) | 2 | 2 | 2 | 2 |
| Sweeteners (any suitable flavoring agent including but not limited to D-sorbitol, xylitol, mint and/or other types of plant-based flavoring agents) | 20 | 20 | 10 | 10 |
| Excipients (including but not limited to lactose, menthol, etc.) | 77 | 77 | 0 | 0 |
| Gum base granules/powder (including but not limited to chicle, gutta percha, paraffin) | | | 47.6 | 47.6 |
| Softener (including but not limited to vegetable oil) | | | 2 | 2 |
| Total | 100 | 100 | 100 | 100 |

In one embodiment, the gum core may be fabricated by pressing at 7000 psi the dry ingredients listed in the tables above. The hard shell consisting the powder blend listed in the table may then be coated around the gum core and pressed at 9000 psi. The resulting hard shell-gum core architecture may, for example, have dimensions of 8 mm core diameter and 10 mm overall with shell layer.

TABLE 1C

Exemplary ingredients contained in the whitening chewing gum

| Ingredients | Hard Shell Region | | Gum Core Region | |
|---|---|---|---|---|
| | Amount (mg) | Weight % | Amount (mg) | Weight % |
| Peptide | 0.1-10 | 0.1-10 | 0 | 0 |
| $CaCl_2 \cdot H_2O$ | 0-20 | 0.1-10 | 17-134 | 10-80 |
| $KH_2PO_4$ | 0-20 | 0.1-10 | 17-102 | 10-60 |
| Lubricant (including but not limited to Mg-Stearate, calcium stearate (Ca-stearate), stearic acid, and/or non-hydrogenated vegetable oil powder) | 1-10 | 1-10 | 1.7-17 | 1-10 |

TABLE 1C-continued

Exemplary ingredients contained in the whitening chewing gum

| Ingredients | Hard Shell Region | | Gum Core Region | |
|---|---|---|---|---|
| | Amount (mg) | Weight % | Amount (mg) | Weight % |
| Sweeteners (any suitable flavoring agent including but not limited to D-sorbitol, xylitol, mint and/or other types of plant-based flavoring agents) | 1-30 | 1-30 | 1.7-51 | 1-30 |
| Excipients (including but not limited to lactose, menthol, etc.) | 50-80 | 50-80 | 0-134 | 0-80 |
| Gum base granules/powder (including but not limited to chicle, gutta percha, paraffin) | | | 0-120 | 0-50 |
| Softener (including but not limited to vegetable oil) | | | 0-10 | 0-5 |
| Total | 100 | 100 | 100 | 100 |

In another embodiment, the one or more further formulations comprise a second formulation, wherein the second formulation is an aqueous formulation, and wherein the first formulation is an aqueous formulation. In this embodiment, the first and second formulations may comprise a mouthwash provided in separate containers. In contact with saliva, the polypeptide binds teeth and recruits ions present in the second formulation to remineralize the teeth surface.

In an alternative mouthwash design, the composition or kit comprises at least a first formulation comprising:

(a) an effective amount to treat a dental disorder, whiten teeth, restore and retain the tooth structure, and/or restore the mineral content of tooth-mineral loss due to demineralization, of a polypeptide comprising or consisting of the amino acid sequence selected from the group consisting of:
$(SYENSHSQAINVDRT)_{1-10}$ (shADP5; SEQ ID NO:16);
$(SYEKSHSQAINTDRT)_{1-10}$ (sADP5; SEQ ID NO:24)
$(WP(A/S)TDKTKREEVD)_{1-10}$ (ADP3; SEQ ID NO:7);
$(PGYIN(L/F)SYE(K/N)SHSQAIN(T/V)DRTA)_{1-10}$ (ADP5; SEQ ID NO:13);
$(LPPLFSMPLSPILPELPLEAWPAT)_{1-10}$ (ADP6; SEQ ID NO:17);
$(HPP(S/T)HTLQPHHH(L/I)PVVPAQ\ QPV(A/I)PQQPMMPVPG(H/Q)HSMTP\ (T/I)QH)_{1-10}$ (ADP7; SEQ ID NO:18); and
12-42 contiguous amino acids of $(HPP(S/T)HTLQPHHH(L/I)PVVPAQ\ QPV(A/I)PQQPMMPVPG(H/Q)HSMTP(T/I)QH)_{1-10}$ (ADP7; SEQ ID NO:18), or functional equivalents or combinations thereof; and (b) at least one calcium ion source and or at least one phosphate ion source, wherein the at least one calcium ion source and the at least one phosphate ion source are encapsulated;

wherein at least first formulation is configured to release polypeptide at a faster rate than $Ca^{2+}$ and $PO_4^{3-}$.

In one embodiment of this alternative design, he at least first formulation comprises a first formulation and a second formulation, wherein (i) the first formulation comprises the polypeptide and one of the at least one calcium ion source or at least one phosphate ion source; and (ii) the first formulation comprises the polypeptide and one of the at least one calcium ion source or at least one phosphate ion source;

wherein if the first formulation comprises the at least one calcium ion source then the second formulation comprises the at least one phosphate ion source, and if the first formulation comprises the at least one phosphate ion source then the second formulation comprises the at least one calcium ion source.

In this alternative embodiment, the at least one calcium ion source and the at least one phosphate ion source may be encapsulated in vesicles, including but not limited to phospholipid. micelle, lipid, liposomal, or peptide vesicles to delay release relative to the polypeptide. Any suitable phospholipid vesicle may be used, including but not limited to polydiacetylene-phospholipid vesicles. The vesicles may be of any suitable size, including but not limited to having a diameter of between about 100 nm and-about 10 µm.

Figure 22:
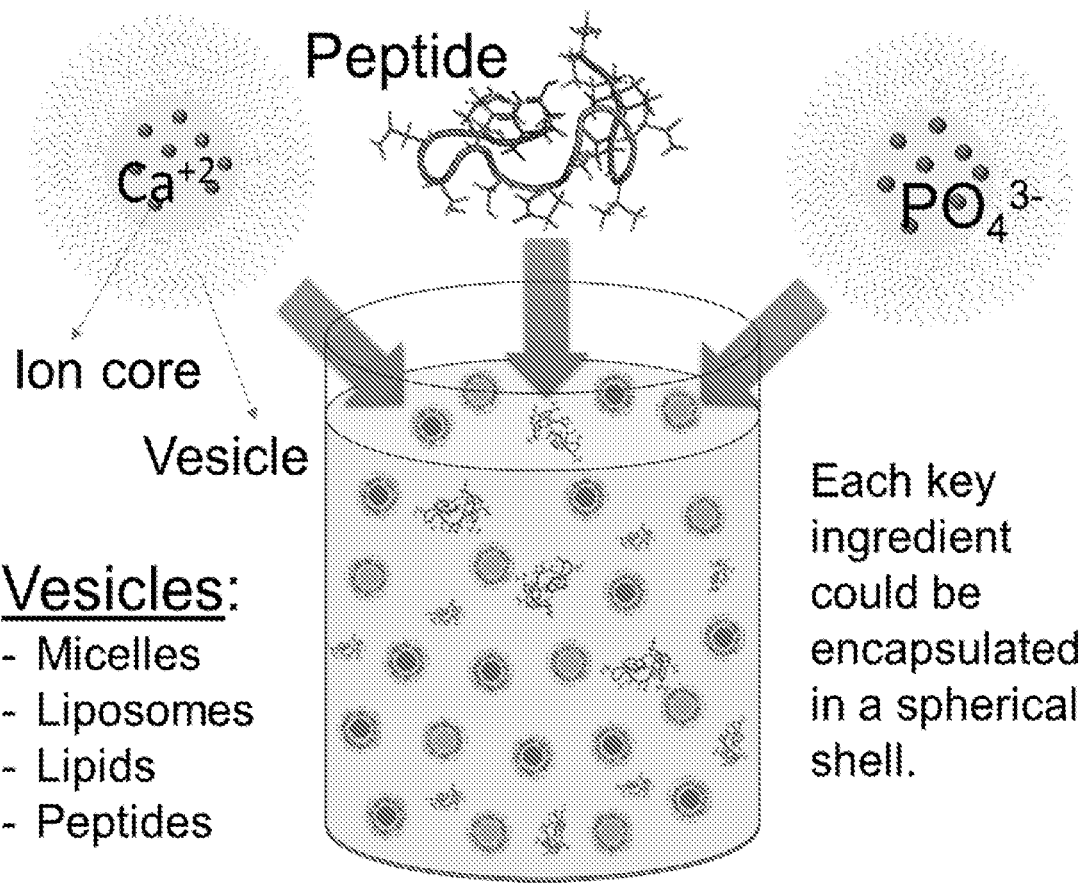
FIG. 22. Schematic representation of an exemplary mouthwash of the disclosure.

In this alternative mouthwash design, calcium and phosphate precursors are encapsulated within cationic and anionic neutral pH-response vesicles and kept separate and stable during the storage. Moreover, sequencing delivery of peptide and precursor ions is established by adjusting the ionic characters of the head groups of the vesicles to provide delayed release upon contact with saliva. See, for example, FIG. 22.

In one embodiment of the mouthwash design, the first formulation or the second formulation comprises:

(A) 0.1%-80%, 0.5%-80%, 1%-80%, 5%-80%, 10%-80%, 20%-80%, 30-80%, 40%-80%, 45%-80%, 50%-80%, 60%-78%, 65%-75%, or about 67.5%-72.5% w/w calcium ion source, including but not limited to $CaCl_2 \cdot H_2O$; and/or (B) 0.1%-80%, 0.5%-80%, 1%-80%, 5%-80%, 10%-80%, 10%-60%, 15%-50%, 20%-40%, 25%-35%, 27%-33%, 28%-32%, 29%-31%, or about 29.5%-30.5% w/w potassium ion source, including but not limited to $KH_2PO_4$.

In another embodiment of the mouthwash design, the first formulation and/or the second formulation further comprises one or more preservatives, flavoring agents, and/or antimicrobials. In a further embodiment, the polypeptide is present in the first formulation and/or the second formulation at a concentration of between about 100 ng/ml, 1 mg/ml and about 100 mg/ml, about 10 mg/ml and about 90 mg/ml, about 20 mg/ml and about 80 mg/ml, about 30 mg/ml and about 70 mg/ml, about 35 mg/ml and about 65 mg/ml, about 35 mg/ml and about 60 mg/ml, or about 40 mg/ml and about 50 mg/ml.

The first and/or second formulations of these mouthwash embodiments are aqueous and may contain any other suitable ingredients/excipients as deemed appropriate, including but not limited to preservatives, flavoring agents, etc. In non-limiting embodiments, the mouthwash embodiment comprises ingredients listed in Tables 2A-B.

TABLE 2A

Exemplary ingredients contained in the mouthwash embodiments.

| Ingredients | Mouth Wash Formula (First formulation) | | Mouth Wash Formula (Second formulation) | |
|---|---|---|---|---|
| | Amount (mg) | Weight to Volume % | Amount (mg) | Weight to Volume % |
| Peptide | 0.01-10 | 0.1-10 | 0 | 0 |
| $CaCl_2 \cdot H_2O$ | 17-134 | 10-80 | 0 | 0 |
| $KH_2PO_4$ | 0 | 0 | 17-102 | 10-60 |
| $KHPO_4$ | 0 | 0 | 17-102 | 10-60 |
| Preservatives | 0.1-10 | 0.1-10 | 0.17-17 | 0.1-10 |
| Sweeteners (any suitable flavoring agent including but not limited to D-sorbitol, xylitol, mint and/or other types of plant-based flavoring agents) | 0.1-30 | 0.1-30 | 0.17-51 | 0.1-30 |
| Antimicrobial Plant Extracts | 0.1-30 | 0.1-30 | 0.17-51 | 0.1-30 |
| Water | 50-80 | 50-80 | 0-134 | 0-80 |

TABLE 2B

Exemplary ingredients contained in the mouthwash embodiments.

| Ingredients | Mouth Wash Formula (First formulation) | | Mouth Wash Formula (Second formulation) | |
|---|---|---|---|---|
| | Amount (mg) | Weight to Volume % | Amount (mg) | Weight to Volume % |
| Peptide | 0.01-10 | 0.1-10 | 0 | 0 |
| Vesicle containing ionic Ca | 0 | 0 | 17-134 | 10-80 |
| Vesicle containing ionic $PO_4$ | 0 | 0 | 17-102 | 10-60 |
| Preservatives | 0.1-10 | 0.1-10 | 0.17-17 | 0.1-10 |
| Sweeteners (any suitable flavoring agent including but not limited to D-sorbitol, xylitol, mint and/or other types of plant-based flavoring agents) | 0.1-30 | 0.1-30 | 0.17-51 | 0.1-30 |
| Antimicrobial Plant Extracts | 0.1-30 | 0.1-30 | 0.17-51 | 0.1-30 |
| Water | 50-80 | 50-80 | 0-134 | 0-80 |

In another embodiment, the one or more further formulations comprises a second formulation, wherein the first formulation is present as a first adhesive gel layer and the second formulation is present in a second adhesive gel layer, wherein the second adhesive gel layer is adhered to the first adhesive gel layer directly or indirectly. In a related embodiment, the one or more further formulations comprises a second formulation and a third formulation, wherein the second formulation comprises the one or more calcium ion sources and the third formulation comprises the one or more phosphate ion sources, wherein the first formulation is present as a first adhesive gel layer, the second formulation is present in a second adhesive gel layer, and the third formulation is present as a third adhesive gel layer, wherein the second adhesive gel layer and the third adhesive gel layer are adhered to the first adhesive gel layer directly or indirectly.

In these embodiments, the first and second, or first, second, and third formulations form dental strips. The strips have self-adhesive properties. The strips are durable within the saliva but leaky allowing the ions in one and the peptide in the other to be released from the strips and mix to form the remineralizing layer on the surface of the teeth. The thickness of the strip is designed to allow a certain concentration of the ions and the peptides to facilitate the formation of remineralized layer with a predetermined thickness at the site of the application to the teeth surface. The strips are flexible to be bent over the tooth edge covering both the facing surface as well as the inside surface. The strips have mineralizing as well as penetration capability into the exposed dental tubules, to treat dental hypersensitivity. In one embodiment, the first adhesive gel layer, the second adhesive gel layer, and the third adhesive gel layer when present, are independently between 50 µm and 500 µm thick. In another embodiment, the first adhesive gel layer comprises 0.1%-60%, 1%-58%, 10%-55%, 20%-52%, 30%-50%, 35%-45%, or about 37.5% to about 42.5% w/v of the polypeptide in buffer. In a further embodiment, the second adhesive gel layer comprises 10%-80%, 20%-70%, 25-60%, 30%-50%, 35%-45%, or about 37.5-42.5% w/v calcium ion source in buffer, including but not limited to $CaCl_2 \cdot H_2O$; and 10%-80%, 20%-70%, 25-60%, 30%-50%, 35%-45%, or about 37.5-42.5% w/v potassium ion source in buffer, including but not limited to $KH_2PO_4$; or wherein the second adhesive gel layer comprises 10%-80%, 20%-70%, 25-60%, 30%-50%, 35%-45%, or about 37.5-42.5% w/v calcium ion source in buffer. In another embodiment, the second adhesive gel layer comprises 10%-80%, 20%-70%, 25-60%, 30%-50%, 35%-45%, or about 37.5-42.5% w/v calcium ion source in buffer, including but not limited to $CaCl_2 \cdot H_2O$; and wherein the third adhesive layer comprises 10%-80%, 20%-70%, 25-60%, 30%-50%, 35%-45%, or about 37.5-42.5% w/v potassium ion source in buffer, including but not limited to $KH_2PO_4$.

In another embodiment, a thickness of the second adhesive gel layer and/or the third adhesive gel layer is greater than a thickness of the first adhesive gel layer, including but not limited to a thickness ratio of about 2:1 between the second adhesive gel layer and the first adhesive gel layer when the third adhesive gel layer is absent, or a thickness ratio of about 2:1 between the second adhesive gel layer+third adhesive gel layer and the first adhesive gel layer when the third adhesive gel layer is present; and wherein the total thickness of the first, second, and third adhesive gel layers and any intervening layers is about 0.05 mm.

The adhesive gel layers may comprise any other components as deemed suitable for a given use. In various embodiments, the first adhesive gel layer, the second adhesive gel layer and/or the third adhesive gel layer further comprise a thickener, a surfactant, a flavoring agent, cellulose or a cellulose derivative, and/or a preservative.

In one embodiment, the first adhesive gel layer, the second adhesive gel layer and/or the third adhesive gel layer further comprise:
  0.1%-30% w/v of a thickener, including but not limited to propylene glycol (PPG), rosin, and/or glycerol;
  1%-30% w/v of cellulose or cellulose derivative, including but not limited to sodium carboxymethyl cellulose, cellulose, methyl ether, methylated cellulose, methylcellulose, E461 (designation number in food additive); other variations of cellulose substitutes: hydroxypropylcellulose; and
  0.1% to 5% of a surfactant.

The formulations of the adhesive gel layer embodiments may contain any other suitable ingredients/excipients as deemed appropriate, including but not limited to preservatives, flavoring agents, thickeners, surfactants, excipients, etc. In one non-limiting embodiment, the adhesive gel layers in a two layer embodiment comprise ingredients listed in Table 3. In a 3 layer embodiment, the third payer may be the same as the second layer, only the at least one calcium ion source is in one layer and the at least one phosphate ion source is in the other layer.

TABLE 3

Exemplary ingredients contained in the adhesive gel layers in a two layer embodiment

| Ingredients | First adhesive gel layer Weight to Volume % | Second adhesive gel layer Weight to Volume % |
| --- | --- | --- |
| Peptide | 0.1-10 | 0.1-10 |
| $CaCl_2 \cdot H_2O$ | 0.1-10 | 10-80 |
| $KH_2PO_4$ | 0.1-10 | 10-60 |
| $KHPO_4$ | 0.1-10 | 10-60 |
| Preservatives | 0.1-10 | 0.1-10 |
| Sweeteners | 0.1-50 | 0.1-50 |
| Thickener (including but not limited to propylene glycol (PPG), rosin, and/or glycerol; cellulose or cellulose derivative, including but not limited to sodium carboxymethyl cellulose, cellulose, methyl ether, methylated cellulose, methylcellulose, E461 (designation number in food additive); other variations of cellulose substitutes: hydroxypropylcellulose | 0.1-30 | 0.1-30 |
| Surfactant (any food grade surfactant, including but not limited to simethicone) | 1-5 | 1-5 |

The different adhesive layers may directly contact, or may be separated by a separation layer. Such a separation layer may comprise any suitable separation layer, including but not limited to a thin layer of cellulose gum gel.

In another embodiment, the first formulation comprises 10%-80%, 20%-75%, 30-70%, 40%-60%, 45%-55%, or about 47.5 to about 52.5% w/v of the polypeptide in buffer. In a further embodiment, the one or more further formulations comprise a second formulation and a third formulation, wherein:
  the second formulation comprises 10%-80%, 20%-75%, 30-70%, 40%-60%, 45%-55%, or about 47.5 to about 52.5% w/v of the at least one calcium ion source, including but not limited to $CaCl_2$; and the third formulation comprises 10%-80%, 20%-75%, 30-70%, 40%-60%, 45%-55%, or about 47.5 to about 52.5% w/v of the at least one phosphate ion source, including but not limited to $K_2HPO_4$.

In this embodiment, the composition comprises a dental gel/varnish. In one embodiment, the first formulation, the second formulation, and the third formulation further comprise a preservative, a thickener, a flavoring agent, and/or a surfactant. In another embodiment, the first formulation, the second formulation, and the third formulation further comprise:

5%-50% w/v of a thickener, including but not limited to polypropylene glycol (PPG), glycerol, sodium carboxymethyl cellulose, and/or rosin; and/or
0.1%-5% of a surfactant.

In a further embodiment, the one or more further formulations comprise a second formulation and a third formulation, wherein the first, second, and third formulations are first, second, and third pastes and are each separated by a separation paste, wherein:

the first past comprises 10%-80%, 20%-75%, 30-70%, 40%-60%, 45%-55%, or about 47.5 to about 52.5% w/v of the polypeptide in buffer;

the second paste comprises 10%-80%, 20%-75%, 30-70%, 40%-60%, 45%-55%, or about 47.5 to about 52.5% w/v of the at least one calcium ion source, including but not limited to $CaCl_2$; and the third paste comprises 10%-80%, 20%-75%, 30-70%, 40%-60%, 45%-55%, or about 47.5 to about 52.5% w/v of the at least one phosphate ion source, including but not limited to $K_2HPO_4$; and wherein viscosity of the first paste is less than viscosity of the second paste and the third paste.

In this embodiment the composition comprises a toothpaste, in which the viscosity of the formulation, and relative concentrations and overall amounts of the active ingredients determine the dissolution rate of peptide and ions from the tri-component paste structure providing sequential release of peptide followed by ion components. In one embodiment, the first paste, the second paste, and the third paste comprises a thickener, including but not limited to polypropylene glycol (PPG), glycerol, and/or sodium carboxymethyl cellulose. In another embodiment, the first paste, the second paste, and the third paste comprise propylene glycol (PPG), glycerol, and sodium carboxymethyl cellulose (SCS), wherein the first paste comprises a higher concentration of PPG than the second paste and the third paste, and wherein the first paste comprises a lower concentration of SCS than the second paste or the third paste. In a still further embodiment, a ratio of PPG in the first paste compared to the second paste and the third paste is about 5:3, and/or wherein a ratio of SCS in the first paste compared to the second paste and the third paste is about 2:3.

The pastes may be stored, for example, in a squeezable or pump action toothpaste tube as individual strips of paste spanning the length of the tube and optionally separated by layer of neutral paste (for example, paste made of inactive ingredients only).

The pastes of these toothpaste embodiments may contain any other suitable ingredients/excipients as deemed appropriate, including but not limited to preservatives, flavoring agents, thickeners, surfactants, etc. In one non-limiting embodiment, the pastes comprise ingredients listed in Table 4

TABLE 4

Base gel formulation ingredients list for toothpaste formulation.

| | Peptide paste Weight % | Ca based paste Weight % | $PO_4$ based paste Weight % |
|---|---|---|---|
| Active Ingredient: | | | |
| Peptide | 30-70 | | |
| Calcium ion source | | 30-70 | |
| Phosphate ion source | | | 30-70 |
| Preservative: | | | |
| Potassium sorbate | 0.5 | 0.5 | 0.5 |
| Thickener/Humectant: | | | |
| Propylene Glycol (PPG) | 0-10 | 0-10 | 0-10 |
| Glycerol (Glycerin) | 0-20 | 0-20 | 0-20 |
| Cellulose Gum (Sodium Carboxymethyl Cellulose) | 2-6 | 3-10 | 3-10 |
| Sweetener/Flavor: | | | |
| Sorbital, 60% aqueous solution | 29 | 29 | 29 |
| Surfactant: | | | |
| Simethicone (antifoam) | 0.5 | 0.5 | 0.5 |

In all of these embodiments or combinations thereof, the polypeptide may comprise or consist of the amino acid sequence selected from the group consisting of:

(SYENSHSQAINVDRT)$_{1-10}$ (shADP5; SEQ ID NO:16), or a functional equivalent thereof;
(PGYINFSYENSHSQAINVDRTA)$_{1-10}$ (SEQ ID NO: 6) (ADP5H), or a functional equivalent thereof; and
(SYEKSHSQAINTDRT)$_{1-10}$ (sADP5; SEQ ID NO:24), or a functional equivalent thereof;
or a combination thereof.

In another embodiment, polypeptide comprises or consists of an amino acid sequence selected from the group consisting of:
(HTLQPHHH(L/I)PVV)$_{1-10}$ (ADP1; SEQ ID NO:1);
(VPG(H/Q)HSMTP(T/I)QH)$_{1-10}$ (ADP2; SEQ ID NO:4);
(HPP(S/T)HTLQPHHH(L/I)PVV)$_{1-10}$ (ADP4; SEQ ID NO:10);
(PAQQPV(A/I)PQQPMMP)$_{1-10}$ (ADP8; SEQ ID NO:21);
(HPP(S/T)HTLQPHHH(L/I)PVVPAQQPV(A/I) PQQPMMPVPG(H/Q)HSMTP (T/I)QH)$_{1-10}$ (ADP7; SEQ ID NO:18);
(HTLQPHHHLPVV)$_{1-10}$ (ADP1M; SEQ ID NO:2);
(HTLQPHHHIPVV)$_{1-10}$ (ADP1H; SEQ ID NO:3);
(VPGHHSMTPTQH)$_{1-10}$ (ADP2M; SEQ ID NO:5);
(VPGQHSMTPIQH)$_{1-10}$ (ADP2H; SEQ ID NO:14);
(HPPSHTLQPHHHLPVV)$_{1-10}$ (ADP4M; SEQ ID NO:11);
(HPPTHTLQPHHHIPVV)$_{1-10}$ (ADP4H; SEQ ID NO:12);
(HPPSHTLQPHHHLPVVPAQQPVAPQQPMMPVPG-HHSMTPTQH)$_{1-10}$ (ADP7M; SEQ ID NO:19);
(HPPTH-TLQPHHHIPVVPAQQPVIPQQPMMPVPGQHSMT-PIQH)$_{1-10}$ (ADP7H; SEQ ID NO:20);
(PAQQPVAPQQPMMP)$_{1-10}$ (ADP8M; SEQ ID NO:22); and
(PAQQPVIPQQPMMP)$_{1-10}$ (ADP8H; SEQ ID NO:23);
(WPATDKTKREEVD)$_{1-10}$ (ADP3M; SEQ ID NO:8);
(WPSTDKTKREEVD)$_{1-10}$ (ADP3H; SEQ ID NO:9),
MLPHHGA (HABP1; SEQ ID NO:25); and
NPGFAQA (HABP2; SEQ ID NO:26);

or a functional equivalent thereof, or a combination thereof.

As used herein, a "functional equivalent" of a polypeptide is one that retains the biological activity of the polypeptide in treating dental disorders, and included one or more amino acid substitutions, deletions, additions, or insertions. In various embodiments, the functional equivalent is at least 50%, 55%, 60%, 65%, 70%, 75%, 80%, 85%, 90%, 91%, 92%, 93%, 94%, 95%, or more identical to the recited polypeptide.

As used throughout the present application, the term "polypeptide" is used in its broadest sense to refer to a sequence of subunit amino acids, whether naturally occurring or of synthetic origin. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, or glycosylation. Such linkage can be covalent or non-covalent as is understood by those of skill in the art.

In various embodiments, the recited polypeptides may be present in 1, 2, 3, 4, 5, 6, 7, 8, 9, or 10 copies, preferably in one copy. When present in multiple copies, the copies are contiguous to each other. For example, 2 copies of ADP5 would be: PGYIN(L/F)SYE(K/N)SHSQAIN(T/V)DR-TAPGYIN(L/F)SYE(K/N)SHSQAIN(T/V)DRT A (SEQ ID NO: 15). Further examples will be readily apparent to those of skill in the art based on the teachings herein.

In another embodiment, the polypeptide is present in a single copy. In a further embodiment, the polypeptide is linked to an anti-microbial peptide. Any suitable anti-microbial peptide may be used including but not limited to

```
                              (SEQ ID NO: 27)
KWKRWWWWR;

(SEQ ID NO: 28)
LKLLKKLLKLLKKL;

(SEQ ID NO: 29)
CPFVC;

(SEQ ID NO: 30)
RRXXRFF;

(SEQ ID NO: 31)
ALLHHGLNCAKGVLA;

(SEQ ID NO: 32)
LWKTLLKKVLKAAA;

(SEQ ID NO: 33)
GLRKRKRKFRNKKKEKLKKI;
and (SEQ ID NO: 34)
RKRIHIGPGRAFYTT.
```

In another embodiment, the first formulation and/or the one or more further formulations further comprises fluoride. In one embodiment, the fluoride is present in the first formulation and/or the one or more further formulations at between about between about 50 parts per million (ppm) and about 20,000 ppm, between about 50 ppm and about 10,000 ppm, between about 50 ppm and about 5000 ppm, between about 50 ppm and about 1000 ppm, between about 50 ppm and about 500 ppm, or about 75 ppm and about 400 ppm, between about 100 ppm and about 300 ppm, between about 150 ppm and about 250 ppm, or about 200 ppm.

The polypeptides of the invention may be the sole active agent in the pharmaceutical composition, or the composition may further comprise one or more other active agents suitable for an intended use, including but not limited to anti-microbial polypeptides (inhibiting bacterial infection), biomineralization-promoting polypeptides (i.e.: any polypeptides that are useful for controlling or promoting biomineralization), inorganic material-binding polypeptides, three-dimensional scaffold-forming polypeptides, collagen, chitosan, amphiphilic peptides, protein-binding polypeptides, enamelin-derived polypeptides, tuftelin-derived peptides, statherin-derived polypeptides, dentin-derived polypeptides, bone sialoprotein-derived polypeptides, osteocalcin-derived polypeptides, osteopontin-derived polypeptides, proteins with caries inhibitory activity, casein, and bone morphogenetic-derived polypeptides.

The compositions or kits of the disclosure may include any other components as deemed appropriate for an intended use.

In another aspect, the disclosure provides methods for treating a dental disorder, whitening teeth, restoring and retaining the tooth structure, and/or restoring the mineral content of tooth-mineral loss due to demineralization, comprising orally administering to a subject in need thereof:

(a) a first formulation comprising an effective amount to treat a dental disorder, whiten teeth, restore and retain the tooth structure, and/or restore the mineral content of tooth-mineral loss due to demineralization, of a polypeptide comprising or consisting of the amino acid sequence selected from the group consisting of:

(SYENSHSQAINVDRT)$_{1-10}$ (shADP5; SEQ ID NO:16);
(SYEKSHSQAINTDRT)$_{1-10}$ (sADP5; SEQ ID NO:24)
(WP(A/S)TDKTKREEVD)$_{1-10}$ (ADP3; SEQ ID NO:7);
(PGYIN(L/F)SYE(K/N)SHSQAIN(T/V)DRTA)$_{1-10}$ (ADP5; SEQ ID NO:13);
(LPPLFSMPLSPILPELPLEAWPAT)$_{1-10}$ (ADP6; SEQ ID NO:17);
(HPP(S/T)HTLQPHHH(L/I)PVVPAQ QPV(A/I) PQQPMMPVPG(H/Q)HSMTP (T/I)QH)$_{1-10}$ (ADP7; SEQ ID NO:18); and
12-42 contiguous amino acids of (HPP(S/T)HTLQPHHH (L/I)PVVPAQ QPV(A/I)PQQPMMPVPG(H/Q) HSMTP(T/I)QH)$_{1-10}$ (ADP7; SEQ ID NO:18), or functional equivalents or combinations thereof; and (b) one or more further formulations comprising at least one calcium ion source and/or at least one phosphate ion source;

wherein the first formulation is administered to the subject such that the polypeptide is accessible to one or more teeth of the subject prior to $Ca^{2+}$ released from the at least one calcium ion source and $PO_4^{3-}$ released from the at least one phosphate ion source.

Thus, the methods comprise the use of any composition or kit disclosed herein for treating a dental disorder, whitening teeth, restoring and retaining the tooth structure, and/or restoring the mineral content of tooth-mineral loss due to demineralization. All embodiments and combinations of embodiments disclosed herein for the compositions and kits may be used for the methods.

The subject may be any subject that can contract a dental disorder, including but not limited to mammals. In various embodiments, the mammal is a human, dog, cat, horse, cow, sheep, goat, pig, or other pet or food/dairy animal. In a preferred embodiment, the subject is a human.

As used herein, a dental disorder is any disease or condition affecting the teeth, gums (gingiva), or other tissues of the mouth that involves (directly or indirectly) demineralization (i.e.: loss of mineral content on the surface of the tooth). In a healthy person, tooth is in a cycle of demineralization and remineralization through the exchange of ions between the surface of the tooth and the surrounding saliva. When the rate of demineralization exceeds the rate of remineralization, it leads to a dental disorder. Demineralization is a major cause of most dental disorders. Loss of mineral can be caused by any means, including but not limited to acidic diet, dry mouth, tooth whitening, tooth wear and cariogenic bacteria.

Such dental disorders may include, but are not limited to, periodontitis, tooth erosion, hypersensitivity, dental caries (also known as tooth decay/cavities), dental fluorosis, tooth resorption, craniomaxillofacial bone disease, and gingival recession.

As used herein, "periodontitis" is a set of inflammatory diseases affecting the periodontium, i.e., the tissues that surround and support the teeth. Periodontitis involves progressive loss of the alveolar bone around the teeth, and if left untreated, can lead to the loosening and subsequent loss of teeth. Periodontitis is caused by microorganisms that adhere to and grow on the tooth's surfaces, along with an overly aggressive immune response against these microorganisms.

As used herein, "tooth demineralization" or "tooth wear" is wear of tooth enamel. This tooth wear may be caused by any number of factors, including erosion (acidic diet), teeth grinding (attrition) due to normal function or parafunction, abrasion and in some cases abfraction.

As used herein, "hypersensitivity" is an increased exposure to the environment of nerves inside the dentin of teeth, causing an increased nerve response, which can be mild to severe. The sensitivity may be caused by any factor, including but not limited to wear, tooth decay or exposed tooth roots.

As used herein, "dental caries" is an infectious disease usually bacterial in origin that causes demineralization of the hard tissues (enamel, dentin and cementum) and destruction of the organic matter of the tooth. The bacteria most commonly responsible for dental cavities are *Streptococcus mutans* and *Lactobacillus*. If left untreated, dental caries can lead to pain, tooth loss and systemic infection.

As used herein, "dental fluorosis" is a developmental disturbance of dental enamel caused by excessive exposure to high concentrations of fluoride during tooth development. The risk of fluoride overexposure is greatest between the ages of 3 months and 8 years. In its mild forms, fluorosis often appears as unnoticeable, tiny white streaks or specks in the enamel of the tooth. In its most severe form, tooth appearance is marred by discoloration or brown markings. The enamel may be pitted, rough and hard to clean. The spots and stains left by fluorosis are permanent and may darken over time.

As used herein, "tooth resorption" is a process by which all or part of a tooth structure is lost. In "external resorption" the root surface is lost; this can be caused, for example, by chronic inflammation, cysts, tumors, trauma, reimplantation of a tooth, or by unknown causes. "Internal resorption" involved resorption of dentin and pulpal walls centrally within the root canal; the cause can sometimes be attributed to tooth trauma, but often there is no known cause.

As used herein, "gingival recession" is root (cementum) that is exposed to the environment as a result of retraction of the gumline from the crown of the teeth. Cementum is a calcified tissue that supports attachment of the tooth to mandibular or maxillary bone through periodontal ligaments. Exposed cementum can result in resorption of cementum and exposure of the underlying dentin, therefore, hypersensitivity and pain.

In one embodiment, "craniomaxillofacial bone disease" refers to disease of dental bone structures.

As used herein, "treating dental disorder" means accomplishing one or more of the following: (a) reducing the severity of the dental disorder; (b) limiting or preventing development of symptoms characteristic of the dental disorder (s) being treated; (c) inhibiting worsening of symptoms characteristic of the dental disorder (s) being treated; (d) limiting or preventing recurrence of the dental disorder (s) in patients that have previously had the disorder(s); (e) limiting or preventing recurrence of symptoms in patients that were previously symptomatic for the dental disorder (s); and (f) limiting development of the dental disorder in a subject at risk of developing the dental disorder, or not yet showing the clinical effects of the dental disorder.

The methods and compositions of any embodiment or combination of embodiments of the disclosure can also be used for restoring and retaining the tooth structure, restoring the mineral content of tooth-mineral loss due to demineralization, or whitening the teeth for cosmetics purposes.

As used herein, an "amount effective" refers to an amount of the polypeptide that is effective for treating and/or limiting dental disorders.

In one embodiment, the lozenge compositions disclosed herein are orally administered to the subject. Once the shell region is dissolved in the saliva, the polypeptides are released from and deposited onto the teeth. After the shell region is dissolve, the core region then supplies calcium and phosphate ions to the teeth to initiate biomineralization. The restoration process includes restoration of the mineral structure, thereby eliminating the risk of hypersensitivity by thickening the enamel and penetrating into the dental tubules, and restores the natural "white" color of the teeth.

In another embodiment, the mouthwash compositions and kits disclosed herein are orally administered to the subject, and the polypeptide is released first and binds to the teeth quickly (for example, within 10, 20, 30, 40, 50, 60 seconds), followed by calcium and phosphate ions supplied either in a second container, or present in the same formulation as the polypeptides but within vesicles that delay release of the ions until after polypeptide binding to the teeth.

In a further embodiment, the dental strips/adhesive gel layer embodiments of the compositions and kits disclosed herein are applied to the teeth of the subject. The strips are flexible to be bent over the tooth edge covering both the facing surface as well as the inside surface. The strips cause mineral formation on the surface of the damaged tooth as well as it causes the newly formed mineral to penetrate into the exposed dental tubules, to treat dental hypersensitivity.

In a still further embodiment, the toothpaste compositions are administered to the subject through, for example, brushing of the teeth. The polypeptides are present in the first paste that has a lower viscosity than that of the second and third pastes from which the ions are released. The pastes may be stored, for example, in a squeezable or pump action toothpaste tube as individual strips of paste spanning the length of the tube and optionally separated by layer of neutral paste (for example, paste made of inactive ingredients only).

Example 1

Tooth discoloration is a common aesthetic concern for many individuals and in response the dental profession and public expend considerable amounts of time and money to improve the appearance of stained teeth. Depending on the source and location of the stain deposits, tooth discoloration can be classified into different categories which may also be of merit to develop targeted therapies. These include, (i) Extrinsic discoloration where the chromogens deposit on the external surface of the tooth or within the pellicle layer such as tea, coffee, tobacco, metallic and salt components of dietary products (copper, sulfides); (ii) Intrinsic staining where optical properties of the teeth are altered due to structural changes in dentin as a result of aging, genetic factors, leakage of root canal treatment materials or metabolic diseases, e.g., alkaptonuria, congenital erythropoietic *porphyria*, congenital hyperbilirubinemia, amelogenesis imperfecta, dentinogenesis imperfecta. The exposure to the chromogens e.g., tetracycline staining, fluorosis; chemotherapeutic drugs during the teeth development at early childhood is also another cause of intrinsic teeth staining where the chromogens incorporate into the dentin tissue. Other types of dental discoloration are iii) Stain internalization where extrinsic chromogen pigments are incorporated within the mineral tissue during the tooth development through enamel and dentin defects or leakage of dental restorative material and (iv) Superficial subsurface demineralization in the form of white-spot lesions which occurs as a result of prolonged bacterial acidic attack due to the enhanced microbial activity around the dental bracelets and other orthodontic appliances.

The main problem with current whitening methods is the use of highly reactive peroxide-based chemicals which remove discoloration by dissolving stained mineral layer from the surface of teeth. This chemical-etching process is at the expense of the enamel—the fully mineralized outer layer of the tooth crown. As a consequence, underlying dentin becomes exposed, creating problems such as hypersensitivity and increased susceptibility to cavities that far outweigh any cosmetic benefits. The American Dental Association reports that enamel erosion caused by peroxide demineralization can lead to adverse effects: hypersensitivity (occurring in 64% of patients), gum (gingival) recession, pulp inflammation and cavities due to regular use of whitening products.

Herein, we developed a tooth whitening lozenge, and related embodiments, which can be used as a vehicle to deliver mineralization ingredients, peptide and ionic calcium and phosphate, in a practical way and thereby, provide teeth whitening through the additive, biomimetic process.

The current hydrogen peroxide-based whitening products remove the teeth discoloration by chemically etching the natural teeth mineral on enamel which in turn removes the stains deposits residing on top of the minerals. While this abrasive etching process results in whiter teeth by exposing the inner-unstained regions of the tooth mineral, it is in the expense of the teeth which leaves behind highly etched, demineralized tooth surface. On the other hand, the compositions and methods disclosed herein whiten the teeth by regenerating the natural tooth mineral through peptide-enabled biomimetic restoration process. In the lozenge embodiment, the lozenge contains two active layers: a shell with a biomineralizing peptide which catalyzes enamel regeneration, and an inner core containing calcium and phosphate—the raw materials needed for natural remineralization. Each layer plays an important role in the restoration process. Once the outer shell is dissolved, the polypeptides are released from the outer layer and deposited onto the teeth. After the shell is spent, the inner core then supplies calcium and phosphate to the biomineralizing components. The restoration process includes regeneration of the mineral structure (eliminating the risk of hypersensitivity by thickening the enamel) and natural color of the teeth.

Figure 2:
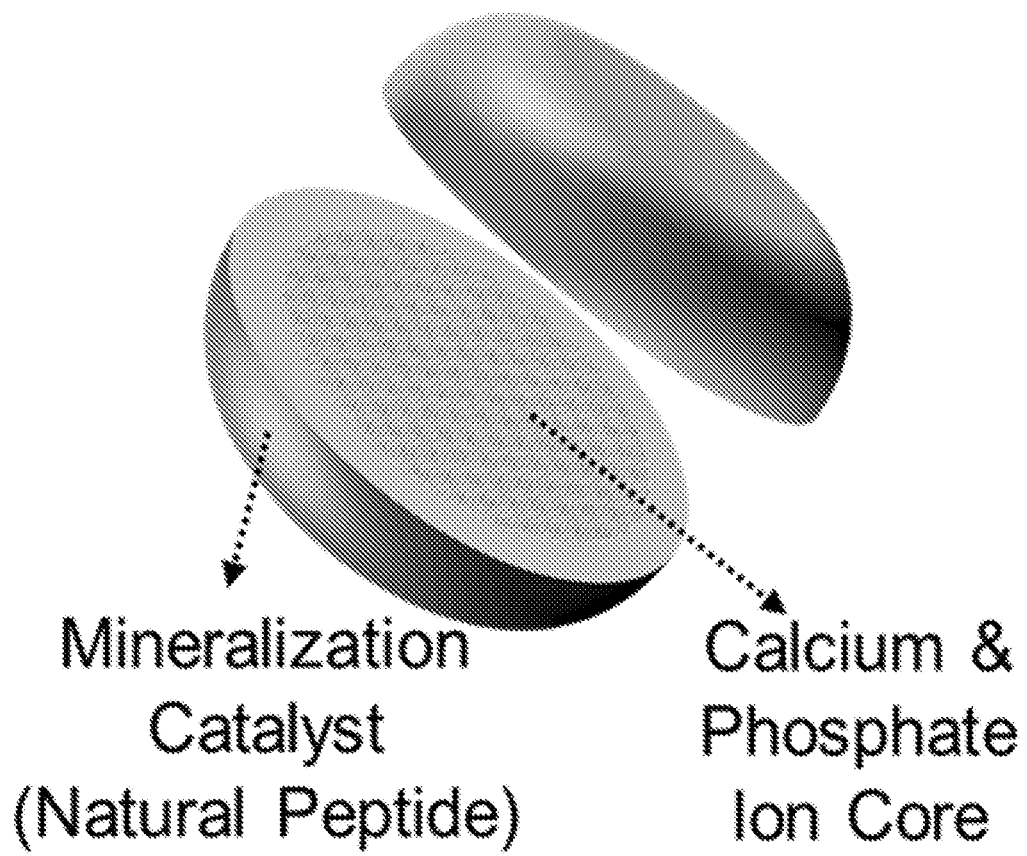
FIG. 2. A schematic representation of the core-shell design lozenge.

The remineralizing whitening product, such as a lozenge, comprises a core-shell architecture. The shell contains the remineralizing peptide as an active ingredient while the core contains the ionic calcium and phosphate (FIG. 2) as major ingredients. The core and the shell components of the remineralizing whitening lozenge is formulated separately using different amounts of excipients.

An active ingredient in the lozenge shell (peptide) was blended with a lubricating agent (Mg-Stearate), sweeteners in the form of sorbitol, xylitol, mint and other types of plant flavors, excipients in the form of talc, lactose, menthol, etc. Prior to manufacturing, ingredients were dry mixed and homogenized by ball mill.

TABLE 5

Lozenge formulation used in the following studies

| Ingredients | Lozenge Shell Region | | Lozenge Core Region | |
|---|---|---|---|---|
| | Amount (mg) | Weight % | Amount (mg) | Weight % |
| shADP5 Peptide (Active Ingredient) | 3.0 | 3.0 | 0 | 0.0 |
| $CaCl_2 \cdot 2H_2O$ (Active Ingredient) | 0.0 | 0.0 | 92.9 | 54.65 |
| $KH_2PO_4$ (Active Ingredient) | 0.0 | 0.0 | 51.6 | 30.35 |
| Mg-Stearate (lubricant) | 5.0 | 5.0 | 8.5 | 5.0 |
| D-Sorbitol (flavoring agent) | 10.0 | 10.0 | 17.0 | 10.0 |
| Talc (Filler/Excipient) | 82.0 | 82.0 | 0.0 | 0.0 |
| Total | 100.00 | 100.00 | 170.00 | 100 |

The remineralizing whitening lozenges were manufactured to lozenge-shape by compressing the blended ingredients within metal dies (in 6 to 15 mm in diameter) using hydraulic press machines under the compression force that was kept within the range of 5000 to 10000 ton/m$^2$.

To analyze disintegration time, a USP Dissolution 2 (USP-2) Apparatus was used. This apparatus is a simulated oral environment used in the literature where a paddle and shaft system stir artificial saliva at 37° C. at 60 rpm. Testing was started with the addition of 9 ml of saliva into the system and then it was removed and replaced accordingly every 1 minute to mimic swallowing and reproduction of saliva. Lozenges compressed at different forces and composed of varying ingredients were analyzed by quantifying the total weight of initial and remaining lozenge. In the next step, extracted human teeth specimen were placed into USP-2 apparatus and lozenge treatment were performed by addition of artificial saliva into the USP-2 container under constant stirring at 60 rpm, at 37° C. The lozenge treatment was performed for 15 mins by replacing the artificial saliva within the container every minute and completed by removing the teeth specimens out the USP apparatus at the end of 15 mins. The specimens were rinsed with deionized water and fractured into two pieces to perform both surface and cross-sectional analysis via Scanning Electron Microscope (SEM). Prior to SEM analysis, samples were dried with forced air and coated with 5 nm gold layer.

Whitening quantification of lozenge treated human teeth specimens were done using macro-photography imaging and Adobe Lightroom color analysis software. The teeth specimen was mounted on metal strips and placed into Vita Shade Guide rock according to visual assessment. Images were taken before and after lozenge treatment using Canon Rebel T5i camera w/Macro Lens 18-135 mm within a custom-made photo-station equipped with white LED and diffuser. While the semi-quantitative quantification was done based on visual shade comparison using vita shade guides, the absolute color analysis was performed by analyzing the imaging using Adobe Lightroom color analysis software. Results were expressed with the CIE L*a*b* color model that is used commonly in dentistry.

The head-to-head comparison of whitening lozenge with existing HP-based teeth whitening products were done on extracted human teeth collected from dental clinics. The teeth specimen were mounted on metal strips and placed into Vita Shade Guide rock according to visual assessment. For comparison products, 14% HP containing whitening strips and 40% HP containing clinical whitening gels were used. Each teeth were subjected to 7 rounds of whitening treatment according to manufacturer's directions. Lozenge treatment was performed within USP-2 apparatus as described previously. Images of specimen were taken before and lozenge treatment using Canon Rebel T5i camera w/Macro Lens 18-135 mm within a custom-made photo-station equipped with white LED and diffuser. While the semi-quantitative quantification was done based on visual shade comparison using vita shade guides, the absolute color analysis was performed by analyzing the imaging using Adobe Lightroom color analysis software. Results were expressed with the CIE L*a*b* system.

Results

Figure 3:
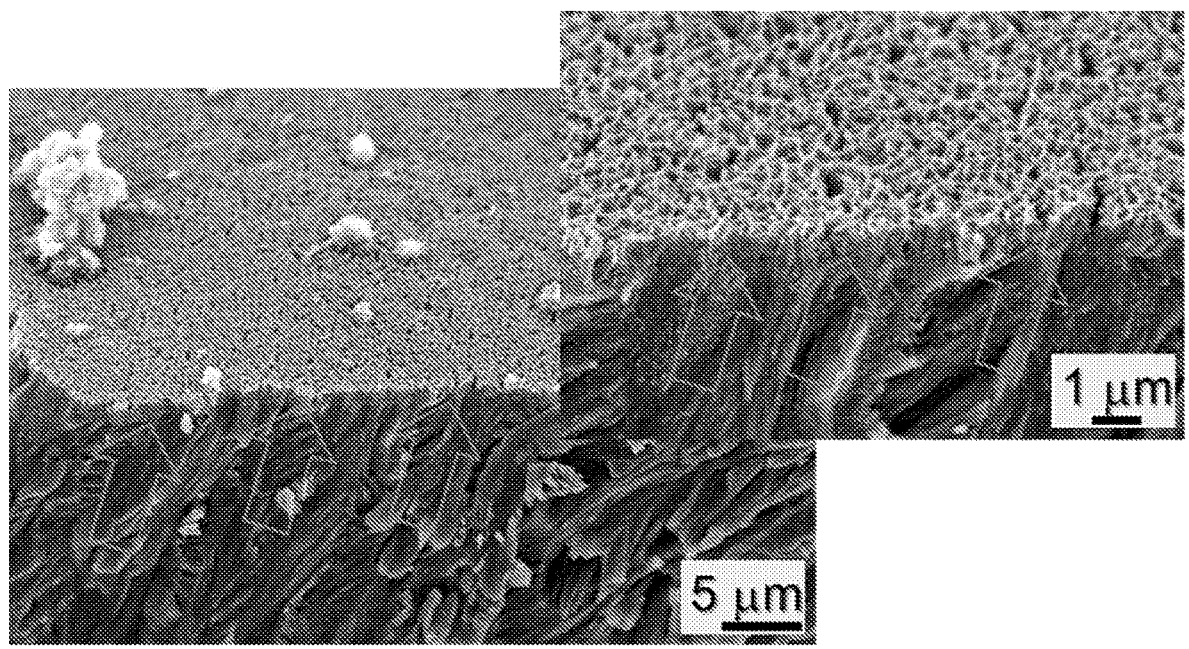
FIG. 3. Representative Scanning electron microscopy (SEM)images taken after one round of lozenge treatment of human enamel.

Following to dissolution time testing the optimal tablet formulation and compression force which yield to complete dissolution of whitening lozenge within artificial saliva in 15 mins was identified (see Table 5). Next, an extracted human tooth sample was placed into the USP 2 Dissolution Apparatus and mineralization was performed for 15 mins. A continuous mineral layer with plate-like crystals were formed on enamel with a calculated thickness of ~1 μm as a result of single round of lozenge treatment on extracted human teeth (FIG. 3).

Figure 4:
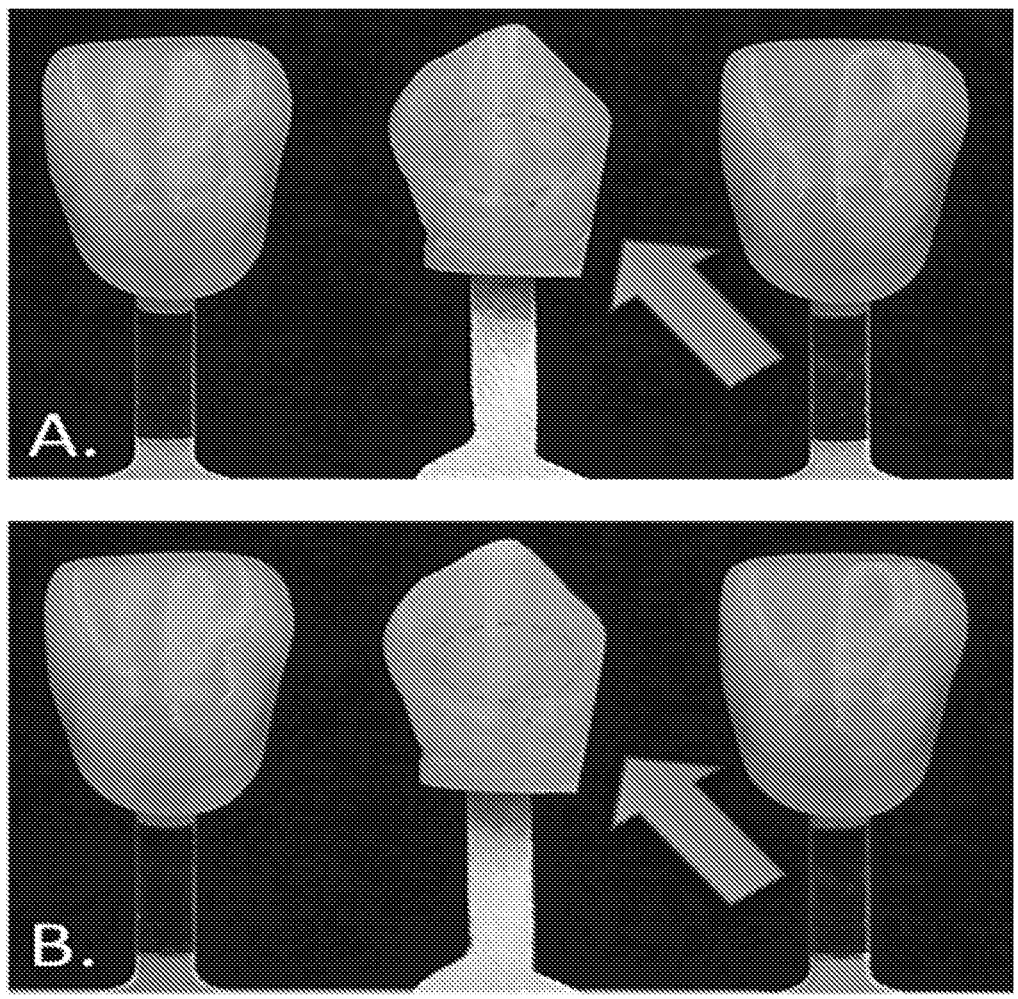
FIG. 4. Optical images of inherently stained extracted human teeth (a) before and (b) after remineralizing whitening treatment. Circled area shows the region where the color quantification analysis is done.

The whitening performance of the remineralizing lozenge was measured by macro-photography and color analysis. With this aim, the core-shell lozenge was fabricated by compressing in hydraulic press. An extracted human tooth sample with inherently dark shade was mounted on a stainless-steel holder and placed into shade guide rack. Images under pre-set light settings were recorded. Next the specimen was placed into the USP 2 dissolution apparatus and mineralization was performed for 15 mins. The sample was removed, drip washed with distilled water and placed back into same position on the shade rack and optical images were taken (FIG. 4). As shown in FIG. 4, the average color of untreated sample (within the dotted circle) was measured using Adobe Lightroom in CIE system, expressed as L*a*b color units. The three coordinates of CIE L*a*b* represent the lightness of the color where L=0 yields black and L=100 indicates diffuse white, a=negative values indicate green while a=positive values indicate magenta and b=negative values indicate blue and b=positive values indicate yellow. While average color of the teeth specimen before treatment was quantified as L-68.93, a=2.93, b=27.92 after the remineralization treatment it is measured as L=69.37, a=3.93, b=22.47. The ΔE value that indicates the total change in whiteness was calculated as 5.56 using the equation 1; given below:

$$\Delta E_{Lab} = \sqrt{(\Delta L^*)^2 + (\Delta a^*)^2 + (\Delta b^*)^2} \quad (1)$$

The head-to-head comparison of whitening lozenge with HP-based commercial teeth whitening products were done on extracted human teeth mounted on metal strips. One half of each sample were subjected to 7 consecutive rounds of whitening treatment (1 treatment per day) while the other half received no treatment. Specimens were kept in artificial saliva in between each treatment. 4 test groups were used: 1) No treatment, 2) Treatment with 14% HP containing whitening strips, 3) Treatment with 40% HP containing clinical whitening gels and 4) Whitening Lozenge treatment. Images of specimen were taken but placing both halves of the teeth next to each other using Canon Rebel T5i camera w/Macro Lens 18-135 mm within a custom-made photo-station equipped with white LED and diffuser. While no significant change was observed or quantified between the left and right side of the negative control sample (received no treatment), the other 3 groups which received different types of whitening treatment showed varying amount of whitening compared to left half as well as images taken before the treatment from the right side of the teeth. As shown in Table 6 below, ΔE values (change in whiteness) was calculated as 4.0±2.8, 11.1±2.8, 10.2±1.1 for specimens treated with 7 rounds of whitening strips (14% HP), clinical gel (40% HP) and whitening lozenge, respectively. These results demonstrate that under similar treatment conditions (shown in Table-3), the whitening lozenges are three times more effective than their OTC counterparts, whitening strips. More importantly, the whitening performance of lozenges is comparable to clinical gels which are ~300 times more expensive than lozenges and requires a dental clinician.

TABLE 6

Whitening performance of commercial products vs remineralizing lozenges.

| Treatment Product | Clinical vs. OTC | Treatment Time & # of Cycles | Degree of Whitening (ΔE) | Whitening Mode | Price | Healthy | Overall Score |
|---|---|---|---|---|---|---|---|
| Whitening Strip (% 14 HP) | OTC | 30 mins- 7 times (1 per day) | 4.0 ± 2.8 | Subtractive | $3/strip $90/box | No | 5 |
| Whitening Gel (% 40 HP) | Clinical | 20 mins- 7 times (1 per day) | 11.1 ± 2.8 | Subtractive | $5/syringe $40/box $600/clinician time | No | 7 |
| Whitening Lozenge (Healthy) | OTC | 15 mins- 7 times (1 per day) | 10.2 ± 1.1 | Additive | 50¢/Lozenge $5/box | Yes | 10 |

Figure 5:
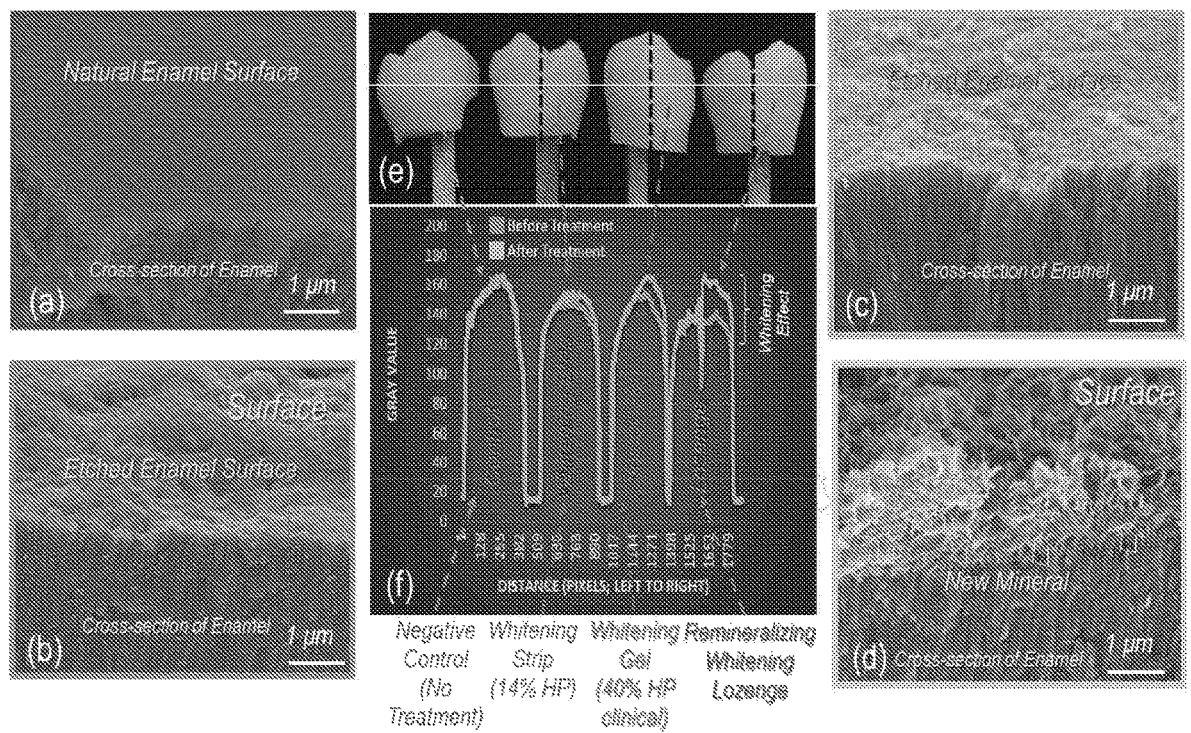
FIG. 5. Structural evaluation of the mode of action of the whitening procedure and head-to-head comparison with those of commercial products. SEM images of tooth samples received (a) No treatment and 7 rounds of (b) Whitening strip, (c) Whitening gel and (d) Whitening Lozenges. (e & f) Quantification of Whitening after 7 rounds of treatment (1 week)*Whiteness quantified along the white line in (e) and the whiteness profiles are shown in (f). The results demonstrated that the Whitening Lozenges are as effective as clinically used Whitening Gels (40% HP) and 3× more effective than OTC Whitening Strips.

To demonstrate the effect of these treatment modalities to the natural tooth surface, following whitening quantification, samples were subjected to SEM analysis. As shown in FIG. 5 below, natural tooth surface (no treatment) is smooth and has a uniform contrast. Following whitening strip treatment, the surface becomes rougher which is an indication of demineralization process in response to hydrogen peroxide treatment. More importantly, the roughness of teeth surface after clinical gel treatment is increased which could be explained by the higher hydrogen peroxide content of clinical gels. On the other hand, in contrast to chemical etching effect of commercial products, lozenge treatment created a new mineral layer with about 2 µm in thickness. As a summary, while the HP-based commercial products etch the surface of enamel and bring about natural color of enamel at different degrees, the remineralizing lozenges covers the surface with a new mineral and whitens teeth in a healthier way.

Other Embodiments

Numerous other embodiments of compositions according to the present disclosure are possible, in light of the demonstrated improvements of the lozenge embodiment that could be used for whitening of teeth and healthier and fresher oral care. These consumer products include tooth paste, chewing gums, mouth fresheners, dental strips, gels in dental trays, dental guards, etc. The methods and materials are described here to bring about the remineralization action of the peptide in a dual-component design of the products. The dual-component design involves two active ingredients: one containing the peptide and the other containing the calcium and phosphate ions. In this design, the remaining of the inactive components in the formulation may be incorporated in either of the components. The second discovery is that the dual-component design can be dissolved in a simulated saliva solution under the physiological conditions of the oral cavity. These two elements, or components, when active concurrently develop a condition in which the remineralization mechanism of action becomes viable. Furthermore, dissolution time of the product (e.g., lozenge) can be controlled by careful selection of the inactive ingredients. Potential Consumer Products (not exclusive) include toothpaste, chewing gums, mouthwash/gargle tablets, gel, liquid dentifrices, dental tablets/lozenges/troches/pastilles, topical gels, dental pastes, tooth varnishes, dental mousse and food products.

Tooth-Paste: Dual-component design incorporates two formulations, one containing the remineralizing peptide and the other including the calcium and phosphate ions; the rest of the formulation contains inactive ingredients. While each of the formulations has different chemical compositions, each would have the same mechanical characteristics, in particular, the viscosity and physical properties, such as modulus and plasticity. Dissolution characteristics of each component would also be the same, enabling a full dissolution within the oral environment in contact with saliva and be solubilized within it simultaneously. This has been demonstrated in the case of lozenge and the same method is used in the case of tooth-paste. Dual-component design has two channels within a given single tube of the paste: one contains the paste incorporating the peptide, and the other paste contains the ions. When squeezed through, on the tooth brush, the two components mix and when applied onto the teeth, the two components mix to bring the mechanism of action of the remineralization.

Chewing Gum—Layered gum has two components: one containing the peptide and the other the two ions. The two layers have the same structural and physical characteristics. The thickness of the two layers would be the same. The viscosity and the chemical and mechanical stabilities of the two components are also the same, meaning the inactive components are similar. Under the mastication action, two active components mix, each dissolving in saliva. Upon immobilization on the tooth surface, the peptide recruits the ions and causes the remineralization. Each gum has a certain lifetime, during which the ions and the peptide continuously released from the gum, but at a decreasing rate, dissolving in the saliva and remineralizing on the surface of the teeth.

Mouth Wash—The dual-component design in the remineralizing mouth-wash involves two microcontainers (e.g., vesicles) containing either the peptide or the ions. In contact with saliva the membranes of the vesicles would dissolve, and the contents are released into the saliva and, when in contact, to form the new mineral on the surface of the teeth. The remineralization would continue during the gargling of the solution in the mouth for a period time, such as 30-sec to a minute. Besides the peptides and ions as active ingredients, other ingredients are introduced to freshen the breath and combating the halitosis. Mouth wash is designed to combat dry mouth/xerostomia as a lubricant and breath refresher with added generic ingredients.

Remineralizing Dental Whitening Strips—Peptide-guided Whitening Strips are designed to have two 50-500 micrometers-thick layers of gels in contact with the other, one contains peptide and the other strip contains the ions. The whitening strips have self-adhesive properties. The strips are durable within the saliva but leaky allowing the ions in one and the peptide in the other to be released from the strips and mix to form the remineralizing layer on the surface of the teeth. The thickness of the strip is designed to allow a certain concentration of the ions and the peptides to facilitate the formation of remineralized layer with a predetermined thickness at the site of the application to the teeth surface. The strips are flexible to be bent over the tooth edge covering both the facing surface as well as the inside surface. The strips have mineralizing as well as penetration capability into the exposed dental tubules, to treat dental hypersensitivity.

Whitening Gel, Paste, Powder, or Liquid Formulation in Dental Tray—The dental trays have physical and mechanical characteristics similar to the currently available dental trays that are used for a wide variety of purposes, e.g., used against grinding teeth, protecting teeth against impact as athletic guards, The-dental trays are made of thermoset or thermoplastic materials, depending on the purpose of use. Thermoplastics conform into the shape of the teeth, covering the surface, e.g., during the daytime or nighttime uses, protecting the remineralized layer already formed with the applications of other remineralizing products, such as gel, strip or varnish. Inside surface of the thermoplastic dental tray has a thin remineralizing gel layer containing peptide and ions. In the case of thermoset dental tray, the shape is made such that not only it conforms the 3D structure of the upper and lower set of teeth, but also has provisions at the caries site containing a pocket of mineralizing gel with specific volume. The mineralizing gel has two components: one has peptide and the other has calcium/phosphate ions, separated with a permeable membrane that breaks upon mechanical compression, e.g., during the mastication action of the teeth. Mineralization is confined into the areas along the inside surface of the dental tray whose positions are defined by the location of the caries on the surface of teeth and volume defined by the size of the caries that has the negative impression on the inside surface of the tray. Under the guidance of the dental professional or dental clinician, the caries can be monitored until fully remineralized and the tissue is fully repaired.

Remineralizing Dental Varnish—These have dual component design with the same inactive ingredients as the dental varnishes available commercially but containing no fluoride ions. Each of the two varnishes contain either the remineralizing peptide or the calcium and phosphate ions, the active ingredients for the formation of the new mineral on the tooth surface. The varnishes are sticky enough to be painted directly onto the root of the teeth, especially effective after tooth cleaning procedure when the roots are most susceptible to sensitivity. The remineralizing dental varnish has not only the capability of forming mineral but also the mineral penetrates into any exposed dental tubules at the root of the teeth.

Chimeric Peptide Design into the Dental Products: Remineralizing peptides can be designed to have dual functionality; one having remineralizing characteristics, and the other, e.g., antimicrobial property. A member of the anti-microbial peptide(s) (ATPs) is conjugated with the remineralizing peptides using a flexible linker, such as GGG in between. The chimeric peptide is then incorporated into one member of the dual-components in the formulations and products described above. All of the other materials and methods would be the same in the dual component design of the products. While one component includes the chimeric peptide as the active component, the other includes the precursor ions incorporated into it, and the inactive ingredients in both components.

Such products may further include chewing gums, lubricants with remineralizing (peptide) and pH balancing (Ca and P) mouthwash, including mouthwash with dual effect to overcome halitosis, mouthwash for dry mouth patients, toothpaste, for kids remineralizing candies for school lunchboxes after lunch as preventive measure against caries, etc.

Remineralizing Mouth Wash

The components of the double-barrel remineralizing mouth wash in each container were formulated separately using excipients as detailed in Table 7 below.

TABLE 7

The ingredients contained in the mouthwash formulations and their amounts.

| Ingredients | Barrel 1 Amount (mg) | Barrel 2 Amount (mg) |
| --- | --- | --- |
| shADP5 Peptide | 125.0 | 125.0 |
| $CaCl_2 \cdot H_2O$ | 0.0 | 70.0 |
| $KH_2PO_4$ | 30.0 | 0.0 |
| $K_2HPO_4$ | 10.0 | 0.0 |
| Sodium Benzoate | 1.0 | 1.0 |
| Sorbitol | 4.0 | 4.0 |
| Peppermint | 5.0 | 5.0 |
| Water | 100.0 | 100.0 |

The remineralization efficacy of the mouth wash was tested on extracted human enamel. With this aim, a tooth specimen was mounted onto metal stubs and the peptide containing mouth wash (barrel-1) was applied onto tooth surface using a droplet dispenser. 50 microliters of solution were dripped onto tooth surface with an approximately 60 degrees angle so that it can slide through the tooth surface with a contact time less than 1 seconds where the retention time of the remaining liquid on the tooth surface was 4 seconds. The procedure was repeated 3 times to establish 10-12 seconds of contact time between the ingredients of the peptide containing barrel-1 and tooth surface. Next, the calcium and phosphate containing mouth wash (barrel-2) was applied onto tooth surface using a droplet dispenser. 50 microliters of solution were dripped onto tooth surface with an approximately 60 degrees angle so that it can slide through the tooth surface with a contact time less than 1 seconds where the retention time of the remaining liquid on the tooth surface was 4 seconds. The procedure was repeated 7 times to establish 20 seconds of contact time between the ingredients of the peptide containing barrel-2 and the tooth surface. Following the remineralization treatment, the tooth specimen was drip rinsed with artificial saliva followed by deionized water and prepared for scanning electron microscopy analysis. Samples were fractured in a direction perpendicular to treatment surface and coated with gold. Imaging was performed under 10 kV starting current.

Figure 13:
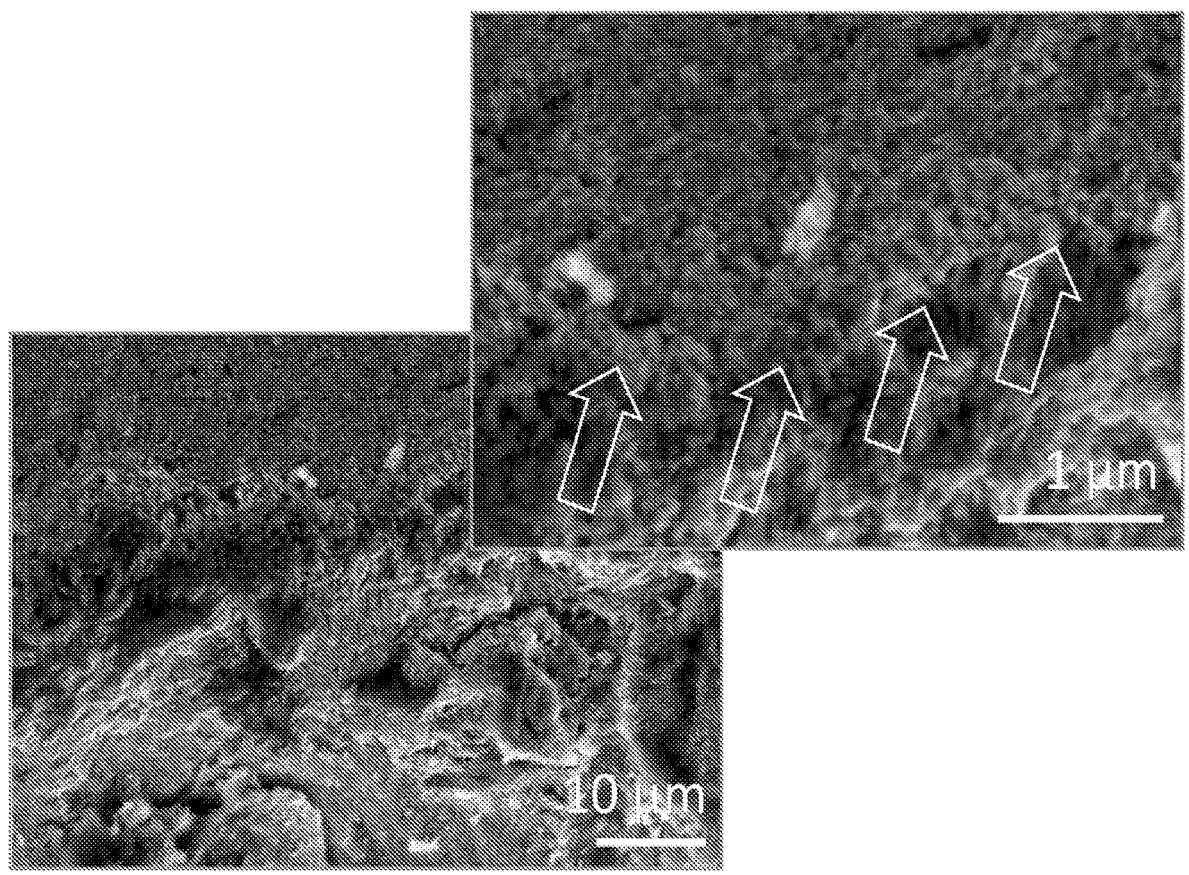
FIG. 13. Representative SEM images taken after one round of mouth wash treatment on human enamel. Arrows point out the newly formed mineral layer.

A continuous mineral layer with plate-like crystals was formed on the enamel. The calculated thickness of the newly formed mineral layer was measured to be 300±100 nanometer as a result of single round of mouth wash treatment on extracted human teeth (FIG. 13).

Remineralizing Dental Strips

Figure 20:
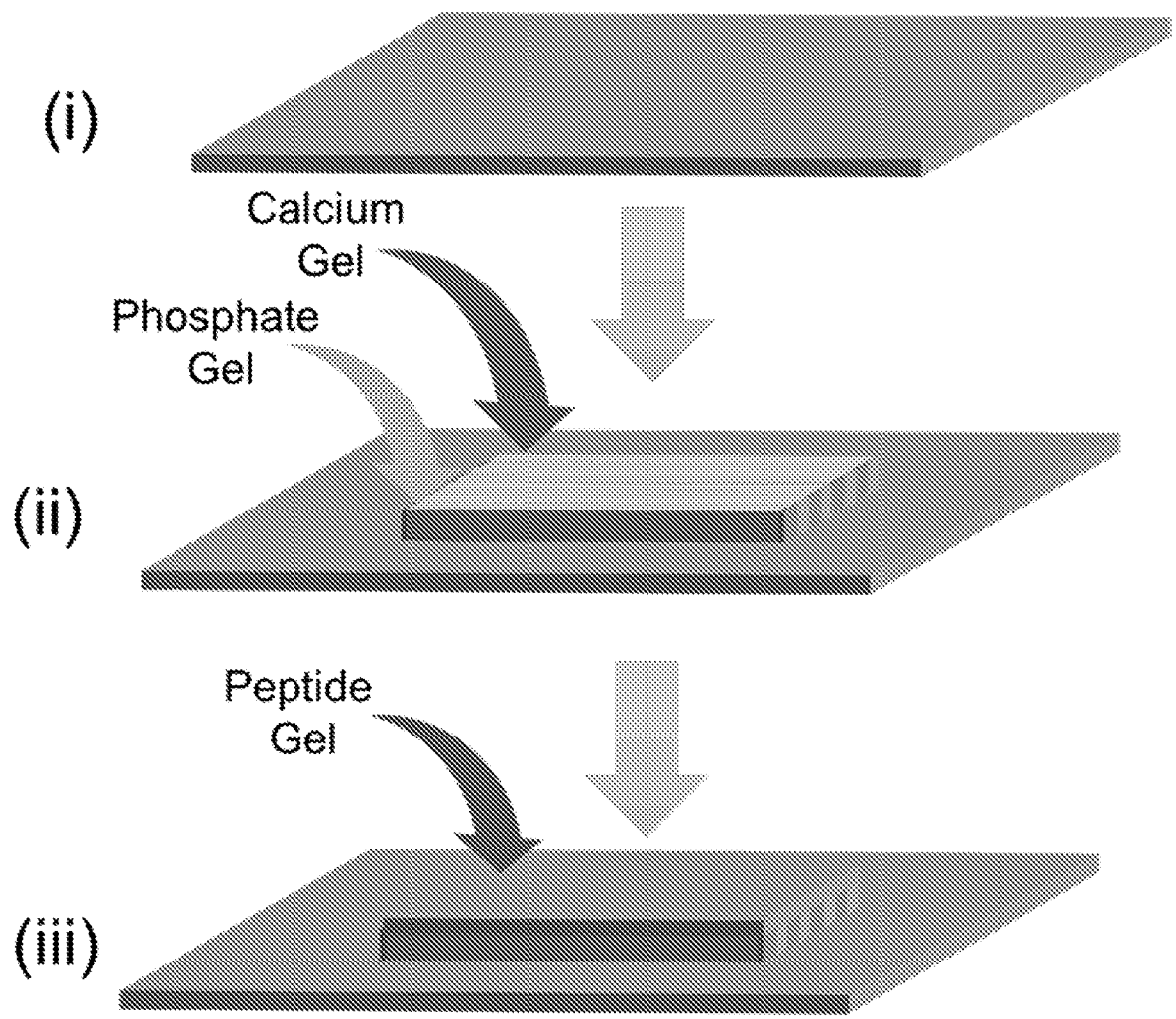
FIG. 20. Schematic representation of exemplary dental remineralizing and whitening strips containing triplet gel applied to the tooth surface.

The components of the double-layer remineralizing strip are formulated separately using different amounts of excipients. Active ingredient (peptide) in the first layer was mixed with equal concentration of calcium ions, sweeteners in the form of sorbitol, xylitol, mint and other types of plant flavors, thickener in the form of propylene glycol, cellulose gum and glycerol and surfactant in the form of simethicone. See Table 8 for specific components of each strip. A peptide layer is provided, with calcium ion source-containing layers and potassium ion source-containing layers alternating (see FIG. 20).

TABLE 8

The ingredients contained in the remineralized strip and their relative amounts.

| Ingredients | Peptide Formulation Weight % | Ca-gel formulation Weight % | Phospate-gel formulation Weight % |
|---|---|---|---|
| 24 mM Tris buffer, pH 7.4 containing: 1.6 mM shADP5 (active Ingredient) | 40.0 | 0.0 | 0.0 |
| 24 mM Tris buffer, pH 7.4 containing, 960 mM CaCl2•2H2O (Active Ingredient) | 0.0 | 40.0 | 0.0 |
| 24 mM Tris buffer, pH 7.4 containing, 576 mM $K_2HPO_4$ (Active Ingredient) | 0.0 | 0.0 | 40.0 |
| Potassium sorbate (preservative) | 0.5 | 0.5 | 0.5 |
| Propylene Glycol (PPG) (Thickener/Humectant) | 3.5 | 3.5 | 3.5 |
| Glycerol (Glycerin) (Thickener/humectant) | 12.0 | 12.0 | 12.0 |
| Cellulose Gum (Sodium Carboxymethyl Cellulose) | 15.0 | 15.0 | 15.0 |
| D-Sorbitol, 60% aqueous solution (Flavor) | 29.0 | 29.0 | 29.0 |

The remineralizing strip was manufactured in double layer architecture by mixing ingredients using water and glycerol as main solvents. Calcium containing second (bottom) layer was placed onto a plastic film surface and covered by a thin layer of cellulose gum gel to provide separation. Next, peptide containing gel was layered down on the film surface. The thickness ratio between the bottom and top gels were kept as 2:1 to provide optimum active ingredient delivery.

The remineralization efficacy of the oral strip was tested on extracted human enamel. A tooth specimen was mounted onto metal stubs and wetted with artificial saliva. The double-layer strip was placed onto the tooth surface and kept for 30 minutes for remineralization to take place. Following the remineralization treatment, the tooth specimen was drip rinsed with artificial saliva followed by deionized water and prepared for scanning electron microscopy analysis. Samples were fractured in direction perpendicular to treatment surface and coated with gold. Imaging was performed under 10 kV starting current.

A continuous mineral layer with plate-like crystals was formed on the enamel (data not shown). The calculated thickness of the newly formed mineral layer was measured to be 700±100 nanometers as a result of single round of dental strip treatment on extracted human teeth.

Remineralizing peptides can be designed to have dual functionality; one having remineralizing characteristics, and the other, e.g., antimicrobial property. A member of the anti-microbial peptide(s) (AMPs) can be conjugated with the remineralizing peptides using a flexible linker, such as GGG in between. The chimeric peptide can then then incorporated into one member of the dual-components in the formulations and products described herein. All of the other materials and methods would be the same in the dual component design of the products. While one component includes the chimeric peptide as the active component, the other includes the precursor ions incorporated into it, and the inactive ingredients in both components.

An antimicrobial remineralization peptide was constructed by conjugating an shADP5 remineralizing peptide with an antimicrobial peptide LKLLKKLLKLLKKL (SEQ ID NO:28). A flexible glycine-glycine-glycine residue was placed in between so that each compartment in chimeric peptide can be freely exposed to the environment. The components of the double-barrel remineralizing antimicrobial gel were formulated separately using different amounts of excipients.

A remineralizing gel was manufactured in two strip architecture by mixing ingredients using water and glycerol as main solvents as shown in Table 9. Each strip is the same, with the exception that the calcium ion source ($CaCl_2$)-containing strip and the potassium ion source ($K_2HPO_4$)-containing strip are arranged in alternating fashion within a single layer (see FIG. 20).

TABLE 9

| | Weight % |
|---|---|
| Active Ingredient: | |
| 24 mM Tris buffer, pH 7.4 containing: 1.6 mM chimeric antimicrobial peptide, 960 mM $CaCl_2$, or 575 mM $K_2HPO_4$ | 50 |
| Preservative: | |
| Potassium sorbate | 0.5 |
| Thickener/Humectant: | |
| Propylene Glycol (PPG) | 3 |
| Glycerol (Glycerin) | 15 |
| Cellulose Gum (Sodium Carboxymethyl Cellulose) | 2 |
| Sweetener/Flavor: | |
| Sorbital, 60% aqueous solution | 29 |
| Surfactant: | |
| Simethicone (antifoam) | 0.5 |

The remineralization efficacy of the oral strip was tested on extracted human enamel. A tooth specimen was mounted onto metal stubs. Using a toothpick, the peptide gel formulation was applied to the tooth surface to cover the affected enamel and incubated at 37° C. for 10 minutes. Then, the second gel was placed onto pretreated area and waited to insure that the solution was well enough mixed for mineralization to occur. The anti-microbial gel was kept for 50 minutes for remineralization to take place. Following the remineralization treatment, tooth specimen was drip rinsed with artificial saliva followed by deionized water and prepared for scanning electron microscopy analysis. Samples were fractured in a direction perpendicular to treatment surface and coated with gold. Imaging was performed under 10 kV starting current.

The remineralized specimen was soaked into *S. mutans* culture ($OD_{600}$:0.5) and kept for 24 hours for bacterial colonization. Specimens were then placed into Live/Dead bacteria assay solution and visualized with confocal microscopy.

A continuous mineral layer with plate-like crystals was formed on the enamel. The calculated thickness of the newly formed mineral layer was measured to be 1.2±0.1 micrometer as a result of single round of dental strip with chimeric anti-microbial treatment on extracted human teeth.

Confocal fluorescent imaging revealed that *Streptococcus mutans* colonization on newly formed mineral was reduced by 95% compared to unmineralized (untreated) enamel surface, indicating the efficacy of antimicrobial activity of peptide embedded in newly formed mineral.

Remineralizing Gel & Varnish Formulations

Three separate gel formulations were prepared, which contained aqueous solutions of shADP5 peptide of >95% purity, ionic Ca, or ionic $PO_4$. The three shared the same chemical constituents otherwise specific to gel or varnish formulations. The primary difference between gel and varnish is the use of rosin in place of methyl cellulose in the varnish formulation. Specific ingredients are listed in Tables 10 and 11 for gel and varnish, respectively.

TABLE 10

Base gel formulation ingredients list for gel formulation.

| | Weight % |
|---|---|
| Active Ingredient: | |
| 24 mM Tris buffer, pH 7.4 containing:<br>1.6 mM ADP5,<br>960 mM $CaCl_2$,<br>or 575 mM $K_2HPO_4$ | 50 |
| Preservative: | |
| Potassium sorbate | 0.5 |
| Thickener/Humectant: | |
| Propylene Glycol (PPG) | 3 |
| Glycerol (Glycerin) | 15 |
| Cellulose Gum (Sodium Carboxymethyl Cellulose) | 2 |
| Sweetener/Flavor: | |
| Sorbital, 60% aqueous solution | 29 |
| Surfactant: | |
| Simethicone (antifoam) | 0.5 |

TABLE 11

Base gel formulation ingredients list for varnish formulation.

| | Weight % |
|---|---|
| Active Ingredient: | |
| 24 mM Tris buffer, pH 7.4 containing:<br>1.6 mM ADP5,<br>960 mM $CaCl_2$,<br>or 575 mM $K_2HPO_4$ | 50 |
| Preservative: | |
| Potassium sorbate | 0.5 |
| Thickener/Humectant: | |
| Propylene Glycol (PPG) | 3 |
| Glycerol (Glycerin) | 15 |
| Rosin | 2 |
| Sweetener/Flavor: | |
| Sorbital, 60% aqueous solution | 29 |
| Surfactant: | |
| Simethicone (antifoam) | 0.5 |

The remineralizing gel was manufactured starting with preparing 1.6 mM of ADP5, 960 mM of $CaCl_2$, and 575 mM of $K_2HPO_4$ in 24 mM Tris-HCl buffer with final pH adjusted to 7.4. Separately the gel formulation mixture was prepared by mixing potassium sorbate, propylene glycol, glycerol, 60% aqueous sorbital, simethicone and cellulose gum using a low speed propeller mixer at 50 C. After mixture returned to room temperature, final formulations were made by mixing 50-50 solutions of 1.6 mM of ADP5, 960 mM of $CaCl_2$, or 575 mM of $K_2HPO_4$ with the gel formulation mixture using a low speed propeller mixer. For storage, gels containing each active ingredient were stored separate syringes to prevent premature mineralization reactions.

The varnish manufacturing started with preparing 1.6 mM of ADP5, 960 mM of $CaCl_2$, and 575 mM of $K_2HPO_4$ in 24 mM Tris-HCl buffer with final pH adjusted to 7.4. Separately the varnish formulation mixture was prepared by mixing potassium sorbate, propylene glycol, glycerol, 60% aqueous sorbital, simethicone and rosin using a low speed propeller mixer at 60 C. After mixture returned to room temperature, final formulations were made by mixing 50-50 solutions of 1.6 mM of ADP5, 960 mM of $CaCl_2$, or 575 mM of $K_2HPO_4$ with the gel formulation mixture using a low speed propeller mixer combined with up and down movement of the rotating propeller during mixing. For storage, gels containing each active ingredient were sealed separate squeezable pouches to prevent premature mineralization reactions.

Human teeth were collected from anonymous patients at the University of Washington Dental Clinic. Animal teeth from Sprague-Dawley rats and Yucatan mini-pigs were collected after their terminal procedures per University of Washington IACUC approved protocols #3242-02 and #3393-03, respectively. Human teeth were stored disinfected by storing in 10% bleach for 24 hrs, rinsed by DI water, followed by storing 70% aqueous ethanol until use. All animal teeth were stored in 70% ethanol until use.

Artificial lesions on enamel were first created by etching with Ultraetch™ (Ultradent) which contained 33% phosphoric acid for 30 seconds following by jetted DI water rinsed for 30 seconds. Remineralization began by taking etched prepared sample and adding peptide gel formulation to cover the affected enamel surface, and incubating at 37° C. for 10 mins. Then, in a separate area equal amounts of the 960 mM $CaCl_2$ or 576 mM $KH_2PO_4$ gel formulation were mixed together to insure that the solution was well enough mixed for mineralization to occur. After incubation, peptide gel formulation was swabbed off as possible and equal amounts of the Ca and PO4 gel formulations were applied onto the affected tooth surface. Incubation with the mixed Ca+PO4 gel formulations was carried out at 37 C for 2 hours. At the end of the incubation, the teeth were transferred into a container with simulated saliva and incubated at 37 C for 21 hours until the next remineralization round. This procedure was repeated 7 times.

Mineral layers were characterized by scanning electron microscopy JEOL JSM 6010 imaging at 10 kV in cross-section. Chemical composition was measured with the onboard EDXS system. Hardness and elastic moduli of mineral layers as well as underlying tooth tissues were measured using a Hysitron Triboscope™ Nanoindentation system attached to Park AFM system.

Formulation Characteristics

Figure 14:
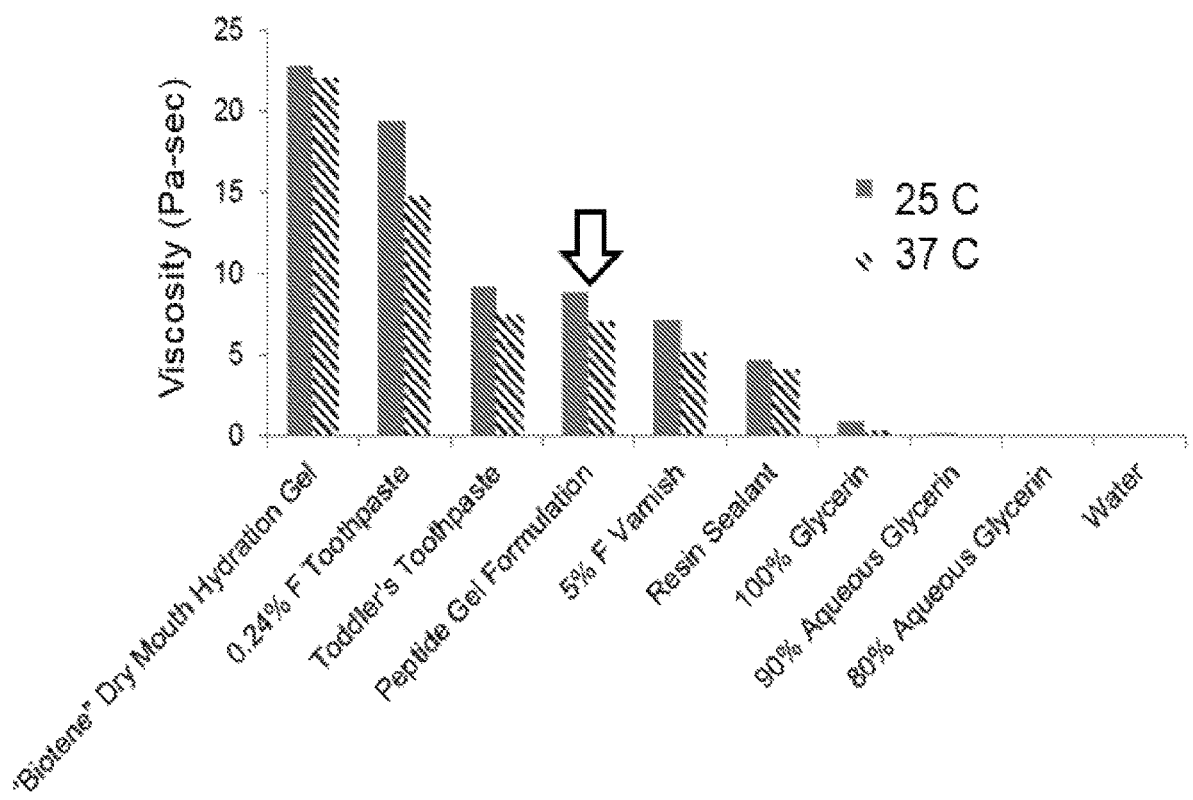
FIG. 14. Viscosity of peptide gel formulation relative to commercial dental products and aqueous solutions of gylcerin/water.

The utility of developing a gel formulation is to enable localized treatments the affected tooth surface. This is desirable in a clinical setting as well as in a home care treatment setting. Viscosity is a measure of resistance to flow, and therefore, an important parameter in dictating the degree of localization of the gel formulation. Viscosity was measure against various commercial dental products such as toothpaste, dry mouth get, F varnish (See FIG. 14). The viscosity of the gel formulation was comparable to toddler's tooth paste. This viscosity was high enough to enable localization of the develop gel formulation on tooth surface.

Figure 15:
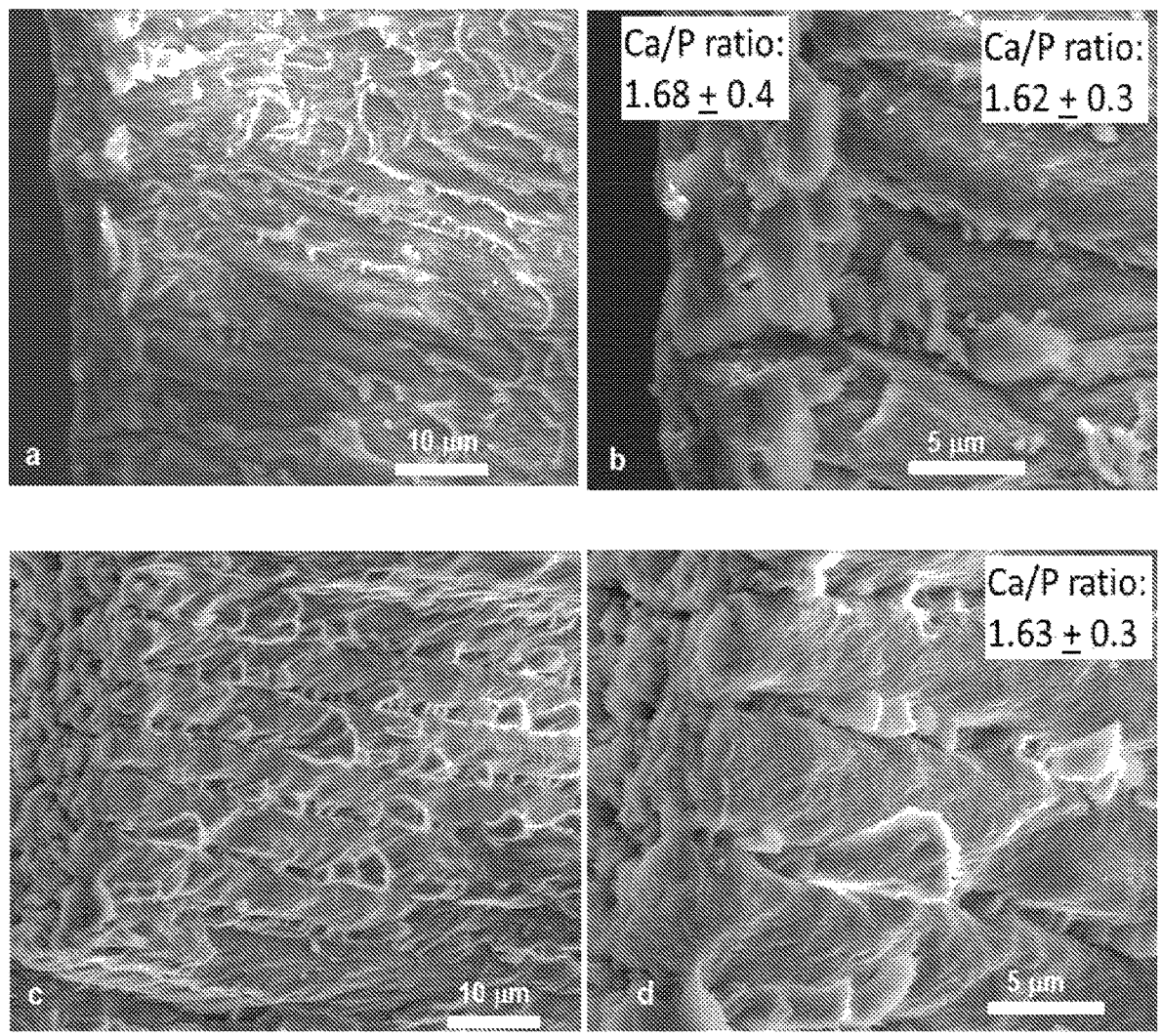
FIG. 15. Mineralization of artificial lesions on enamel of extracted human teeth using gel formulations with peptide (a & b) and without (c & d).

Remineralization was performed on teeth with artificial lesions created by etching with UltraEtch™, a 33% phosphoric acid gel. On extracted human teeth, a mineral layer of 5 um thick was established after 10 minutes of peptide formulation treatment with the addition of 2 hours of Ca/$PO_4$ gel formulation, all incubated at 37 C (FIGS. 15a and b). By contrast, those that were treated with Ca/$PO_4$ gel formulation only, a bare etched enamel surface resulted, indicating no measurable remineralization occurred (FIG. 15c and d). Similarly, comparable mineral layers resulted in rat and porcine enamel(data not shown). These results demonstrated that the peptide gel formulation when used along with Ca/$PO_4$ gel formulation resulted in remineralization by means of adding mineral layer to the tooth surface.

Mechanical Properties

Mechanical properties were measured by nano-indentation in cross-section of the new mineral layer and the underlying enamel. Hardness of the remineralized layers were ⅓ of that of the underlying enamel while the elastic moduli was approximately ¼. The lower hardness and elastic moduli of the mineral layer suggested incorporation of the organic content from the gel formulation. The hardness and elastic modulus transition from mineral layer to underlying enamel was decreased.

TABLE 12

Values of Hardness and Elastic Moduli

|  | Hardness (H, GPa) | Elastic Modulus (E, GPa) |
|---|---|---|
| Human Teeth: |  |  |
| Peptide enabled mineral layer | 1.2 ± 0.7 | 21 ± 5 |
| Underlying enamel | 3.3 ± 0.6 | 89 ± 6 |
| Rat Teeth: |  |  |
| Peptide enabled mineral layer | 1.0 ± 0.6 | 22 ± 7 |
| Underlying enamel | 3.2 ± 0.7 | 82 ± 3 |
| Pig Teeth: |  |  |
| Peptide enabled mineral layer | 1.1 ± 0.6 | 18 ± 8 |
| Underlying enamel | 3.4 ± 0.5 | 83 ± 3 |

Remineralizing Toothpaste Formulations

Figure 21:
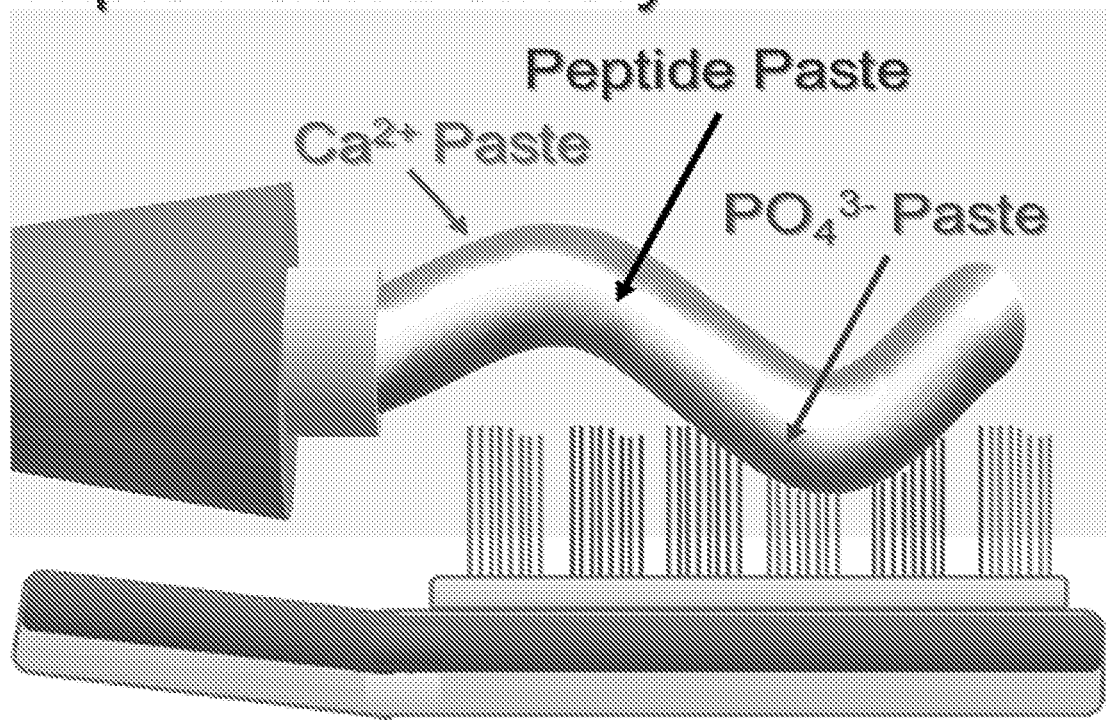
FIG. 21. Schematic representation of an exemplary three-paste toothpaste of the disclosure.

Remineralizing toothpaste involved incorporation of active ingredients, shADP5, ionic calcium and ionic phosphate into a specific formulated toothpaste substance to achieve a viscosity high enough for spreading by toothbrush onto tooth surface without excess run-off. The time required for mineralization to take place on tooth surface is 2 minutes (See FIG. 21). The final toothpaste formulation has the following unique characteristics:

1. Contain active ingredients, shADP5, ionic calcium and ionic phosphate.
2. The inactive ingredients in the toothpaste formulation are designed to have the minimum number of constituents while achieving a viscosity range of 10-12 Pascal-seconds (Pa-sec) and providing flavor.
3. The toothpaste formulation uses the base gel formulation but has higher viscosity. Inorganic particles are limited/eliminated as part of the thickening agent so that the new mineral layer formed on tooth surface is not disturbed.
4. 3 separate pastes containing shADP5, ionic calcium and ionic phosphate, respectively, are stored in a squeezable or pump action toothpaste tube as individual strips of paste spanning the length of the tube and separated by layer of neutral paste (paste made of inactive ingredients only) or a membrane acting as a diffusion barrier.
5. Ionic fluoride can be added with ionic phosphate containing gel as the $4^{th}$ active ingredient.

Three separate gel formulations were prepared, which contained aqueous solutions of shADP5 peptide of >95% purity, ionic Ca, or ionic $PO_4$, respectively. The three shared the same chemical constituents otherwise in paste formulations. Specific ingredients are listed in Table 13.

TABLE 24

Base gel formulation ingredients list for toothpaste formulation.

|  | Weight % |
|---|---|
| Active Ingredient: |  |
| 24 mM Tris buffer, pH 7.4 containing: 1.6 mM shADP5, 960 mM $CaCl_2$, | 50 |
| Preservative: |  |
| Potassium sorbate | 0.5 |
| Thickener/Humectant: |  |
| Propylene Glycol (PPG) | 3 |
| Glycerol (Glycerin) | 11 |
| Cellulose Gum (Sodium Carboxymethyl Cellulose) | 6 |
| Sweetener/Flavor: |  |
| Sorbital, 60% aqueous solution | 29 |
| Surfactant: |  |
| Simethicone (antifoam) | 0.5 |

The remineralizing gel was manufactured starting with preparing 1.6 mM of ADP5, 960 mM of $CaCl_2$, and 575 mM of $K_2HPO_4$ in 24 mM Tris-HCl buffer with final pH adjusted to 7.4. Separately the gel formulation mixture was prepared by mixing potassium sorbate, propylene glycol, glycerol, 60% aqueous sorbital, simethicone and cellulose gum using a low speed propeller mixer at 50 C. After mixture returned to room temperature, final formulations were made by mixing 50-50 solutions of 1.6 mM of ADP5, 960 mM of $CaCl_2$, or 575 mM of $K_2HPO_4$ with the gel formulation mixture using a low speed propeller mixer. 3 separate pastes containing shADP5, ionic calcium and ionic phosphate are stored in a squeezable or pump action toothpaste tube as individual strips of paste spanning the length of the tube and separated by layer of neutral paste (paste made of inactive ingredients only) or a membrane acting as a diffusion barrier.

Figure 16:
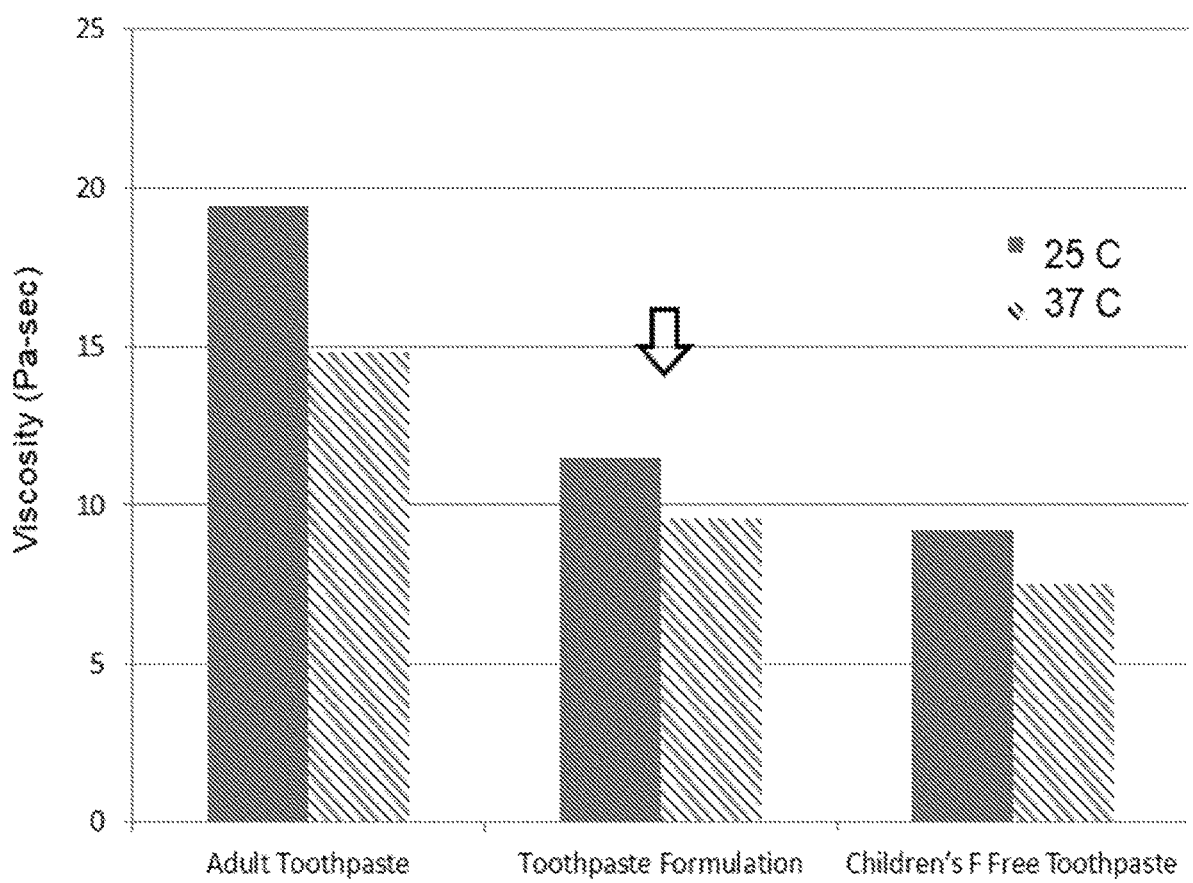
FIG. 16. Viscosity of toothpaste formulation relative to generic commercial toothpaste.

The viscosity characteristics of the formulation are shown in FIG. 16.

For all formulations, ionic fluoride can be added as the $4^{th}$ active ingredient and is mixed in the range of 1000 ppm to 5000 ppm of ionic fluoride with the $K_2HPO_4$ containing formulation. For example Table 14 lists the formulation composition for the gel formulation.

TABLE 14

Gel formulation with fluorides as the 4$^{th}$ active ingredient.

Figure 17:
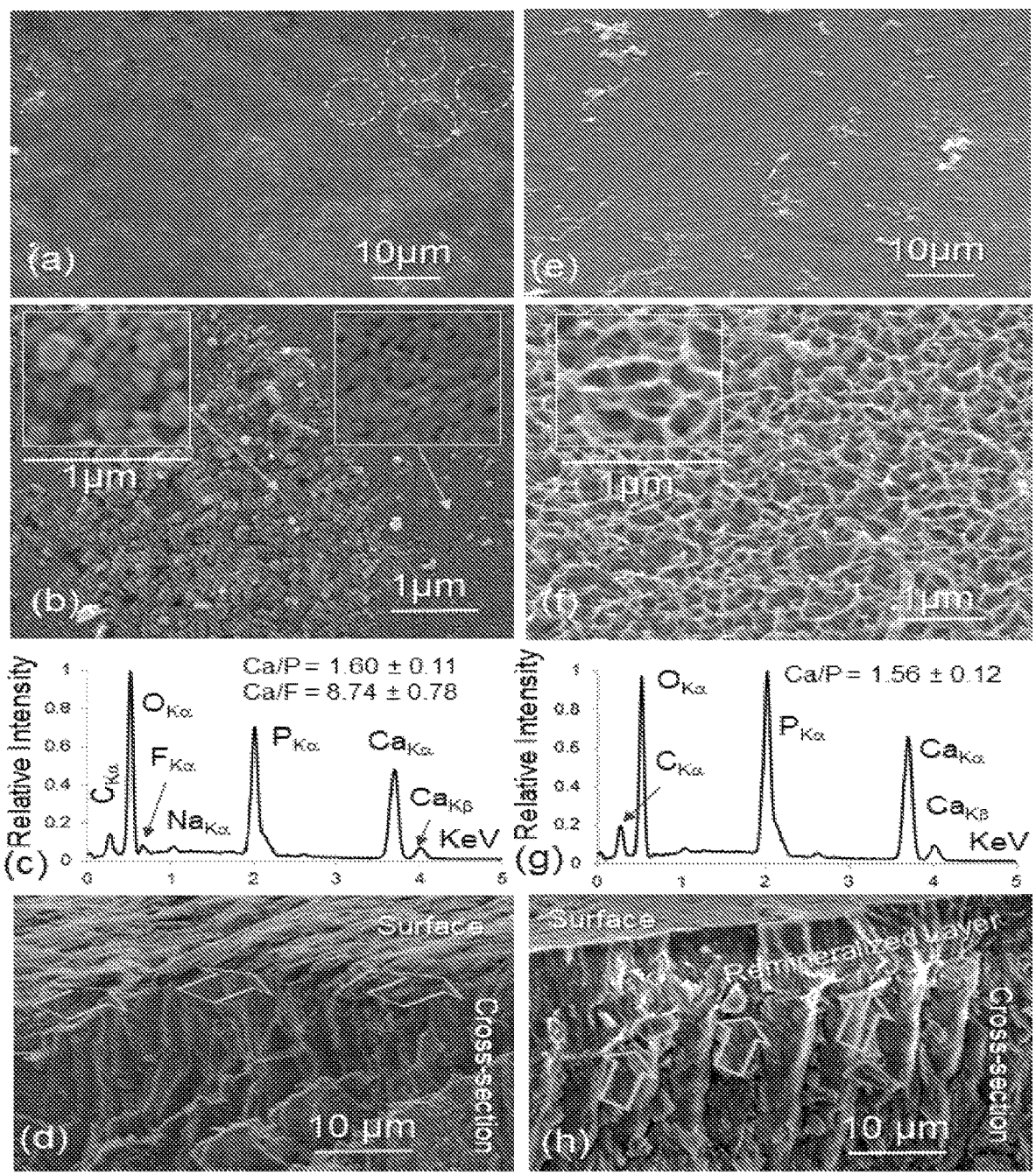
FIG. 17. Face-on (a,b) and edge-on (d) SEM images and EDXS analyses (c) of Group 5: shADP5+1100 ppm F+$Ca^{2+}$/$PO_4^{3-}$. Insets in 4b show loosely crystallized regions of accumulated 100-nm dia. spherical nanoparticles on the surface. Face-on (e,f) and edge-on (h) SEM images and EDXS analysis (g) of Group 6: shADP5+$Ca^{2+}$/$PO_4^{3-}$. Inset 4f displays a highly uniform, plate-like HAp crystallites within newly formed (h) mineral layer in shADP5+$Ca^{2+}$/$PO_4^{3-}$ treatment. The inset panels are 1 μm×1 μm. Wide arrows in (d) and (h) indicate the boundary between the new layer and original tooth surface.

| | Weight % |
|---|---|
| Active Ingredient: | |
| 24 mM Tris buffer, pH 7.4 containing:<br>1.6 mM shADP5,<br>960 mM CaCl$_2$,<br>or 575 mM K$_2$HPO$_4$ + 1100 ppm NaF | 50 |
| Preservative: | |
| Potassium sorbate | 0.5 |
| Thickener/Humectant: | |
| Propylene Glycol (PPG) | 3 |
| Glycerol (Glycerin) | 15 |
| Cellulose Gum (Sodium Carboxymethyl Cellulose) | 2 |
| Sweetener/Flavor: | |
| Sorbital, 60% aqueous solution | 29 |
| Surfactant: | |
| Simethicone (antifoam) | 0.5 | shADP5 enables the delivery of ionic fluoride delivery to the tooth surface. After the tooth surface was treated shADP5, ionic fluoride was delivered with ionic PO4. As shown in FIG. 17, fluoride was incorporated in the mineral layer as detected by energy dispersive X-ray spectroscopy (EDXS). See FIG. 17.

Active ingredients stored separately in their respective gel/varnish/toothpaste formulations is important in preventing premature mineralization reactions. In all formulations, the peptide is to be delivered first, then the ionic calcium/phosphate or ionic calcium/phosphate/fluoride are delivered second. Understanding the reaction time is useful to characterize the prescribed treatment time and procedure. To inform treatment protocol, an experiment was designed in which two drops of gels containing calcium and phosphate were mixed with peptide gel and placed next each other on a glass slide close enough that upon subsequent spreading of the two droplets, they would come to contact with each other at their respective edges. Mineralization reactions were monitored visually be observing parts of the gels turning from clear (unreacted) to white (reacted).

Figure 18:
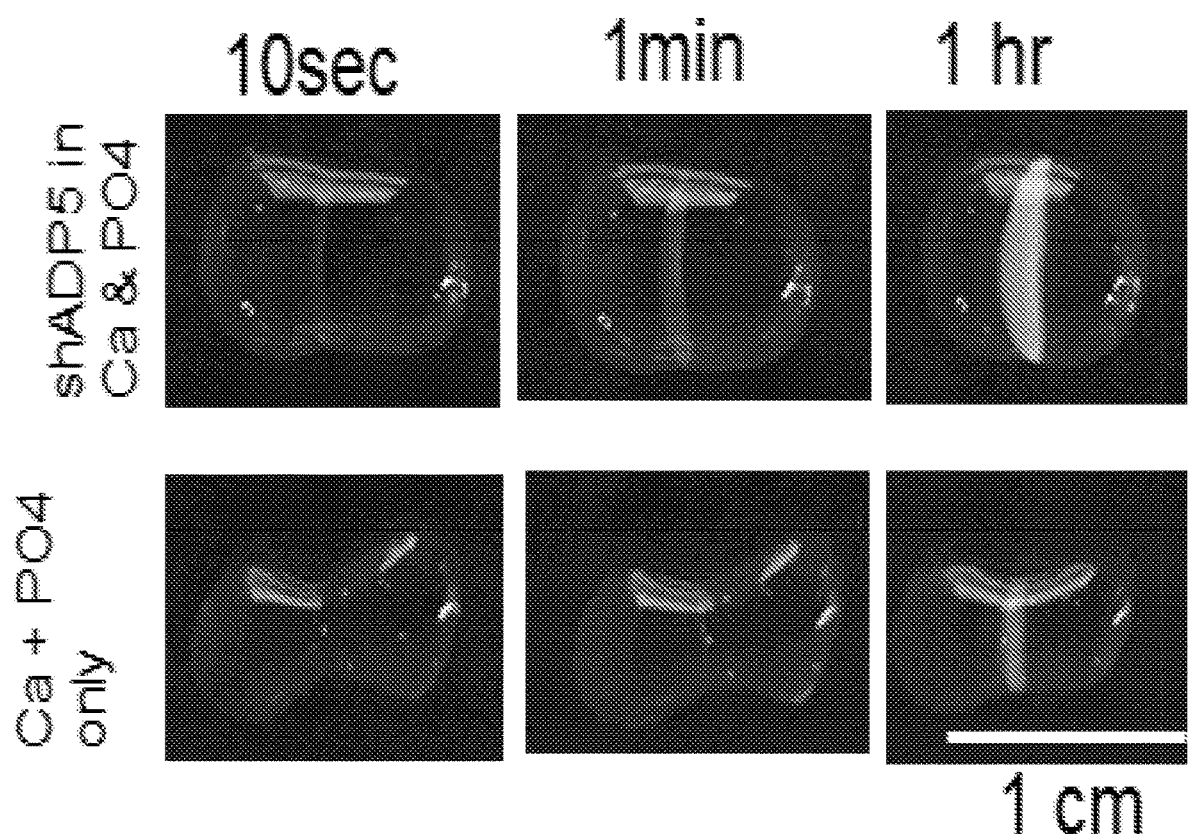
FIG. 18. Visual observation of diffusion and reaction of cationic and anionic gels with vs. without peptide. The wide band in the center indicates extent of the mineralization reaction.
Figure 19:
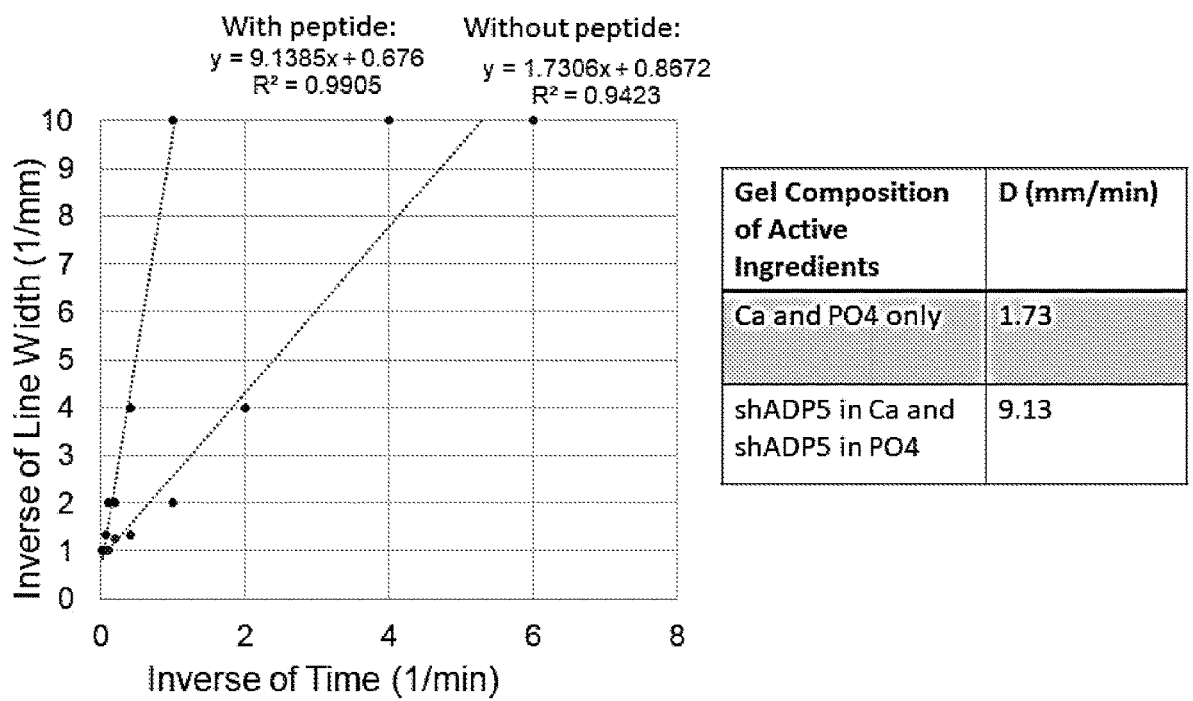
FIG. 19. Graph showing diffusion coefficient derived for gels with and without peptide.

Using the gel formulation as an example, with the incorporation of shADP5, the reaction with clearly more extensive than that without shADP5 as revealed in FIG. 18. Furthermore, a diffusion constant based on the law of diffusion, the width of the white band as seen in FIG. 18 was recorded with respect to time. Then the inverses of both quantities were taken to enable the determination of the diffusion constant based on the following equation: $1/t=D(1/x)$, where t is time, x is the width of reacted mineral (appear as white in FIG. 18) and D is the diffusion constant in units of mm/min. Shown in FIG. 19 is an example of the derived diffusion constants.

In summary, SEM analysis demonstrated that after a single round of lozenge treatment, ~1-2 μm thick continuous mineral layer with plate-like crystals forms on the surface of stained enamel. The successful formation of mineral layer indicates that developed lozenge is an effective product in transferring and enabling the peptide-guided remineralization in artificial saliva. As a whitening product, in the next step, the whitening performance of the lozenge was tested by remineralizing the inherently stained human teeth. Lozenge treatment improved the whiteness of teeth by ΔE=5.56. In the next step, the whitening performance of the lozenge was compared with commercial products. While the lozenge demonstrated whitening effect as effective as clinically used Whitening Gels (40% HP), it is 3 times more effective than OTC Whitening Strips. While the commercial products chemically etch away the mineral from the teeth and creates a rough tooth surface, the whitening lozenge adds mineral layer to it, creating a thicker and healthier enamel on the surface of teeth. The lozenge and other products described herein provide both therapeutic (remineralizing) and cosmetic (whitening) benefits. The whitening performance of the lozenge is an improvement over the existing dental whitening products.

REFERENCES

1. Alkhatib, M., R. Holt, and R. Bedi, *Prevalence of self-assessed tooth discolouration in the United Kingdom*. Journal of dentistry, 2004. 32(7): p. 561-566.
2. Odioso, L., R. Gibb, and R. Gerlach, *Impact of demographic, behavioral, and dental care utilization parameters on tooth color and personal satisfaction*. Compendium of continuing education in dentistry. (Jamesburg, N.J.: 1995). Supplement, 2000(29): p. S35-41; quiz S43.
3. Qualtrough, A. and F. Burke, *A look at dental esthetics*. Quintessence international, 1994. 25(1).
4. NATHOO, S. A., *The chemistry and mechanisms of extrinsic and intrinsic discoloration*. The Journal of the American Dental Association, 1997. 128: p. 6S-10S.
5. Sulieman, M., *An overview of tooth discoloration: extrinsic, intrinsic and internalized stains*. Dental update, 2005. 32(8): p. 463-4, 466-8, 471.
6. Sánchez, A. R., R. S. Rogers, and P. J. Sheridan, *Tetracycline and other tetracycline- derivative staining of the teeth and oral cavity*. International journal of dermatology, 2004. 43(10): p. 709-715.
7. Sundell, S. and G. Koch, *Hereditary amelogenesis imperfecta. I. Epidemiology and clinical classification in a Swedish child population*. Swedish Dental Journal, 1985. 9(4): p. 157-169.
8. Watanabe, K., et al., *Bilirubin pigmentation of human teeth caused by hyperbilirubinemia*. Journal of oral pathology & medicine, 1999. 28(3): p. 128-130.
9. Link, J., *Discolouration of the teeth in alkaptonuria and Parkinsonism*. Chron Omaha Dist Dent Soc, 1973. 36: p. 136.
10. Sulieman, M., et al., *The effect of hydrogen peroxide concentration on the outcome of tooth whitening: an in vitro study*. Journal of dentistry, 2004. 32(4): p. 295-299.
11. Pindborg, J. J., *Pathology of the dental hard tissues*. 1970.
12. Dahl, J. and U. Pallesen, *Tooth bleaching—a critical review of the biological aspects*. Critical Reviews in Oral Biology & Medicine, 2003. 14(4): p. 292-304.
13. Hein, D., et al., *In-office vital tooth bleaching—what do lights add?* Compendium of continuing education in dentistry (Jamesburg, N.J.: 1995), 2003. 24(4A): p. 340-352.
14. Luk, K., L. Tam, and M. Hubert, *Effect of light energy on peroxide tooth bleaching*. The Journal of the American Dental Association, 2004. 135(2): p. 194-201.
15. Chen, J.-h., et al., *Clinical evaluation of 546 tetracycline-stained teeth treated with porcelain laminate veneers*. Journal of dentistry, 2005. 33(1): p. 3-8.
16. Nixon, R., *Masking severely tetracycline-stained teeth with ceramic laminate veneers*. Practical periodontics and aesthetic dentistry: PPAD, 1996. 8(3): p. 227-35; quiz 237.

17. Arens, D. E., J. J. Rich, and H. J. Healey, *A practical method of bleaching tetracycline- stained teeth*. Oral Surgery, Oral Medicine, Oral Pathology, 1972. 34(5): p. 812-817.
18. Rodrigues, H., et al., *Mirror, mirror on the wall, who's the fairest of them all? A critical content analysis on medical tourism*. Tourism Management Perspectives, 2017. 24: p. 16-25.
19. Tredwin, C., et al., *Hydrogen peroxide tooth-whitening (bleaching) products: review of adverse effects and safety issues*. British dental journal, 2006. 200(7): p. 371-376.
20. Hanks, C., et al., *Cytotoxicity and dentin permeability of carbamide peroxide and hydrogen peroxide vital bleaching materials, in vitro*. Journal of Dental Research, 1993. 72(5): p. 931-938.
21. Gjorgievska, E. and J. W. Nicholson, *Prevention of enamel demineralization after tooth bleaching by bioactive glass incorporated into toothpaste*. Australian dental journal, 2011. 56(2): p. 193-200.
22. Gungormus, M., et al., *Cementomimetics-constructing a cementum-like biomineralized microlayer via amelogenin-derived peptides*. International Journal of Oral Science, 2012. 4(2): p. 69-77.
23. Matis, B., et al., *A clinical evaluation of two in-office bleaching regimens with and without tray bleaching*. Operative dentistry, 2009. 34(2): p. 142-149.

Example 2. Dental Hypersensitivity

Dental hypersensitivity (DH) is a common oral health condition affecting the majority of the adult population in the world. In the US alone, a total of approximately $10B is spent in treating hypersensitivity, in tooth paste, clinical pastes and gels, and mouthwashes. Despite enormous number of OTC and clinical products, the treatment options are limited and hypersensitivity still is the major cause of dental discomfort as well as the root cause of gingivitis and tooth loss. DH is caused by the exposure of dentin due to the demineralization of the protective cementum or enamel that covering tooth surface. When the dentinal tubules are exposed, nerve fibers in the pulp or pre-dentin are stimulated by the displacement of the fluid and report pain. The stimulus that triggers the onset of pain can be of thermal, chemical or mechanical origin. There is still no effective agent to completely resolve the patient's discomfort with DH. Over-the-counter products are commonly advised in the management of DH while toothpastes containing strontium, oxalate or potassium salts, or fluoride are recommended with limited efficacy to reduce the sensitivity from DH. Restorative materials using composite, glass ionomer or amalgam are adapted to treat the affected area with limited success.

Sample Preparation

Figure 6:
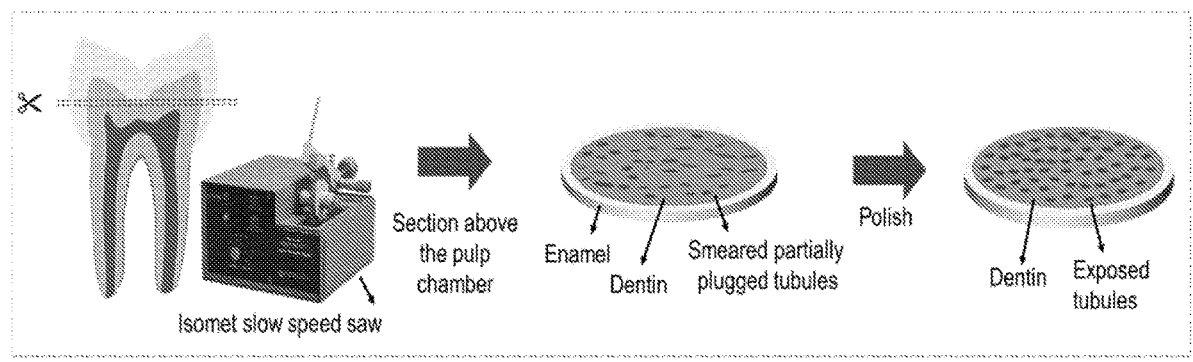
FIG. 6. Schematic representation of the preparation of exposed dentinal tubules
Figure 7:
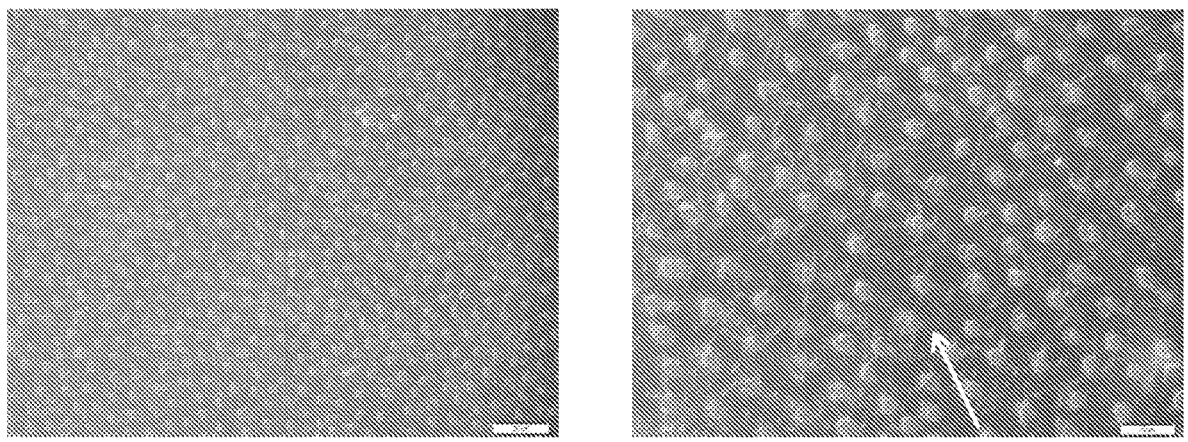
FIG. 7. Optical microscopy images showing polished dentin surface and circular tubules.

Extracted human molar teeth with little to no evidence of cavities or restorations were obtained from the University Of Washington School Of Dentistry. The goal of sample preparation is to mimic DH by removing the enamel of the tooth to expose the dentin tubules underneath. The general sample preparation process is shown in FIG. 6. The extracted tooth was mounted and cut using an Isomet slow speed saw. In order to get samples with the highest number of dentinal tubules in the correct orientation, extracted teeth were cut below the enamel and above the pulp chamber to obtain cylindrical discs of cervical dentin. The samples were then polished in order for the surface to have as many exposed tubules as possible. After polishing, samples were sonicated to remove any debris that remained on the surface. The goal was to optimize the occlusion and penetration of dentinal tubules with a new mineral layer, the orientation of the dentinal tubules in the remineralized samples was extremely important. In order to view the cross section of the sample to see mineral penetration in the tubules, the tubules need to be perpendicular to the surface or as close as possible. Therefore, optical microscopy was performed on the dentin surface of prepared samples before remineralization to ensure proper tubule alignment, as seen in FIG. 7. The circularity and relative high density of the tubules seen in FIG. 3 indicates tubules alignment. Optical microscopy was performed with an Olympus BX50 Lab Microscope with SC30 digital camera.

Peptide-Guided Remineralization

Figure 8:
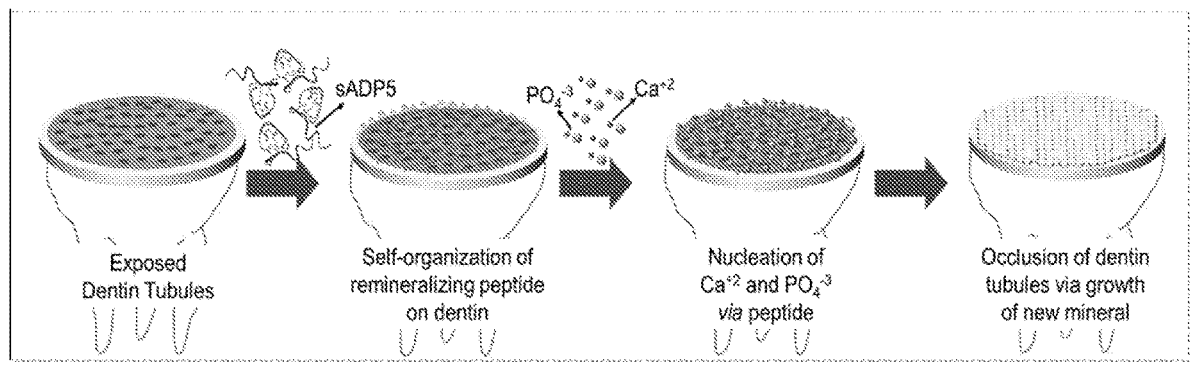
FIG. 8. Schematic representation of the peptide-guided remineralization treatment FIG. 9. Schematic representation of the thermal cycling process on 3 rounds remineralized sample.

Following sample preparation, samples were subjected to a peptide-guided remineralization process. The peptide used for the DH treatment was sADP5, or shortened amelogenin derived peptide 5. Samples were placed in 24 mM Tris buffer solution and centrifuged at 4,000 RPM for 5 minutes in order to hydrate the sample. Samples were then incubated in 0.75 mL of 0.8 mM peptide dissolved in 24 mM Tris buffer solution for 15 minutes at 37 C. Next, samples were placed into a solution containing equal parts of 24 mM Tris buffer solution, 9.6 mM $Ca^{2+}$ solution, and 5.76 $PO_4^{3-}$ solutions for 2 hours at 37 C. A schematic of the peptide-guided remineralization treatment is shown in FIG. 8. Samples are then rinsed with deionized water to remove deposited mineral formed in solution. The process described constitutes 1 round of the peptide-guided remineralization treatment. In order to visualize the mineral layer after continual treatment, samples were subjected to multiple rounds of the remineralization process. In addition to a control sample with no remineralization, samples were subjected to 1, 2, and 3 rounds of the peptide-guided remineralization process.

SEM Characterization

After the peptide-guided remineralization treatment, samples were prepared for scanning electron microscopy (SEM) characterization in order to view the morphology and thickness of the newly formed mineral layer. As a cross-section image was needed, notches were placed to the back side of samples using an Isomet slow speed saw during sample preparation and before the remineralization process. After the remineralization treatment, samples were rinsed with deionized water and let to dry overnight in a desiccator to remove any moisture. Samples were then carefully fractured along the notch into two separate pieces. One piece was then mounted on a thin aluminum SEM stub with the cross section parallel to the edge of the stub. The sample was then coated 5 nm thick layer of gold in order to be imaged by the SEM. An adjustable SEM mount was used in order to see both the top surface and cross-section of the remineralized sample. SEM characterization was performed using a JEOL 6010 SEM.

Thermal Cycling

Figure 9:
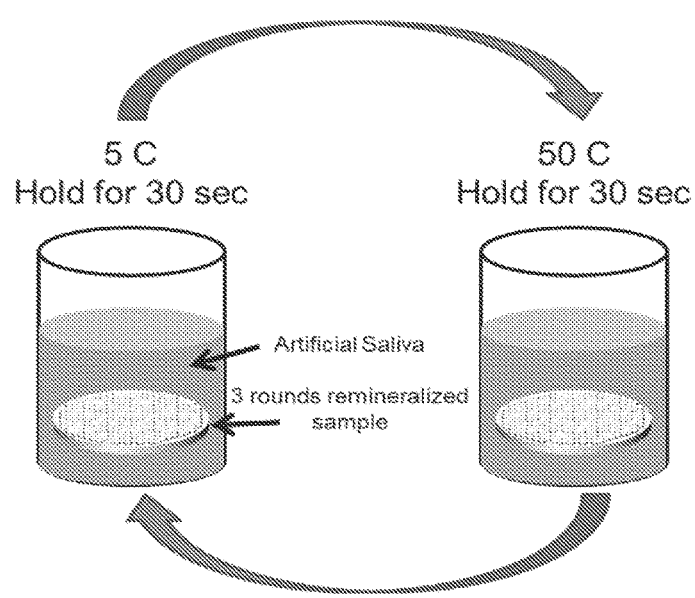

To ensure the thermal durability of the newly formed mineral layer on the dentin surface, thermal cycling tests were conducted on remineralized samples. Example thermal cycling process is shown in FIG. 9. After three rounds of peptide-guided remineralization, the sample was placed in a vial containing an artificial saliva solution consisting of 130 mM KCl, 20 mM HEPES, 1.5 mM $CaCl_2$, 0.9 mM $KH_2PO_4$, and 1 mM NaCl. In order to mimic the temperature changes in the natural oral environment, the remineralized sample was cycled between 5 C and 50 C, holding for 30 seconds at each temperature. SEM images were taken of the mineral layer after 200 cycles (6 days) and 2,500 cycles (90 days) to compare the effects of thermal cycling at different time periods.

pH Cycling

Figure 10:
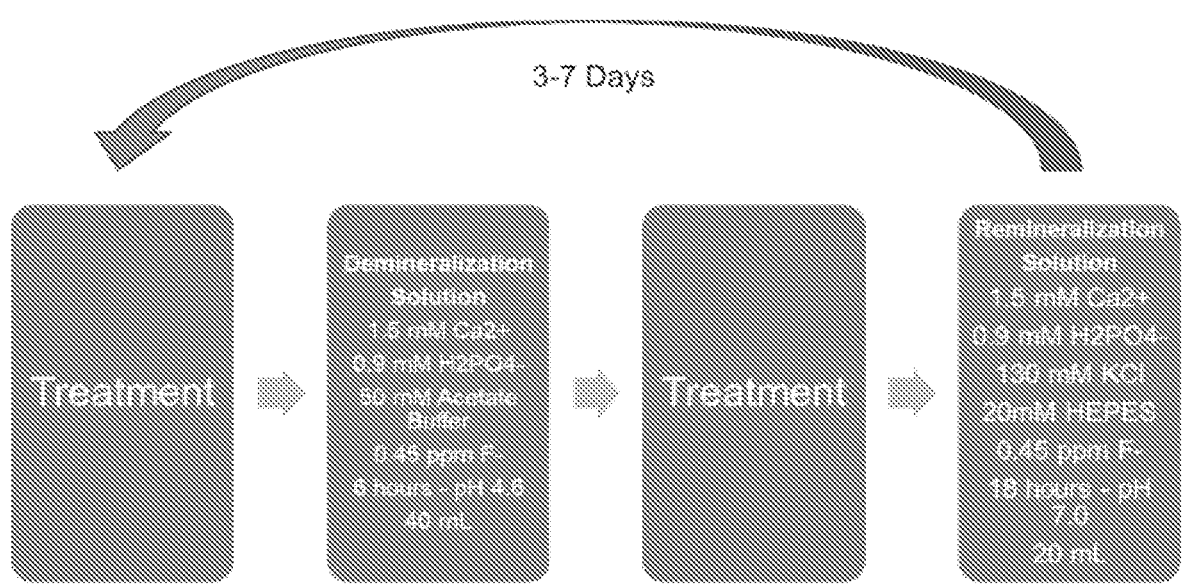
FIG. 10. Schematic representation of the pH cycling process

In order to confirm the chemical durability of the newly formed mineral layer on the dentin surface, pH cycling tests were conducted on remineralized samples. The pH cycling process is shown in FIG. 10. After three rounds of peptide-guided remineralization, the sample is subjected to a demineralizing solution, shown in FIG. 10, with a pH of 4.6 for 6 hours to mimic the acidity that occurs in the natural oral environment. Then, the sample undergoes another round of remineralization, labeled as "Treatment" in FIG. 10. The sample is then placed in a remineralizing solution at pH 7 for 18 hours, to mimic the neutral oral environment. The cycle continues as shown in FIG. 6 for 3-7 days, at which the sample is prepared for SEM imaging.

Results and Discussions

Occlusion of Dentinal Tubules

Figure 11:
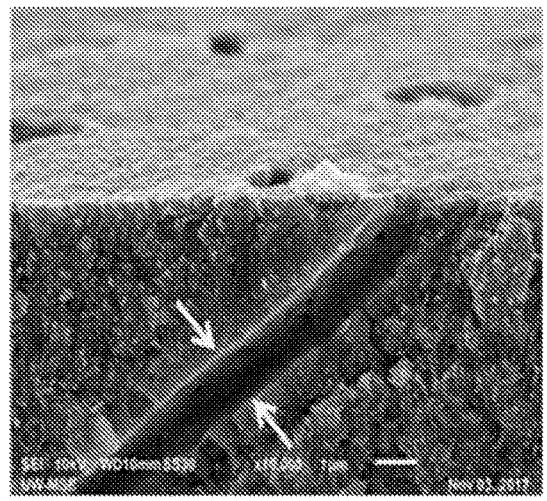
FIG. 11. SEM images showing remineralized layer on dentin surface and within dentin tubules.
Figure 11:
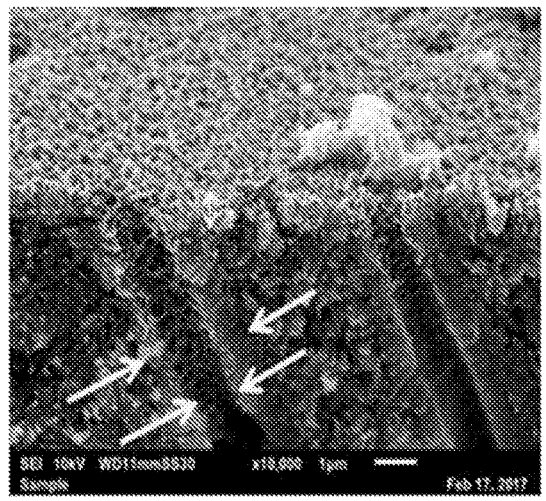
Figure 11:
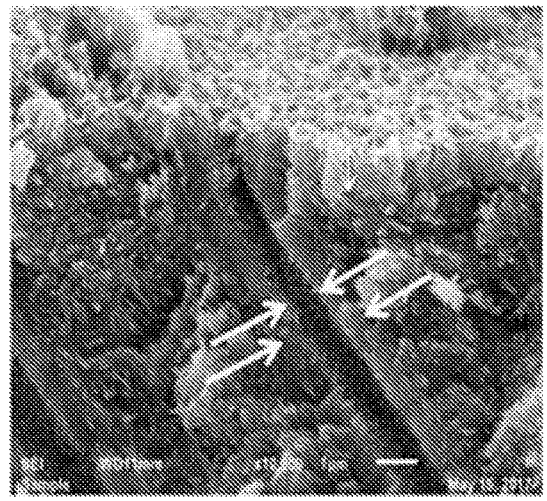
Figure 11:
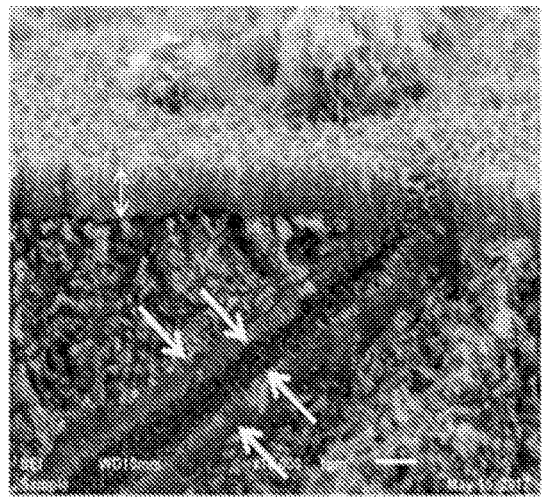

After samples were subjected to the peptide-guided remineralization treatment, the newly formed mineral layer was characterized through SEM. FIG. 11 shows a comparative view of the thickness of the mineral and level of tubule occlusion over 0-3 rounds of remineralization. The yellow arrows indicate the qualitative width of the tubule and thickness mineral layer. FIG. 11a shows a cross section of a prepared sample with no remineralization and the bare surface of the dentin and inner wall of the tubule can be seen. After 1 round of remineralization (FIG. 11b), it can be seen that a layer of mineral has formed on the surface of the dentin and the mineral has also penetrated into the tubules. The flake-like features seen is the newly grown mineral. As the number of rounds increase, so does the thickness of the mineral layer on the surface and the amount of mineral penetrating into the tubules, seen by comparing FIG. 11a to 11d which shows 3 rounds of remineralization. The tubule in FIG. 11d also appears to be fully occluded, as mineral is covering the opening of the tubule on the surface of the dentin. Another aspect to observe is the interface between the existing dentin and new mineral, which appears through SEM to be cohesive and compatible, mimicking the natural interface between enamel and dentin. These results show that the peptide-guided remineralization treatment does indeed form a new mineral layer on the dentin surface as well as occlude the tubules with mineral penetration.

Thermal Cycling

Figure 12:
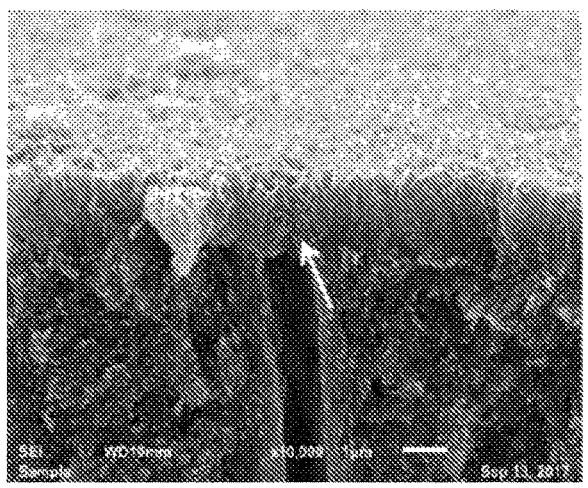
FIG. 12. SEM images showing mineral morphology before and after thermal cycling.
Figure 12:
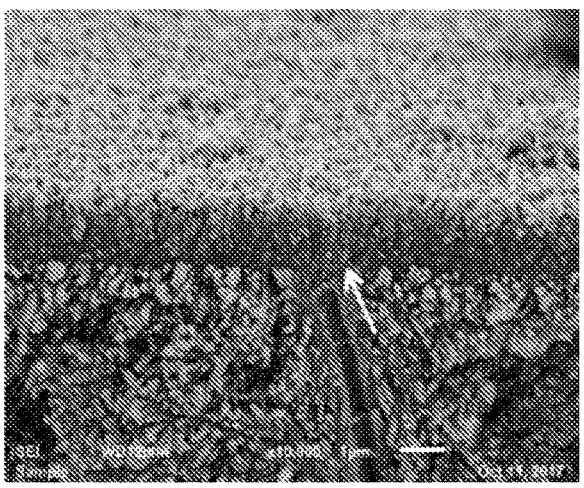
Figure 12:
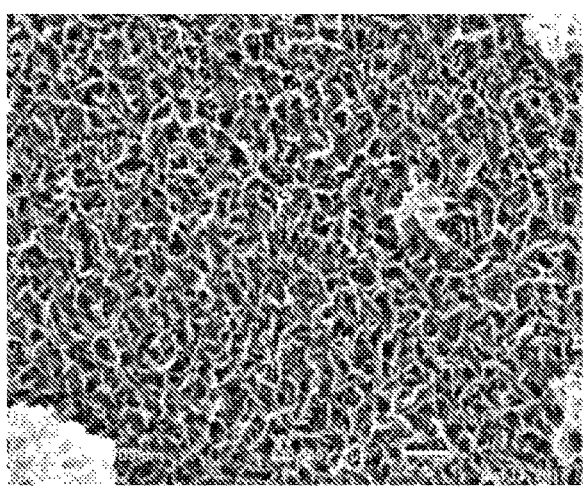
Figure 12:
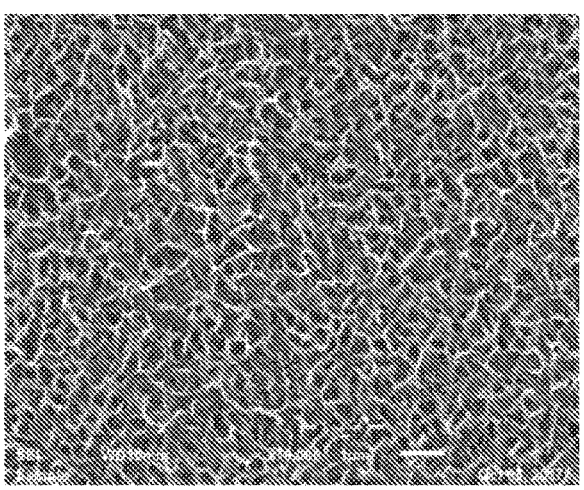
Figure 12:
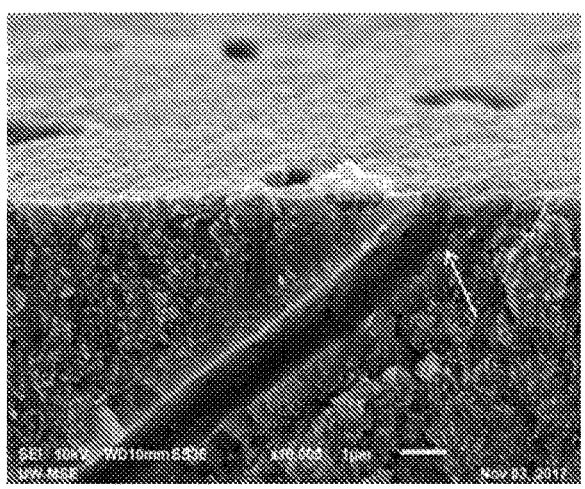
Figure 12:
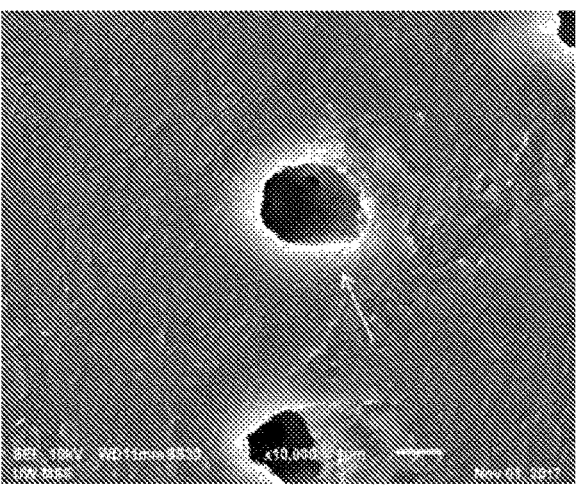

FIG. 12 shows before and after SEM images of 3 round remineralized samples that underwent the thermal cycling procedure described above. The yellow arrows indicate the mineral layer on the surface of the dentin. FIG. 12a shows the cross-section of a 3 round remineralized sample where no thermal cycling has taken place while FIG. 12b shows the same sample after 2,500 cycles (90 days). Similarly, FIG. 12c shows a top view of the mineral layer on the dentin surface before thermal cycling while FIG. 12d shows the same sample after 2,500 cycles. FIGS. 12e and 12f show a cross-section and top view image of a prepared sample with no remineralization, respectively, for reference. By reviewing the images, it can be seen that the mineral layer is still present after 90 days of thermal cycling and therefore thermally stable on the surface of dentin. This reinforces the idea of a cohesive interface of the mineral layer with the dentin surface and shows that peptide-guided remineralization is a thermally durable and long-lasting treatment. While the mineral is thermally stable, it can be observed that the morphology of the mineral seems to slightly change and the density of the mineral increases. Further studies need to be conducted to find the cause of these changes.

CONCLUSIONS

This example provides a peptide-guided remineralization treatment method to form a new mineral layer on a surface of a substrate and successfully occluding dentinal tubules with mineral penetration. The remineralized layer has also shown to be thermally stable after a 90-day thermal cycling treatment. The mineral formed by the peptide-guided remineralization process is a viable and natural alternative to current solutions to hypersensitivity and can provide a durable, compatible, and cohesive interface with the existing tooth structure. To further ensure the durability of the newly formed mineral layer, characterization has been performed to evaluate the mechanical and chemical stability. With this aim, nanomechanical characterization tests and pH cycling can be performed on remineralized dentin surfaces, as well as analysis of sample preparation with ideal tubule orientation for identification of changes in mineral morphology after thermal cycling is conducted.

REFERENCES FOR EXAMPLE 2

[1] West N X, Hughes J A, Addy M. 2002. Dentine hypersensitivity: the effects of brushing toothpaste on etched and unetched dentine in vitro. J. Oral rehabilitation. 29(2) 167-174.

[3] Schmidlin P, Sahrmann P. 2013. Current management of dentin hypersensitivity. Clinical Oral Investigation. 17(1) 55-59.

[4] Lee S Y, Kwon H K, Kim B I. 2008. Effect of dentinal tubule occlusion by dentifrice containing nano-carbonate apatite. J. Oral Rehabilitation. 35(1) 847-853.

[5] Porto I, Andrade A, Montes M. 2009. Diagnosis and treatment of dentinal hypersensitivity. J. Oral Science. 51(3) 323-332.

[6] Dogan S, Fong H K, Yucesoy D T, Cousin T, Gresswell C G, Dag S, Huang G L, Sarikaya M. 2018. Biomimetic Tooth Repair: Amelogenin-derived peptide enables in vitro remineralization of human enamel. ACS Biomater Sci Eng. 4(5):1788-1796.

[7] Ruan Q, Liberman D, Bapat R, Chandrababu K B, Phark J H, Moradian-Oldak J. 2016. J. Biomed Eng Inform. 2(1) 119-128.

We claim:

1. A composition or kit, comprising
(a) a first formulation comprising an effective amount to treat a dental disorder, whiten teeth, restore and retain the tooth structure, and/or restore the mineral content of tooth-mineral loss due to demineralization, of a polypeptide comprising or consisting of the amino acid sequence selected from the group consisting of:
(SYENSHSQAINVDRT)$_{1-10}$ (shADP5; SEQ ID NO:16);
(SYEKSHSQAINTDRT)$_{1-10}$ (sADP5; SEQ ID NO:24);
(WP(A/S)TDKTKREEVD)$_{1-10}$ (ADP3; SEQ ID NO:7);
(PGYIN(L/F)SYE(K/N)SHSQAIN(T/V)DRTA)$_{1-10}$ (ADP5; SEQ ID NO:13);
(LPPLFSMPLSPILPELPLEAWPAT)$_{1-10}$ (ADP6; SEQ ID NO:17);
(HPP(S/T)HTLQPHHH(L/I)PVVPAQ QPV(A/I) PQQPMMPVPG(H/Q)HSMTP (T/I)QH)$_{1-10}$ (ADP7; SEQ ID NO:18); and
12-42 contiguous amino acids of (HPP(S/T) HTLQPHHH(L/I)PVVPAQ QPV(A/I) PQQPMMPVPG(H/Q)HSMTP(T/I)QH)$_{1-10}$ (ADP7; SEQ ID NO:18); or combinations thereof; and
(b) one or more further formulations comprising at least one calcium ion source and at least one phosphate ion source;
wherein the first formulation is configured to release the polypeptide more rapidly than $Ca^{2+}$ is released from the at least one calcium ion source; and wherein the first formulation is configured to release the polypeptide more rapidly than $PO_4^{3-}$ is released from the at least one phosphate ion source;
wherein
(i) the one or more further formulations comprise the at least one calcium ion source at a concentration of from about 1 mM to about 10 M; and
(ii) the one or more further formulations comprise the at least one phosphate ion source at a concentration of from about 1 mM to about 10 M.

2. The composition or kit of claim 1, wherein the first formulation has a reduced viscosity compared to the one or more further formulations.

3. The composition or kit of claim 1, wherein the first formulation is tuned to modify aqueous solubility compared to the one or more further formulations.

4. The composition or kit of claim 1 wherein the calcium ion source comprises calcium acetate, calcium carbonate, calcium citrate, calcium chloride, calcium gluconate, calcium glycerophosphate, calcium lactate, calcium phosphate, or combinations thereof.

5. The composition or kit of claim 1, wherein the phosphate ion source comprises aluminum phosphates, calcium phosphates, potassium phosphates, sodium phosphates, or combinations thereof.

6. The composition or kit of claim 1 wherein the composition or kit has a molar ratio of the at least one calcium ion source to the at least one phosphate ion source of about 5:3.

7. The composition of claim 1, wherein the composition or kit has a molar ratio of the polypeptide to a combination of the at least one calcium ion source and the at least one phosphate ion source of from about 1:2 to about 1:100.

8. The composition or kit of claim 1, wherein the one or more further formulations comprises a second formulation, wherein the first formulation and the second formulation are present in a lozenge or a gum.

9. The composition or kit of claim 8, wherein the lozenge or gum comprises:
(i) a core region comprising the second formulation; and
(ii) a shell region comprising the first formulation.

10. The composition or kit of claim 8, wherein the second formulation comprises:
(A) 0.1%-80%, 0.5%-80%, 1%-80%, 5%-80%, 10%-80%, 20%-75%, 30-70%, 40%-65%, 45%-60%, 50%-60%, 52%-58%, 53%-57%, 54%-56%, or about 54-55% w/w of the calcium ion source, the calcium ion source comprising $CaCl_2.H_2O$; and
(B) 0.1%-80%, 0.5%-80%, 1%-80%, 5%-80%, 10%-80%, 10%-60%, 15%-50%, 20%-40%, 25%-35%, 27%-33%, 28%-32%, 29%-31%, or about 29.5%-30.5% w/w of the potassium ion source, the phosphate source comprising $KH_2PO_4$.

11. The composition or kit of claim 10, wherein the second formulation further comprises one or more lubricants, flavoring agents, and/or excipients.

12. The composition or kit of claim 8, wherein the second formulation comprises:
0.1%-80%, 0.5%-80%, 1%-80%, 5%-80%, 10%-80%, 20%-75%, 30-70%, 40%-65%, 45%-60%, 50%-60%, 52%-58%, 53%-57%, 54%-56%, or about 54-55% w/w of calcium ion source, the calcium ion source comprising $CaCl_2.H_2O$;
0.1%-80%, 0.5%-80%, 1%-80%, 5%-80%, 10%-80%, 10%-60%, 15%-50%, 20%-40%, 25%-35%, 27%-33%, 28%-32%, 29%-31%, or about 29.5%-30.5% w/w of phosphate ion source, the phosphate ion source comprising $KH_2PO_4$; and
1%-10% w/w lubricant.

13. The composition or kit of claim 1, wherein the first formulation comprises 0.1%-10%, 0.5-7.5%, 1%-6%, 1.5%-5%, 2%-4%, or about 2.5% to about 3.5% w/w of the polypeptide.

14. The composition or kit of claim 1, wherein the first formulation further comprises one or more lubricant, flavoring agent, and/or filler.

15. The composition or kit of claim 1, wherein the first formulation comprises:
   0.1%-10%, 0.5-7.5%, 1%-6%, 1.5%-5%, 2%-4%, or about 2.5% to about 3.5% w/w of the polypeptide; and
   1%-10% w/w lubricant.

16. The composition or kit of claim 1, wherein the one or more further formulations comprises a second formulation, wherein the second formulation is an aqueous formulation, and wherein the first formulation is an aqueous formulation.

* * * * *